United States Patent
Sugio et al.

(10) Patent No.: US 8,333,475 B2
(45) Date of Patent: Dec. 18, 2012

(54) ELECTRO-OCULOGRAPHY MEASURING DEVICE, OPHTHALMOLOGICAL DIAGNOSIS DEVICE, EYE-GAZE TRACKING DEVICE, WEARABLE CAMERA, HEAD-MOUNTED DISPLAY, ELECTRONIC EYEGLASSES, ELECTRO-OCULOGRAPHY MEASURING METHOD, AND RECORDING MEDIUM

(75) Inventors: Toshiyasu Sugio, Osaka (JP); Daisuke Sato, Osaka (JP)

(73) Assignee: Panasonic Corporation, Osaka (JP)

( * ) Notice: Subject to any disclaimer, the term of this patent is extended or adjusted under 35 U.S.C. 154(b) by 286 days.

(21) Appl. No.: 12/939,264

(22) Filed: Nov. 4, 2010

(65) Prior Publication Data

US 2011/0170065 A1 Jul. 14, 2011

(30) Foreign Application Priority Data

Nov. 12, 2009 (JP) ................................ 2009-258584

(51) Int. Cl.
*A61B 3/14* (2006.01)
(52) U.S. Cl. .................... 351/209; 351/205; 351/246
(58) Field of Classification Search .................. 351/205, 351/209, 246
See application file for complete search history.

(56) References Cited

U.S. PATENT DOCUMENTS 7,522,344 B1 * 4/2009 Curatu et al. ................. 359/634

FOREIGN PATENT DOCUMENTS

| JP | 9-34631 | 2/1997 |
| JP | 11-85384 | 3/1999 |
| JP | 11-276461 | 10/1999 |
| JP | 2002-272693 | 9/2002 |

OTHER PUBLICATIONS

Manabe et al., "Full-time Wearable Headphone-Type Gaze Detector" NTT DoCoMo Multimedia Laboratories, 2006 (with English Translation).

* cited by examiner

*Primary Examiner* — James Greece
(74) *Attorney, Agent, or Firm* — Wenderoth, Lind & Ponack, LLP.

(57) ABSTRACT

An electro-oculography measuring device includes: an electro-oculography measuring unit configured to measure an electro-oculography original signal; a view capturing unit configured to capture a view picture; a drift estimation processing unit configured to estimate a drift signal; and a subtractor which subtracts the drift signal from the electro-oculography original signal to output an electro-oculography signal, and the drift estimation processing unit includes: an electro-oculography change amount calculating unit configured to calculate an electro-oculography change amount; a motion vector estimating unit configured to estimate a motion vector of a moving object included in the view picture; a drift change amount estimating unit configured to estimate a drift change amount assuming that a change in a gaze direction follows a motion of the moving object; and a drift estimating unit configured to estimate the drift signal by adding the drift change amount to a past drift signal.

21 Claims, 65 Drawing Sheets

FIG. 6

| | | | | |
|---|---|---|---|---|
| -300 μV | -100 μV | 100 μV | 200 μV | 400 μV |
| -150 μV | -50 μV | 50 μV | 150 μV | 250 μV |
| -250 μV | -150 μV | -50 μV | 100 μV | 150 μV |
| -400 μV | -300 μV | -100 μV | -50 μV | 0 μV |

Block A (0, 1)
Block B (1, 3)
m
n

Generated-electro-oculogram table

FIG. 7

| Block position | Motion vector | Motion-vector-equivalent electro-oculography change amount |
|---|---|---|
| (0, 0) | (1, 2) | -350 μV |
| (0, 1) | (1, 2) | -250 μV |
| (0, 2) | (0, 0) | 0 μV |
| ... | ... | ... |
| (2, 3) | (1, -3) | 500 μV |
| (2, 4) | (1, -3) | 450 μV |
| ... | ... | ... |
| (3, 4) | (0, 0) | 0 μV |

Electro-oculography change amount candidate table

Electro-oculography change amount vector

Electro-oculography change amount candidate vectors

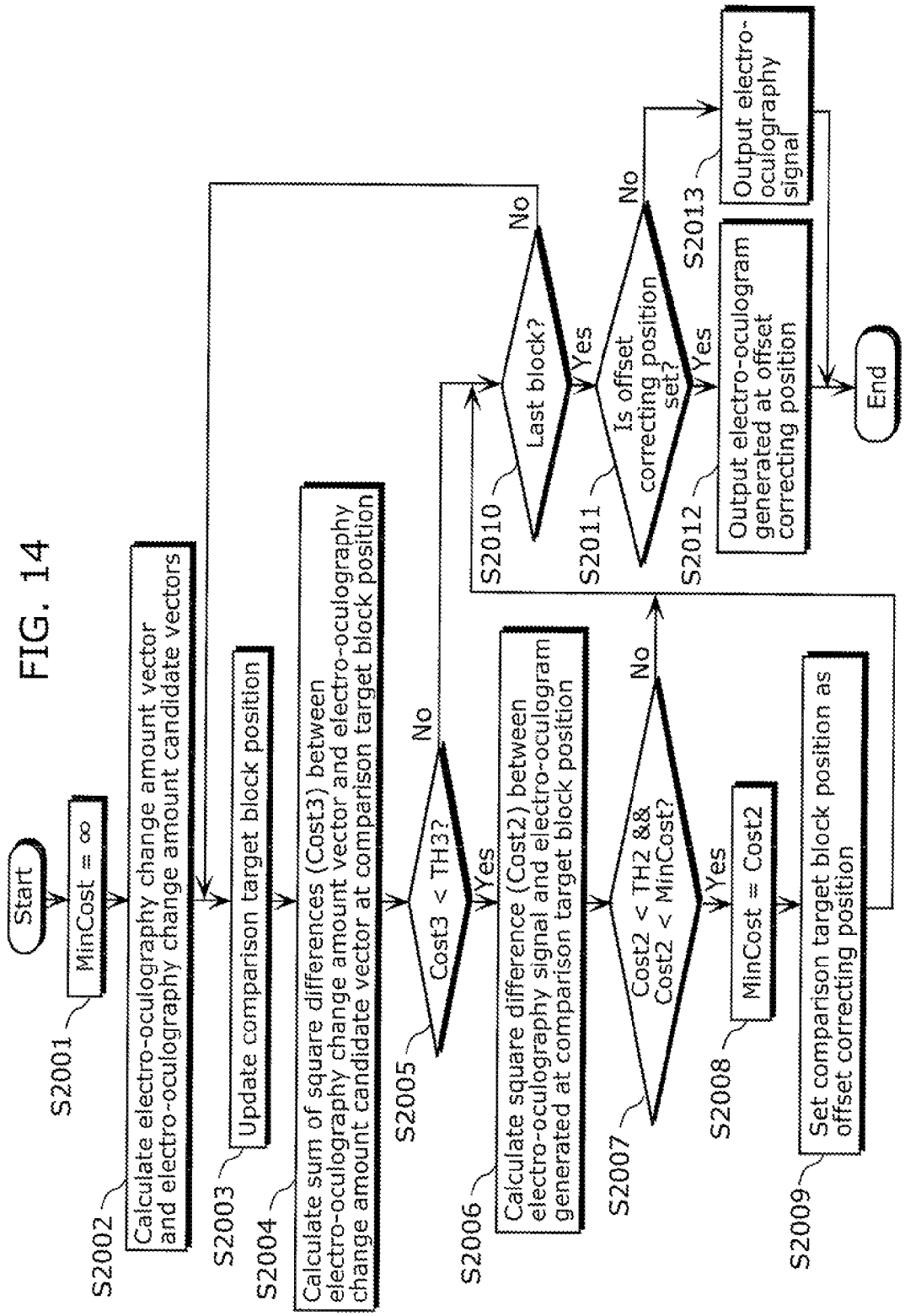

FIG. 53A

| Electro-oculography change amount | Eyeball movement angle |
|---|---|
| 5 V | 40° |
| 4.5 V | 30° |
| 4 V | 20° |
| ⋮ | ⋮ |
| -5 V | -40° |

FIG. 53B

| Electro-oculography change amount | Gaze position |
|---|---|
| 5 V | (600, 0) |
| 4.5 V | (500, 0) |
| 4 V | (400, 0) |
| ⋮ | ⋮ |
| -5 V | (-600, 0) |

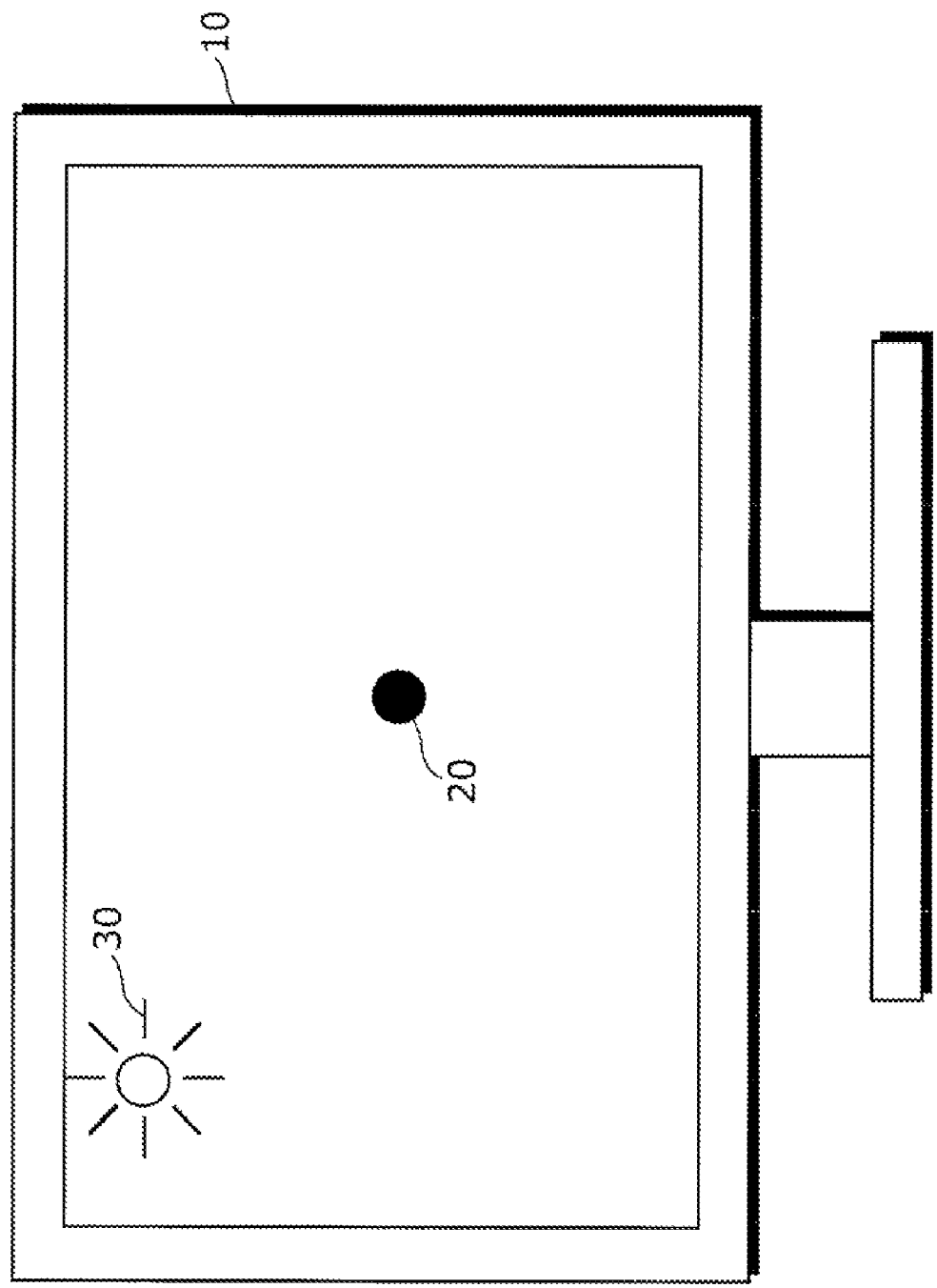

ELECTRO-OCULOGRAPHY MEASURING DEVICE, OPHTHALMOLOGICAL DIAGNOSIS DEVICE, EYE-GAZE TRACKING DEVICE, WEARABLE CAMERA, HEAD-MOUNTED DISPLAY, ELECTRONIC EYEGLASSES, ELECTRO-OCULOGRAPHY MEASURING METHOD, AND RECORDING MEDIUM

BACKGROUND OF THE INVENTION (1) Field of the Invention

The present invention relates to an electro-oculography measuring device which estimates a drift component, which is a baseline drift noise, from an electro-oculography original signal of a user, so as to output an electro-oculography signal from which an influence of a drift is removed.

(2) Description of the Related Art

In recent years, there have been presented gaze-path input interfaces and the like which utilize human eyeball movement. Methods for detecting human eyeball movement include: an EOG method that utilizes a potential generated between a cornea and a retina; a corneal reflex method that detects movement of a virtual image generated inside a cornea by irradiating an eyeball with a spotlight; a limbus tracking method that uses a difference in reflectance between a cornea and a sclera; a method using a contact lens; and so on.

Here, the EOG method is a method for detecting eyeball movement, utilizing the fact that a human cornea is charged positively with respect to the retina. More specifically, electrodes are attached near a human eyeball and a change in the potential measured by the electrodes is used to detect eyeball movement. FIG. 64A and FIG. 64B show examples of the method for detecting eyeball movement using the EOG method. FIG. 64A and FIG. 64B are examples of the case where electrodes are attached on the inner and outer sides of the right eye of a user with an equal distance from the center of the eyeball.

Assuming the electro-oculogram generated in the outer-side electrode A is Va and the electro-oculogram generated in the inner-side electrode B is Vb, Va and Vb are equal when the eyeball of the user is at the center as in FIG. 64A, and an electro-oculogram Va-b of 0 V is thereby measured. On the other hand, in the case where the user looks to the right as in FIG. 64B, the electrode A becomes closer to the cornea of the right eye, and thus Va becomes greater than Vb and the measured electro-oculogram Va-b indicates a plus value. Conversely, in the case where the user looks to the left, Va becomes smaller than Vb and the measured electro-oculogram Va-b indicates a minus value. Thus, it can be observed that the user's eye has moved to the right when the measured electro-oculogram Va-b indicates a plus value, and that the user's eye has moved to the left when the measured electro-oculogram Va-b indicates a minus value. With the EOG method, eyeball movement of the user is detected by utilizing such changes in the measured electro-oculogram Va-b as described above.

When detecting eyeball movement using the EOG method, a phenomenon called a drift occurs. A drift is a phenomenon in which the baseline of an electro-oculography original signal changes temporally, and it is considered to be caused by such factors as the materials of the electrodes used for measuring the electro-oculogram and a change in the state of contact between the skin and the electrodes.

FIG. 65 shows a result of electro-oculography measurement performed using electrodes actually attached to a user. FIG. 65 shows a result of electro-oculography measurement when a plurality of indexes are displayed for one second each in the order shown in FIG. 66. Referring to FIG. 65, it can be seen that the baseline of the measured electro-oculogram changes with time. More specifically, due to an influence of the drift, a change occurs in the measured electro-oculogram also when the user gazes at the index (R4). That is to say, the detection of the user's eyeball movement becomes erroneous if the measuring result including a drift is used as the electro-oculogram.

Patent Literatures 1 and 2 below disclose an example of a method of removing the drift component.

With the method of removing the drift component disclosed in Patent Literature 1, the user is instructed to gaze at a particular position (the center of a display, for example) for such a short time that the influence of the drift does not occur, and a value of fluctuations caused by the drift is updated every time the user is instructed to gaze at a particular position, to thereby remove the drift component.

With the method of removing the drift component disclosed in Patent Literature 2, a calibration symbol is generated on a display screen as necessary. When saccadic movement is detected within a predetermined time period, it is determined that the user has gazed at the calibration symbol, and an error caused by the drift component is reset.

Patent Literature

Patent Literature 1: Japanese Unexamined Patent Application Publication No. 11-85384
Patent Literature 2: Japanese Unexamined Patent Application Publication No. 9-34631
Patent Literature 3: Japanese Unexamined Patent Application Publication No. 11-276461
Patent Literature 4: Japanese Unexamined Patent Application Publication No. 9-034631
Patent Literature 5: Japanese Unexamined Patent Application Publication No. 2002-272693
Patent Literature 6: Japanese Unexamined Patent Application Publication No. 11-85384

Non-Patent Literature

Non-Patent Literature 1: Hiroyuki Manabe and Masaaki Fukumoto, "Full-time Wearable Headphone-Type Gaze Detector", Interaction 2006, pages 23-24, 2006

In Patent Literature 1, the drift component is extracted by making the user gaze at a particular position on a regular basis. However, when measuring natural eyeball movement, there is a problem of difficulty in making the user gaze at a particular position on a regular basis.

In Patent Literature 2, it is determined, using saccadic movement which has occurred within a predetermined time period, whether or not the user has gazed at the calibration symbol generated on the display screen. However, it is difficult to determine whether the detected saccadic movement was induced by the generated calibration symbol or by another factor. In addition, there is also a problem that the drift component cannot be removed when there is no display on which to generate the calibration symbol.

SUMMARY OF THE INVENTION

The present invention, conceived to solve the above problems, aims to provide an electro-oculography measuring device that estimates a drift component, which is a baseline drift, from an electro-oculography original signal of a user, and outputs an electro-oculography signal from which an influence of a drift is removed.

More specifically, the drift component is estimated based on a motion vector in a view picture and an amount of change in electro-oculogram, using the properties of tracking movement, which is one form of human eyeball movement, that tracking movement does not occur without a tracking target in view when the eye is open.

An electro-oculography measuring device according to an aspect of the present invention is an electro-oculography measuring device which outputs an electro-oculography signal indicating a gaze direction of a user. Specifically, the electro-oculography measuring device includes: an electro-oculography measuring unit configured to measure an electro-oculography original signal indicating an electro-oculogram resulting from eyeball movement of the user; a capturing unit configured to capture a picture in the gaze direction of the user; a drift estimation processing unit configured to estimate a drift signal indicating a temporal baseline drift of the electro-oculography original signal; and a subtraction unit configured to subtract the drift signal estimated by the drift estimation processing unit from the electro-oculography original signal measured by the electro-oculography measuring unit, so as to output an electro-oculography signal. The drift estimation processing unit includes: an electro-oculography change amount calculating unit configured to calculate, based on a past electro-oculography signal output from the subtraction unit, an electro-oculography change amount indicating an amount of change in electro-oculogram over a predetermined time period in past; a motion vector estimating unit configured to estimate a motion vector of a moving object included in the picture captured by the capturing unit, the motion vector indicating a motion of the moving object in the predetermined time period in the past; a drift change amount estimating unit configured to estimate a drift change amount assuming that a change in the gaze direction indicated by the electro-oculography change amount follows the motion of the moving object indicated by the motion vector, the drift change amount being an amount of change in drift signal over the predetermined time period in the past; and a drift estimating unit configured to estimate the drift signal by adding the drift change amount estimated by the drift change amount estimating unit to a past drift signal.

As in the above configuration, by estimating the drift change amount based on a motion vector in a picture (view picture) and an electro-oculography change amount, it is possible to estimate the drift component in real time. As a result, it is possible to measure an electro-oculography signal from which an influence of a drift is removed.

The drift estimation processing unit may further include a saccade detecting unit configured to determine, based on the past electro-oculography signal output from the subtraction unit, whether or not saccadic movement occurred in the predetermined time period in the past, and to output a saccade detection signal to the drift estimating unit when determining that the saccadic movement occurred, the saccadic movement being rapid eyeball movement. The drift estimating unit may be configured to add the drift change amount output from the drift change amount estimating unit to the past drift signal when not obtaining the saccade detection signal from the saccade detecting unit. This makes it possible to accurately estimate the drift change amount using a motion vector and an electro-oculography change amount even when a saccade occurs during the user's eyeball movement.

The electro-oculography change amount calculating unit may be further configured to output a fixation detection signal to the drift estimating unit when the calculated electro-oculography change amount is below a predetermined threshold, the fixation detection signal indicating that an eyeball of the user was fixed in the predetermined time period in the past. The drift estimating unit may be configured to add the drift change amount output from the drift change amount estimating unit to the past drift signal when not obtaining the fixation detection signal from the electro-oculography change amount calculating unit. This makes it possible to accurately estimate the drift change amount using a motion vector and an electro-oculography change amount even when a fixation occurs during the user's eyeball movement.

As an example, the predetermined time period in the past may be a time period between a first time point in the past and a second time point preceding the first time point. The motion vector estimating unit may be configured to calculate a plurality of first motion vectors each indicating a position, in a second picture captured at the second time point, of a corresponding one of a plurality of blocks constituting a first picture captured at the first time point. The drift change amount estimating unit may be further configured to: hold, in advance, a generated-electro-oculogram table in which a gaze direction of the user and a generated electro-oculogram are associated with each other, the generated electro-oculogram being an electro-oculogram generated in the gaze direction; calculate, using the generated-electro-oculogram table, a motion-vector-equivalent electro-oculography change amount for each of the first motion vectors estimated by the motion vector estimating unit, the motion-vector-equivalent electro-oculography change amount indicating an amount of change in electro-oculogram assuming that the gaze direction of the user has moved along the motion vector; extract, from the first motion vectors, one or more first motion vectors having a difference equal to or below a predetermined threshold between a corresponding motion-vector-equivalent electro-oculography change amount and the electro-oculography change amount calculated by the electro-oculography change amount calculating unit; and estimate, as the drift change amount, a difference between a first electro-oculography signal output from the subtraction unit at the first time point and a generated electro-oculogram which, among generated electro-oculograms held in the generated-electro-oculogram table, corresponds to a start position of one of the extracted one or more first motion vectors.

As in the above configuration, by extracting a motion vector based on an electro-oculography change amount and a motion-vector-equivalent electro-oculography change amount, and estimating the drift change amount using a generated electro-oculogram at the start position of the extracted motion vector (offset correcting position), it is possible to reset the offset accumulated due to a drift, thereby allowing accurate electro-oculography measurement.

In addition, the drift change amount estimating unit may be configured to estimate the drift change amount by subtracting, from the first electro-oculography signal, a smallest value of differences between the first electro-oculography signal and generated electro-oculograms each corresponding to a start position of a corresponding one of the extracted first motion vectors. This makes the value of the drift change amount smaller, thereby making it possible to reduce an influence caused by false detection of the offset correcting position.

Alternatively, the drift change amount estimating unit may be configured to estimate the drift change amount by subtracting, from the first electro-oculography signal, a median value of differences between the first electro-oculography signal and generated electro-oculograms each corresponding to a start position of a corresponding one of the extracted first motion vectors. This makes it possible to detect, as the offset correcting position, a position close to the center of the moving object, thereby enhancing the accuracy of the drift change amount estimation.

As another example, the predetermined time period in the past may be a time period between the first time point and a third time point preceding the second time point. The motion vector estimating unit may be further configured to calculate a plurality of second motion vectors each indicating a position, in a third picture captured at the third time point, of a corresponding one of a plurality of blocks constituting the second picture captured at the second time point. The drift change amount estimating unit may be further configured to: calculate, using the generated-electro-oculogram table, a motion-vector-equivalent electro-oculography change amount for each of the second motion vectors estimated by the motion vector estimating unit, the motion-vector-equivalent electro-oculography change amount indicating an amount of change in electro-oculogram assuming that the gaze direction of the user has moved along the motion vector; extract, from combinations of one of the first motion vectors and one of the second motion vectors, one or more first motion vectors having a correlation coefficient equal to or above a predetermined threshold, the correlation coefficient being a correlation coefficient between a transition of a corresponding motion-vector-equivalent electro-oculography change amount and a transition of the electro-oculography change amount from the third time point to the first time point which is calculated by the electro-oculography change amount calculating unit, each of the first motion vector and the second motion vector in each combination representing a motion with respect to a same block; and estimate, as the drift change amount, a difference between the first electro-oculography signal output from the subtraction unit at the first time point and a generated electro-oculogram which, among the generated electro-oculograms held in the generated-electro-oculogram table, corresponds to a start position of one of the extracted one or more first motion vectors.

This allows determination of the offset correcting position using the characteristics of a temporal change amount of an electro-oculogram and a temporal change amount of a motion-vector-equivalent electro-oculogram, thereby further enhancing the accuracy of the drift change amount estimation.

The drift change amount estimating unit may be further configured to estimate the drift change amount by multiplying, by a corresponding correlation coefficient, a difference between the first electro-oculography signal output from the subtraction unit at the first time point and a generated electro-oculogram corresponding to a start position of one of the extracted one or more first motion vectors. This makes it possible to adjust the drift change amount according to a correlation between an electro-oculography change amount and a motion-vector-equivalent electro-oculography change amount.

As yet another example, the predetermined time period in the past may be a time period between a first time point in the past and a second time point preceding the first time point. The motion vector estimating unit may be configured to calculate a plurality of motion vectors each indicating a position, in a second picture captured at the second time point, of a corresponding one of a plurality of blocks constituting a first picture captured at the first time point. The drift change amount estimating unit may be further configured to: hold, in advance, a generated-electro-oculogram table in which a gaze direction of the user and a generated electro-oculogram are associated with each other, the generated electro-oculogram being an electro-oculogram generated in the gaze direction; calculate, using the generated-electro-oculogram table, a motion-vector-equivalent electro-oculography change amount for each of the motion vectors estimated by the motion vector estimating unit, the motion-vector-equivalent electro-oculography change amount indicating an amount of change in electro-oculogram assuming that the gaze direction of the user has moved along the motion vector; and estimate, as the drift change amount, a difference between the electro-oculography change amount calculated by the electro-oculography change amount calculating unit and a largest one of motion-vector-equivalent electro-oculography change amounts which respectively correspond to the motion vectors. This makes it possible to estimate, as the drift component, an electro-oculography change amount equal to or above the magnitude of a motion vector generated in a view picture, thereby enabling accurate electro-oculography measurement.

In addition, the saccade detecting unit may include: a delayed signal generating unit configured to delay the electro-oculography signal for a predetermined delay time to output a delayed signal; and a subtraction unit configured to subtract the delayed signal from the electro-oculography signal to generate an output signal. The saccade detecting unit may be configured to output the saccade detection signal to the drift estimating unit when the output signal is above a predetermined threshold. This allows detection of a saccade signal which is coded (that is, having information that indicates the moving direction of the eyeball).

Here, the predetermined delay time is preferably shorter than a time period for which the user gazes at an object. This prevents collapse of a saccade waveform.

In addition, the saccade detecting unit may include: a first filtering unit configured to perform one of maximum value filtering and minimum value filtering on the electro-oculography signal to output a first electro-oculography signal; and a subtraction unit configured to subtract one of the first electro-oculography signal and a second electro-oculography signal from the other one of the first electro-oculography signal and the second electro-oculography signal to generate an output signal, the second electro-oculography signal being obtained from the electro-oculography signal. The saccade detecting unit may be configured to output the saccade detection signal to the drift estimating unit when the output signal is above a predetermined threshold.

With the above configuration too, a saccade signal can be detected. It is to be noted that the "second electro-oculography signal" above is a signal directly or indirectly obtained from the electro-oculography signal input into the saccade detecting unit, and may be the electro-oculography signal itself which is input into the saccade detecting unit.

In addition, the saccade detecting unit may further include a second filtering unit configured to perform the other one of the maximum value filtering and the minimum value filtering on the electro-oculography signal to output the second electro-oculography signal. This allows easy obtainment of a saccade signal which includes a time at which a saccade has occurred.

Moreover, the saccade detecting unit may further include a second filtering unit configured to perform the other one of the maximum value filtering and the minimum value filtering on the first electro-oculography signal to output the second electro-oculography signal. This allows detection of a saccade signal as well as removal of a blink signal.

An ophthalmological-diagnosis device according to an aspect of the present invention is an ophthalmological diagnosis device including: the electro-oculography measuring device described above; and a diagnosis unit configured to diagnose a condition of an eye of the user based on the electro-oculography signal output from the electro-oculography measuring device.

An eye-gaze tracking device according to an aspect of the present invention is an eye-gaze tracking device which detects a gaze direction of a user from an electro-oculogram. Specifically, the eye-gaze tracking device includes: the electro-oculography measuring device described above; a calibration index presenting unit configured to present a calibration index to the user; a saccade detecting unit configured to detect saccadic movement from the electro-oculography signal output from the electro-oculography measuring device, and to output an electro-oculography change amount that is an amount of change in electro-oculogram before and after the saccadic movement, the saccadic movement being rapid eyeball movement which occurs when a gaze position of the user moves to the calibration index presented by the calibration index presenting unit; a calibration parameter calculating unit configured to calculate a calibration parameter based on a position of the calibration index presented by the calibration index presenting unit and the electro-oculography change amount output from the saccade detecting unit; and a calibration unit configured to detect the gaze direction of the user from the electro-oculography signal based on the calibration parameter.

A wearable camera according to an aspect of the present invention is a wearable camera which captures an image in a gaze direction of a user. Specifically, the wearable camera includes: an imaging unit; the eye-gaze tracking device described above; and an imaging control unit configured to cause the imaging unit to capture an image in a gaze direction detected by the eye-gaze tracking device.

A head-mounted display according to an aspect of the present invention is a head-mounted display which moves a mouse pointer in a gaze direction of a user. Specifically, the head-mounted display includes: a display unit configured to display an image and the mouse pointer; the eye-gaze tracking device described above; and a display control unit configured to move the mouse pointer displayed on the display unit, in a gaze direction detected by the eye-gaze tracking device.

Electronic eyeglasses according to an aspect of the present invention are electronic eyeglasses which change a focal point of each of lenses according to a gaze position of a user. Specifically, the electronic eyeglasses include: lenses each having a changeable focal point; the eye-gaze tracking device described above; and a focus control unit configured to change the focal point of each of the lenses according to a gaze position detected by the eye-gaze tracking device.

An electro-oculography measuring method according to an aspect of the present invention is an electro-oculography measuring method for outputting an electro-oculography signal indicating a gaze direction of a user. Specifically, the electro-oculography measuring method includes: measuring an electro-oculography original signal indicating an electro-oculogram resulting from eyeball movement of the user; capturing a picture in the gaze direction of the user; estimating a drift signal indicating a temporal baseline drift of the electro-oculography original signal; and subtracting the drift signal estimated in the estimating of a drift signal from the electro-oculography original signal measured in the measuring, so as to output an electro-oculography signal. The estimating of a drift signal includes: calculating, based on a past electro-oculography signal output in the subtracting, an electro-oculography change amount indicating an amount of change in electro-oculogram over a predetermined time period in past; estimating a motion vector of a moving object included in the picture captured in the capturing, the motion vector indicating a motion of the moving object in the predetermined time period in the past; estimating a drift change amount assuming that a change in the gaze direction indicated by the electro-oculography change amount follows the motion of the moving object indicated by the motion vector, the drift change amount being an amount of change in drift signal over the predetermined time period in the past; and estimating the drift signal by adding the drift change amount estimated in the estimating of a drift change amount, to a past drift signal.

A non-transitory computer-readable recording medium for use in a computer according to an aspect of the present invention is a non-transitory computer-readable recording medium having a program recorded thereon for causing the computer to output an electro-oculography signal indicating a gaze direction of a user. Specifically, the program causes the computer to execute: measuring an electro-oculography original signal indicating an electro-oculogram resulting from eyeball movement of the user; capturing a picture in the gaze direction of the user; estimating a drift signal indicating a temporal baseline drift of the electro-oculography original signal; and subtracting the drift signal estimated in the estimating of a drift signal from the electro-oculography original signal measured in the measuring, so as to output an electro-oculography signal. The estimating of a drift signal includes: calculating, based on a past electro-oculography signal output in the subtracting, an electro-oculography change amount indicating an amount of change in electro-oculogram over a predetermined time period in past; estimating a motion vector of a moving object included in the picture captured in the capturing, the motion vector indicating a motion of the moving object in the predetermined time period in the past; estimating a drift change amount assuming that a change in the gaze direction indicated by the electro-oculography change amount follows the motion of the moving object indicated by the motion vector, the drift change amount being an amount of change in drift signal over the predetermined time period in the past; and estimating the drift signal by adding the drift change amount estimated in the estimating of a drift change amount, to a past drift signal.

According to an aspect of the present invention, a drift component, which is a baseline drift, is estimated in real time from an electro-oculography original signal of a user based on a motion vector generated in a view picture and an electro-oculography change amount, thereby making it possible to provide an electro-oculography measuring device capable of measuring an electro-oculography signal from which an influence of a drift is removed.

The disclosure of Japanese Patent Application No. 2009-534785 filed on Aug. 13, 2009 including specification, drawings and claims is incorporated herein by reference in its entirety.

FURTHER INFORMATION ABOUT TECHNICAL BACKGROUND TO THIS APPLICATION

The disclosure of Japanese Patent Application No. 2009-258584 filed on Nov. 12, 2009 including specification, drawings and claims is incorporated herein by reference in its entirety.

BRIEF DESCRIPTION OF THE DRAWINGS

These and other objects, advantages and features of the invention will become apparent from the following description thereof taken in conjunction with the accompanying drawings that illustrate a specific embodiment of the invention. In the Drawings:

FIG. 6 is a diagram showing an example of a generated-electro-oculogram table which shows a correspondence between an eyeball position and an electro-oculogram generated at that position;

FIG. 7 is a diagram showing an example of an electro-oculography change amount candidate table which shows a correspondence between a block position, a motion vector generated from that position, and an electro-oculography change amount;

FIG. 14 is a flow chart showing an operation of an offset correcting position determining unit according to the second embodiment;

FIG. 53A is a diagram showing a table holding a plurality of combinations of an electro-oculography change amount and an eyeball movement angle associated with each other;

FIG. 53B is a diagram showing a table holding a plurality of combinations of an electro-oculography change amount and a gaze position associated with each other;

FIG. 54 is a diagram showing a state of a display on which a calibration index is displayed;

DESCRIPTION OF THE PREFERRED EMBODIMENT(S)

Hereinafter, embodiments according to the present invention will be described with reference to the drawings. It is to be noted that each embodiment described below may be combined with another embodiment in arbitrary combinations as long as an advantageous effect of the present invention is not diminished.

First Embodiment

Figure 1:
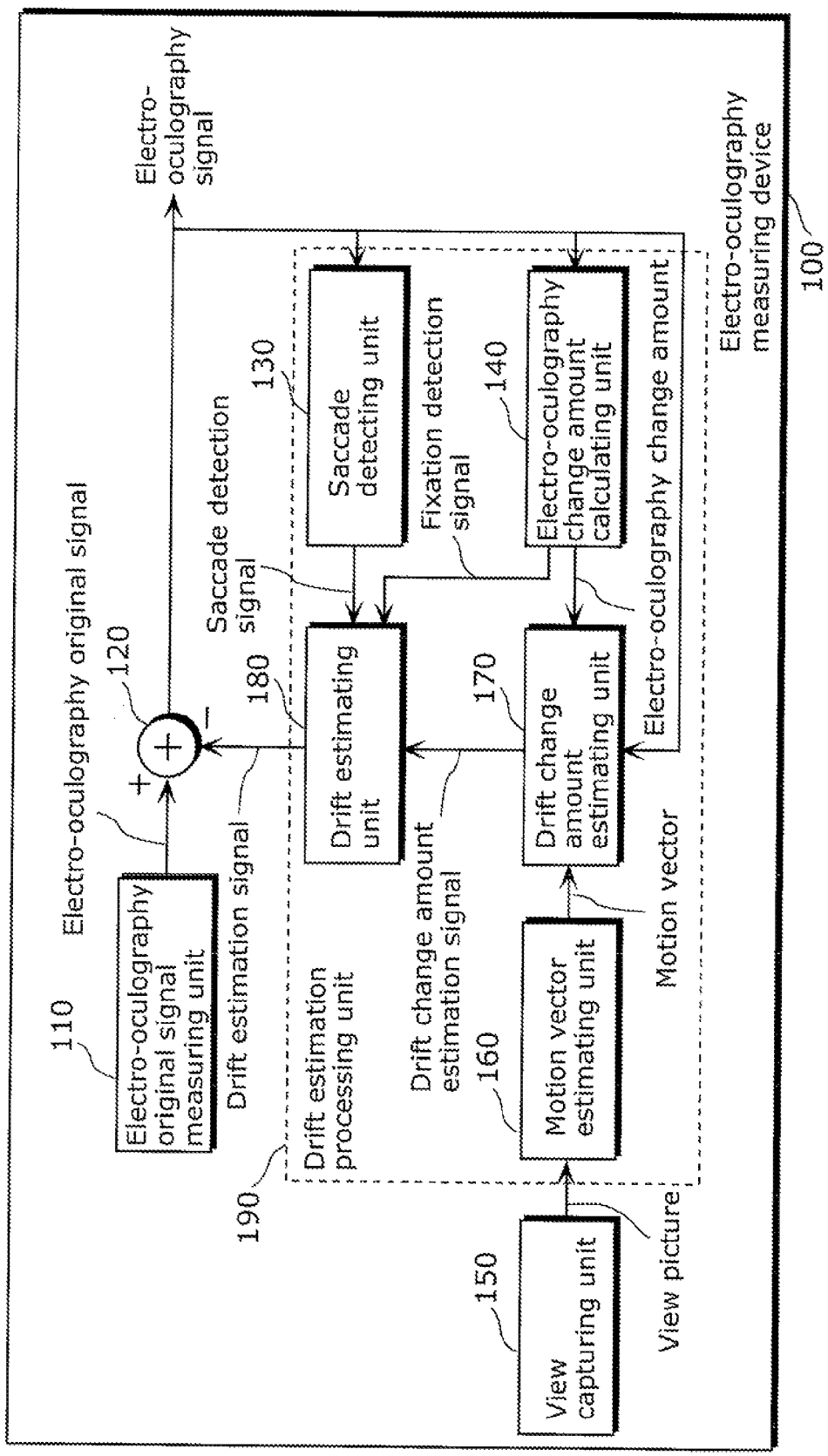
FIG. 1 is a block diagram of an electro-oculography measuring device according to a first embodiment.

FIG. 1 is a block diagram showing a configuration of an electro-oculography measuring device 100 according to a first embodiment of the present invention. The electro-oculography measuring device 100 shown in FIG. 1 includes an electro-oculography original signal measuring unit 110, a subtractor (subtraction unit) 120, a view capturing unit (capturing unit) 150, and a drift estimation processing unit 190.

The electro-oculography original signal measuring unit 110 measures an electro-oculogram generated in an electrode attached near an eye of a user, and outputs the electro-oculogram as an electro-oculography original signal. The electro-oculography original signal includes an electro-oculogram resulting from eyeball movement of the user, and a drift signal that indicates a temporal baseline drift of the electro-oculogram.

Figures 64A, 64B:
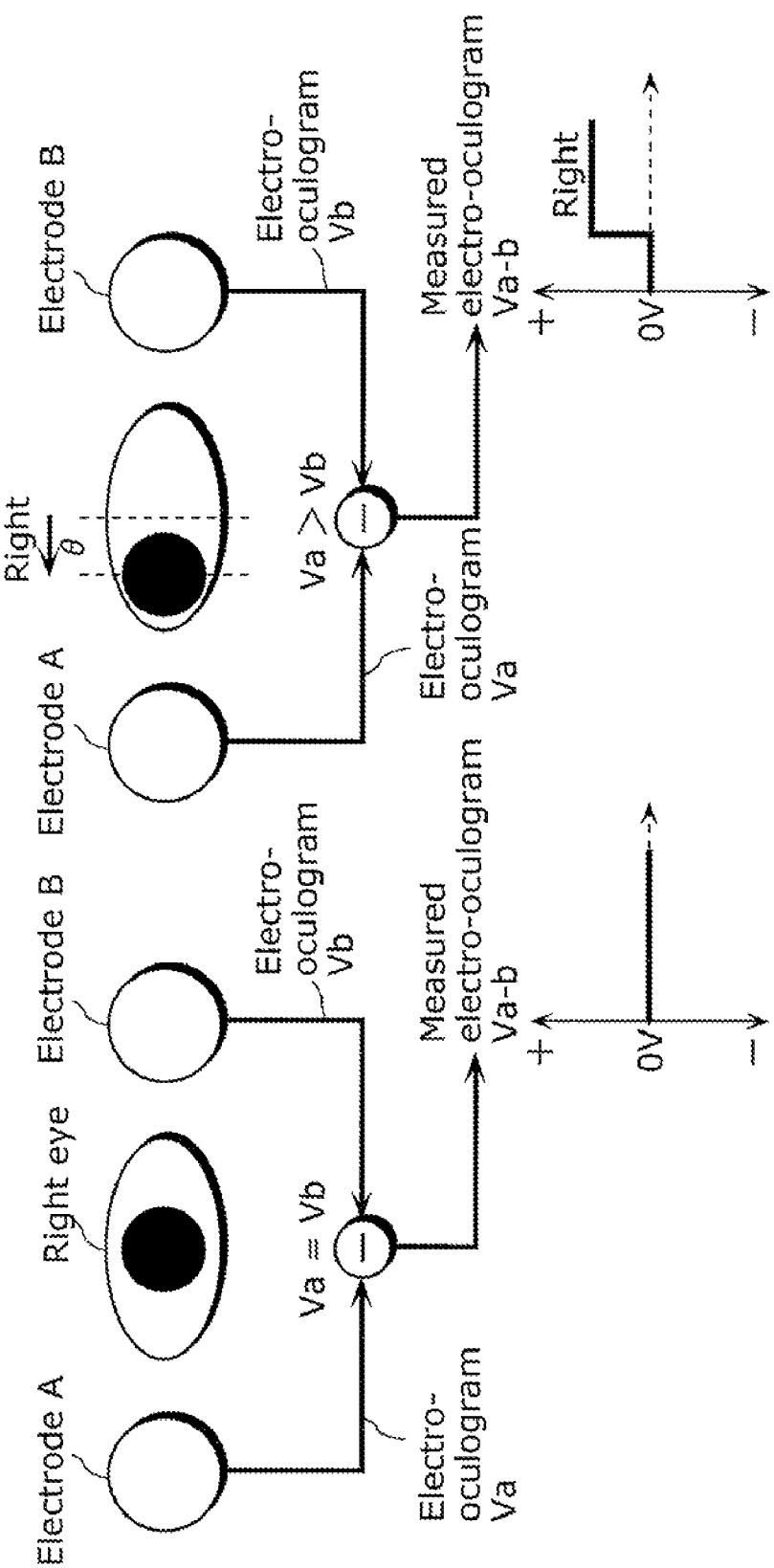
FIG. 64A is a diagram for explaining the EOG method, and shows a user's eyeball facing front.
FIG. 64B is a diagram for explaining the EOG method, and shows a user's eyeball facing to the right.
Figure 65:
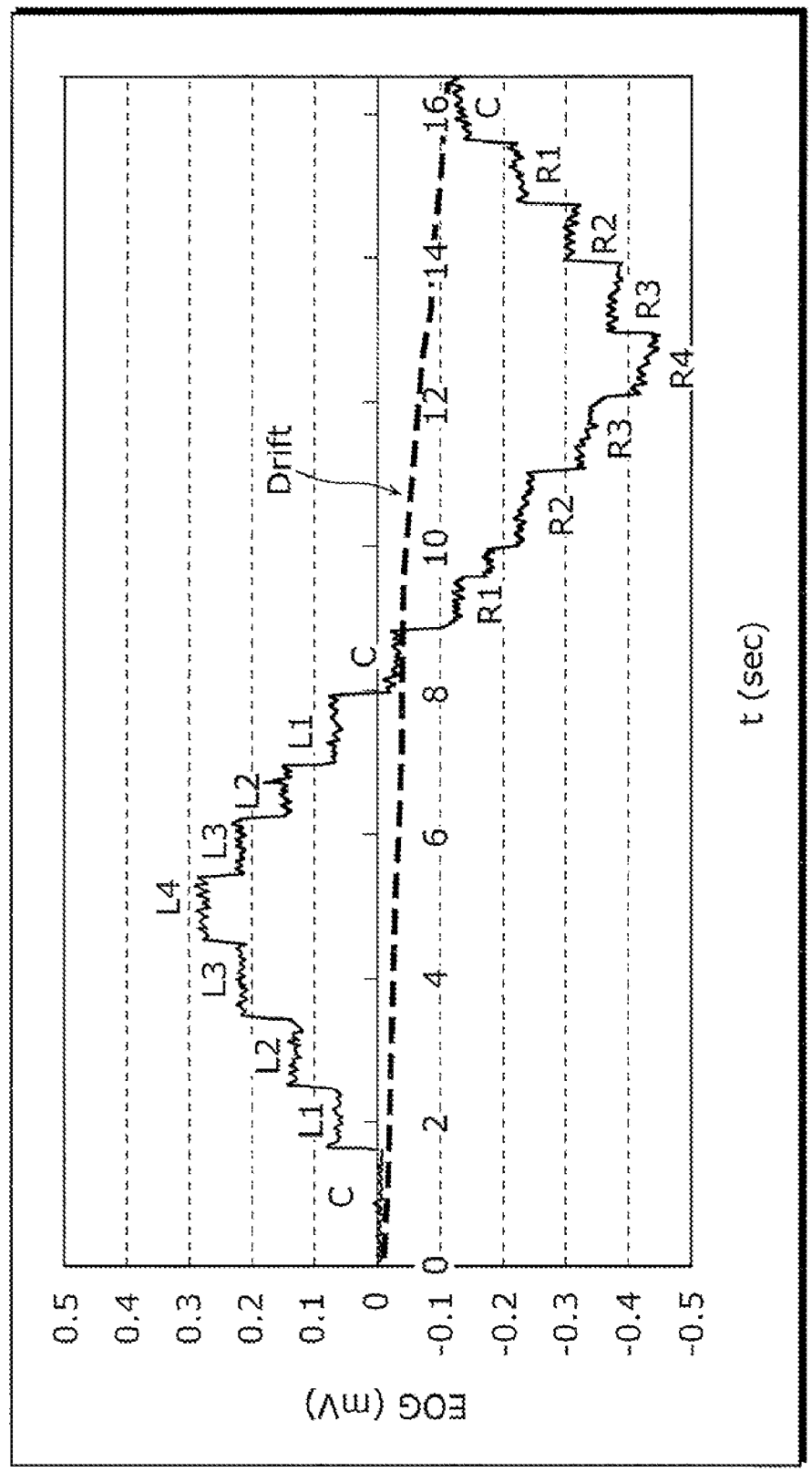
FIG. 65 is a diagram showing an example of a drift in electro-oculography measurement.
Figure 66:
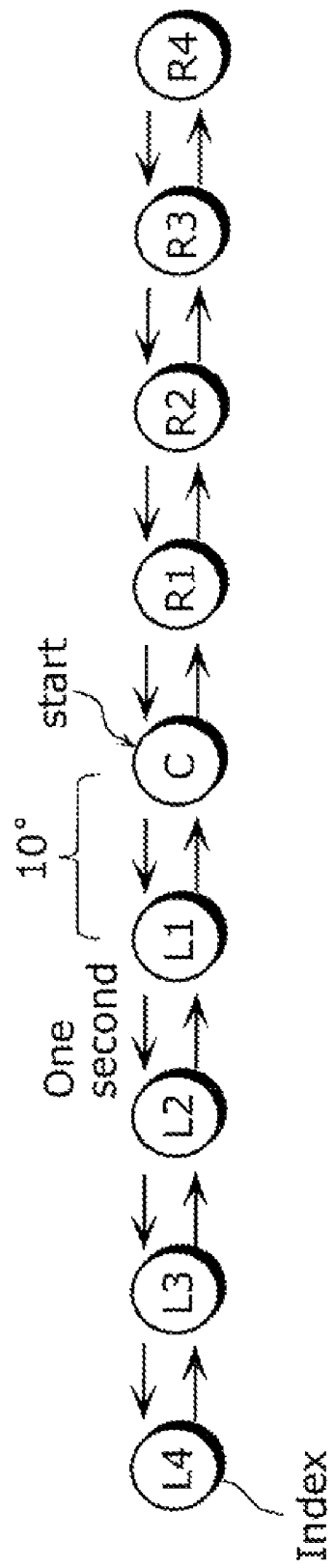
FIG. 66 is a diagram for explaining a drift in electro-oculography measurement.

The electro-oculography original signal measuring unit 110 is typically an electrode attached near an eye of the user. The way of attachment is not limited to a specific way. For example, as shown in FIG. 64A and FIG. 64B, the electrode A attached to the outer corner of the eye may be used in combination with the electrode B attached to the inner corner of the eye. Alternatively, as shown in FIG. 38A to FIG. 38D, the electrode may be attached above and/or below the eye. In addition, the electrodes may be attached above and below a temple.

The position at which to attach the electrode is not limited to a position near the eye, and it may be attached on the forehead or near an ear, for example.

The subtractor 120 subtracts a drift estimation signal estimated by the drift estimation processing unit 190, from the electro-oculography original signal including the user's electro-oculography signal measured by the electro-oculography original signal measuring unit 110, so as to output an electro-oculography signal that is the electro-oculography original signal from which the drift signal is removed.

The view capturing unit 150 captures a picture in the user's gaze direction (view picture). More specifically, the view capturing unit 150 captures a picture about the same as the picture actually being viewed by the user. The view capturing unit 150 is typically a camera attached to the user's head. The way of attachment is not limited to a specific way. For example, the view capturing unit 150 may be provided on a hat or a headband, or be incorporated into a headphone or eyeglasses.

The drift estimation processing unit 190 estimates the drift signal included in the electro-oculography original signal. Specifically, the drift estimation processing unit 190 shown in FIG. 1 includes a saccade detecting unit 130, an electro-oculography change amount calculating unit 140, a motion vector estimating unit 160, a drift change amount estimating unit 170, and a drift estimating unit 180.

The saccade detecting unit 130 detects a saccade signal from the electro-oculography signal. More specifically, the saccade detecting unit 130 determines, based on a past electro-oculography signal output from the subtractor 120, whether or not saccadic movement occurred in a predetermined time period in the past. When determining that saccadic movement occurred, the saccade detecting unit 130 outputs a saccade detection signal to the drift estimating unit 180.

It is to be noted that a saccade (saccadic eyeball movement) is eyeball movement caused to capture an object, which is projected on a peripheral retina having low resolution, with a central retinal fovea having high resolution, and it is known that the speed of the movement is very high at 100 to 500 (°/sec).

Figure 23:
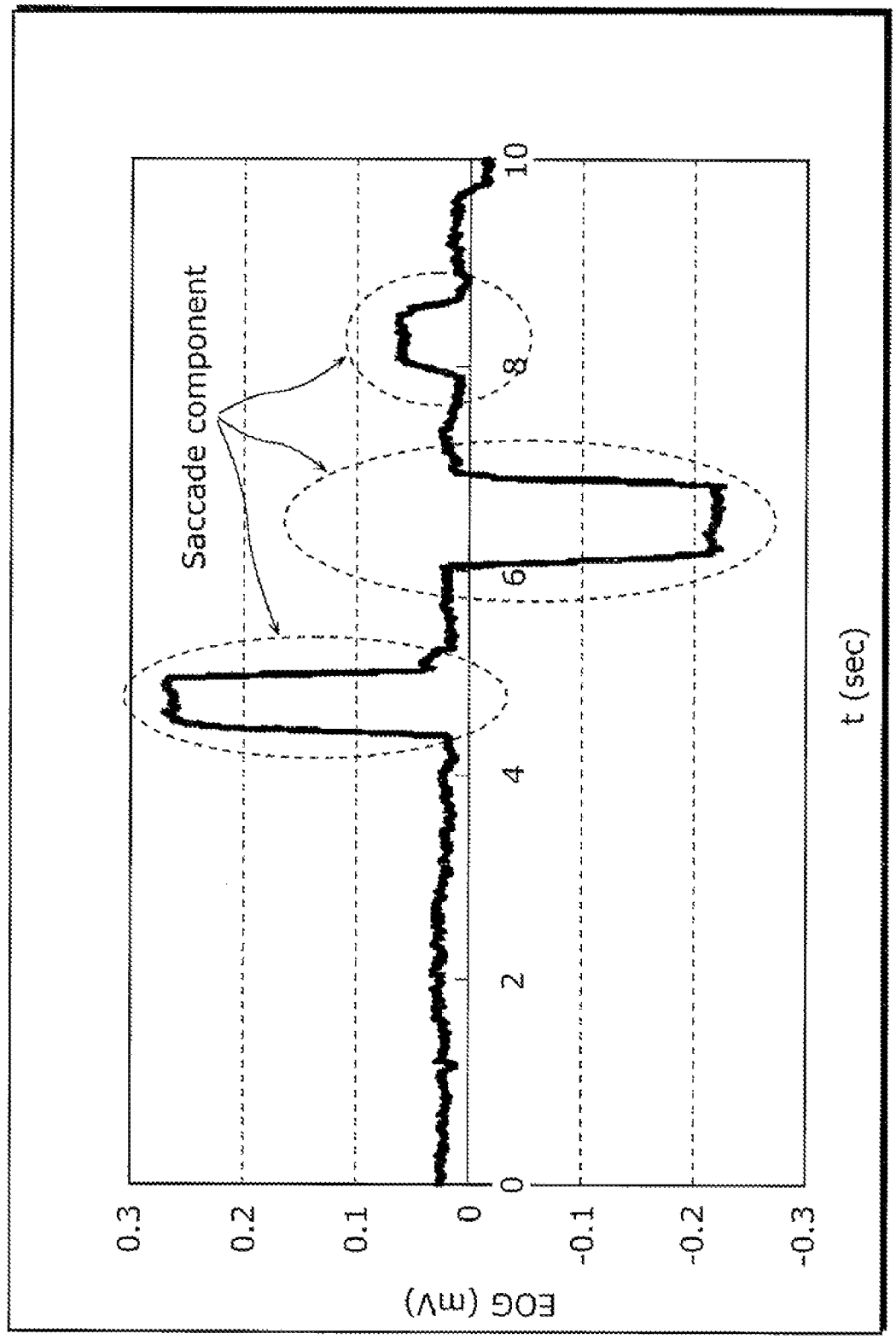
FIG. 23 is a diagram showing an example of an electro-oculography signal that includes a saccade signal.

FIG. 23 shows an example of a waveform of the electro-oculography signal including a saccade signal. In FIG. 23, each of the portions enclosed by dotted lines indicates a saccade. When a saccade occurs, after a rapid change occurs in potential, the eyeball stops moving for a certain period of time (fixation), and the potential returns to an initial potential level. This is an example case of moving an eyeball from an index A to an index B by saccade, and moving the eyeball again from the index B to the index A by saccade. Generally, a human obtains information from surroundings by repeating fixation for approximately 0.3 seconds and a saccade for several dozens of milliseconds.

As one of the methods of detecting a saccade signal from the electro-oculography signal as shown in FIG. 23, there is a method of applying each of maximum value filtering and minimum value filtering to the electro-oculography signal to calculate a difference between the resulting electro-oculography signals. The processing will be described later in detail.

Figure 30:
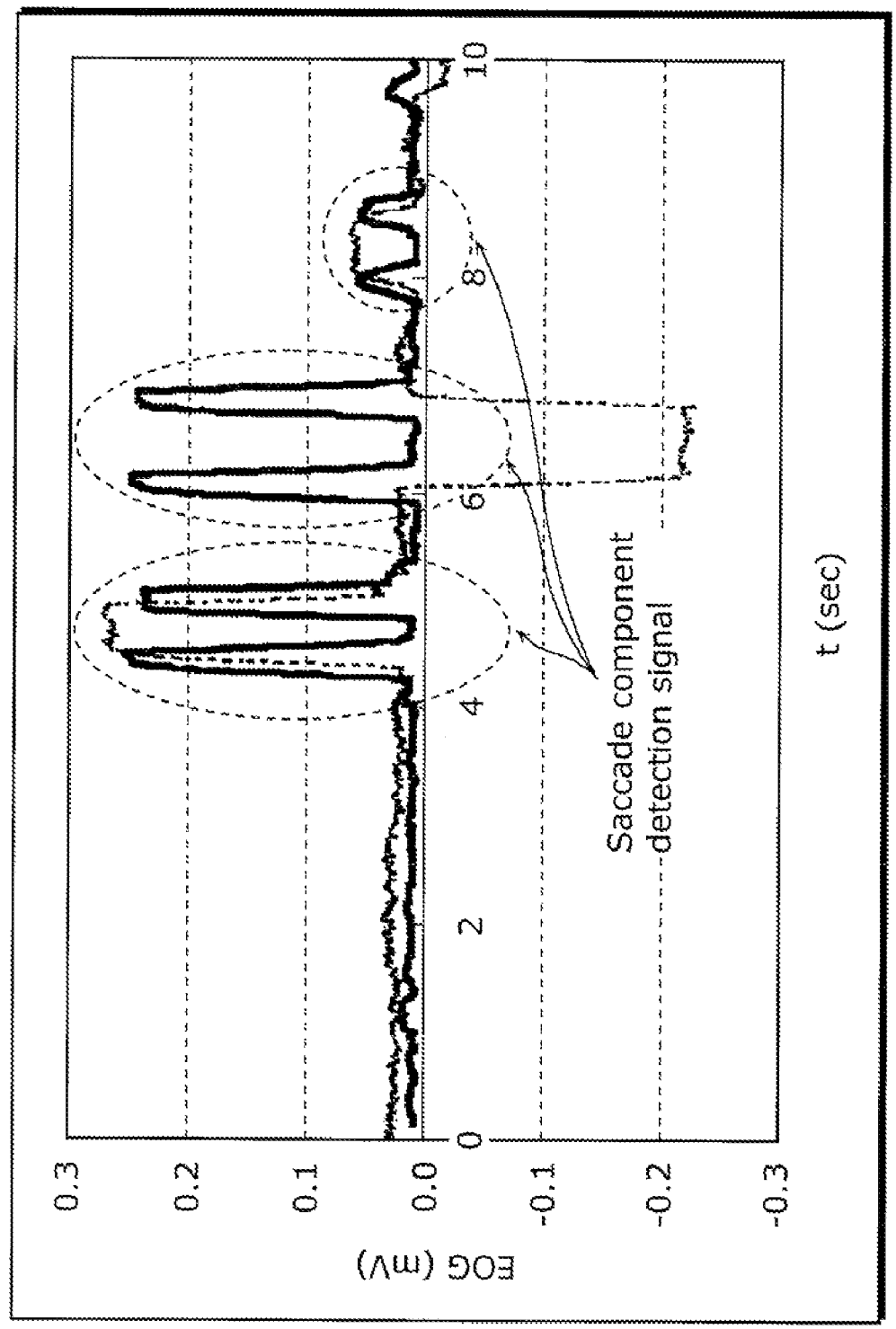
FIG. 30 is a diagram for explaining a saccade detection signal extracted from the electro-oculography signal in FIG. 23.

FIG. 30 shows an output signal obtained by applying the maximum value filtering and the minimum value filtering to the electro-oculography signal shown in FIG. 23. As shown in FIG. 30, the output signal includes a peak only when the saccade occurs.

The saccade detecting unit 130 determines, as a saccade signal indicating saccadic movement, a signal above a predetermined threshold among output signals, and outputs a saccade detection signal indicating that the saccade signal has been detected, to the drift estimating unit 180.

It is to be noted that, although the minimum value filter and the maximum value filter are used for detecting the saccade signal in the first embodiment, any technique, such as a high-pass filter, may be used as long as it detects a saccade.

The electro-oculography change amount calculating unit 140 calculates, based on a past electro-oculography signal output from the subtractor 120, an electro-oculography change amount indicating an amount of change in electro-oculogram over a predetermined time period in the past, and outputs the electro-oculography change amount to the drift change amount estimating unit 170. In addition, the electro-oculography change amount calculating unit 140 determines, using the calculated electro-oculography change amount, the presence or absence of a fixation, which is one form of eyeball movement. When detecting a fixation, the electro-oculography change amount calculating unit 140 outputs a fixation detection signal to the drift estimating unit 180. Specifically, the electro-oculography change amount calculating unit 140 determines that the user's eyeball was fixed in a predetermined time period in the past when the calculated electro-oculography change amount is below a predetermined threshold.

Figure 2:
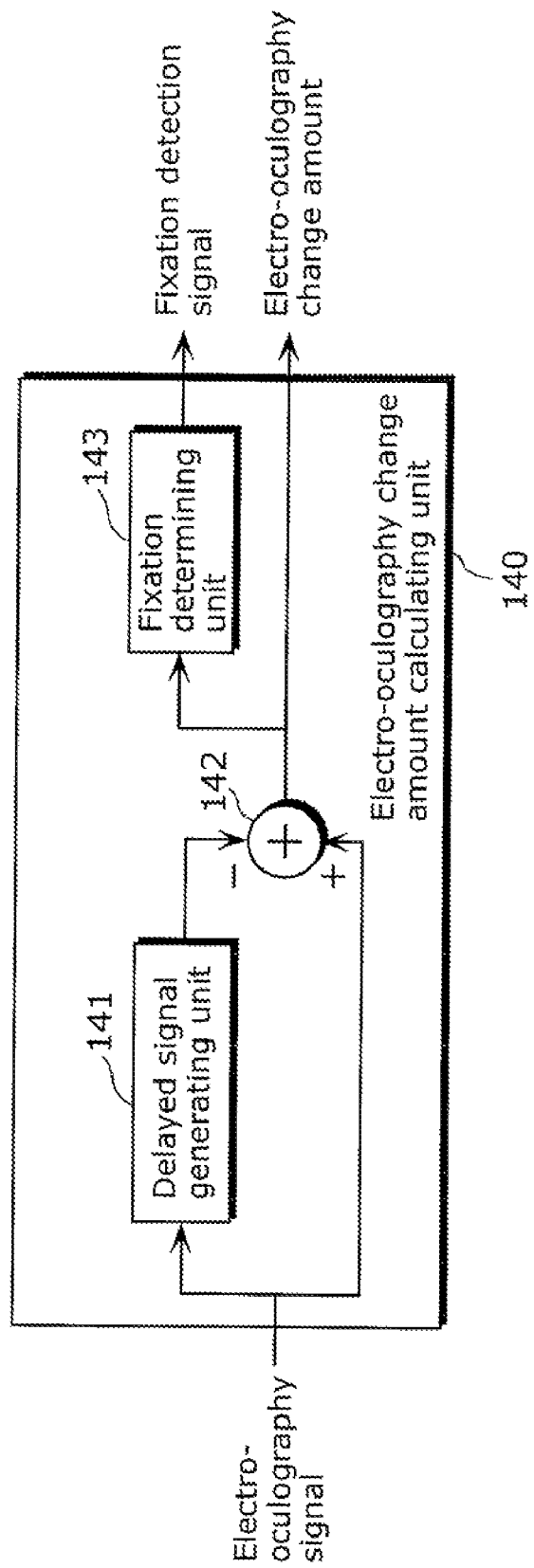
FIG. 2 is a block diagram of an electro-oculography change amount calculating unit in FIG. 1.

The electro-oculography change amount calculating unit 140 according to the first embodiment will be described with reference to FIG. 2. FIG. 2 is a diagram showing a configuration of the electro-oculography change amount calculating unit 140 according to the first embodiment. The electro-oculography change amount calculating unit 140 includes a delayed signal generating unit 141, a subtractor 142, and a fixation determining unit 143.

The delayed signal generating unit 141 delays an electro-oculography signal for a predetermined time period to output a delayed signal. The electro-oculography signal which is input into the electro-oculography change amount calculating unit 140 is branched into two signals. One of the branched signals is input into the subtractor 142 as the delayed signal via the delayed signal generating unit 141, and the other is directly input into the subtractor 142. Then, the subtractor 142 subtracts the delayed signal from the electro-oculography signal to output an electro-oculography change amount.

Processing of the delayed signal generating unit 141 will be described next. The delayed signal generating unit 141 applies the following processing to an electro-oculography signal EOG (t) which is an electro-oculography signal at a time t.

$$EOGdelay(t) = EOG(t-1)$$

Here, EOGdelay (t) is an electro-oculography signal after the delay processing (delayed signal). Application of the above-described delay processing to an electro-oculography signal produces a delayed signal. Then, the subtractor 142 subtracts the delayed signal EOGdelay (t) from the electro-oculography signal EOG (t) at a time t so as to output an electro-oculography change amount ΔEOG (t).

When the electro-oculography change amount ΔEOG (t) satisfies the following expression, the fixation determining unit 143 determines that the fixation detection signal has been generated, and thus sets the fixation detection signal high.

$$|\Delta EOG(t)| < TH\_FIX$$

TH_FIX represents a predetermined threshold. When the above expression is not satisfied, the fixation detection signal is set low.

It is to be noted that although in the first embodiment, the delayed signal generating unit 141 is provided to generate the delayed signal of the electro-oculography signal, and the delayed signal is subtracted from the electro-oculography signal to calculate the electro-oculography change amount, an electro-oculography signal EOG (t−1), which is an electro-oculography signal at a time t−1, may be constantly stored in a memory to calculate the electro-oculography change amount ΔEOG (t).

The motion vector estimating unit 160 estimates a motion vector of a moving object included in the picture captured by the view capturing unit 150. The motion vector indicates a motion of the moving object in a predetermined time period in the past. More specifically, the motion vector estimating unit 160 divides the view picture, which is output from the view capturing unit 150, into n×m blocks (hereinafter, the (n−1) and (m−1)th block is referred to as (n−1, m−1)), and estimates a motion vector on a block-by-block basis. A specific example of motion vector estimation will be described with reference to FIG. 3A and FIG. 3B.

Figure 3A:
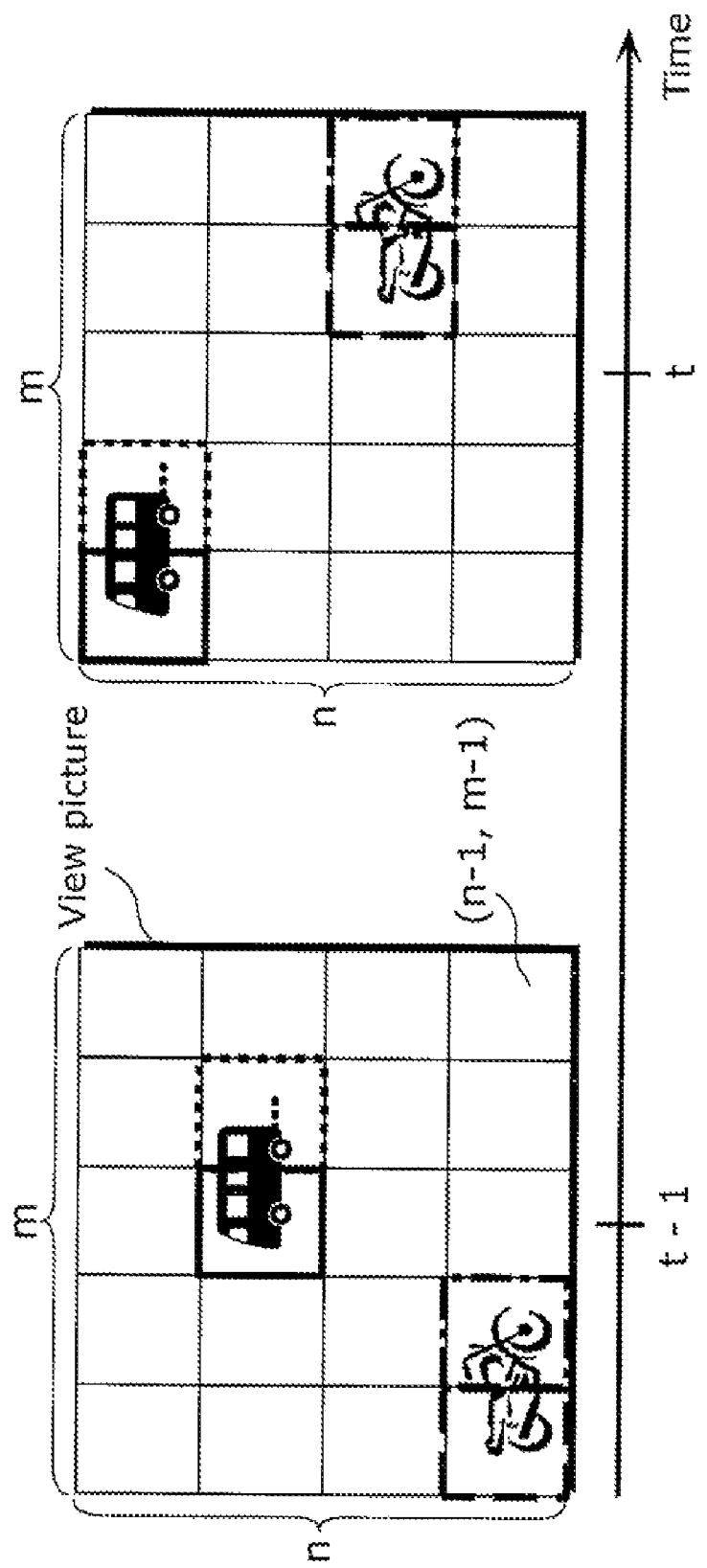
FIG. 3A is a diagram showing an example of view pictures at a time t and a time t−1.

Assuming that the left side of FIG. 3A is a view picture at a time t−1, and the right side of FIG. 3A is a view picture at a time t, the following shows an example of estimating a motion vector at the time t with reference to the view picture at the time t−1. More specifically, the motion vector according to an implementation of the present invention is a vector indicating the position of one of the blocks constituting a first picture captured at the time t (a first time point), in a second picture captured at the time t−1 (a second time point preceding the first time point).

Figure 3B:
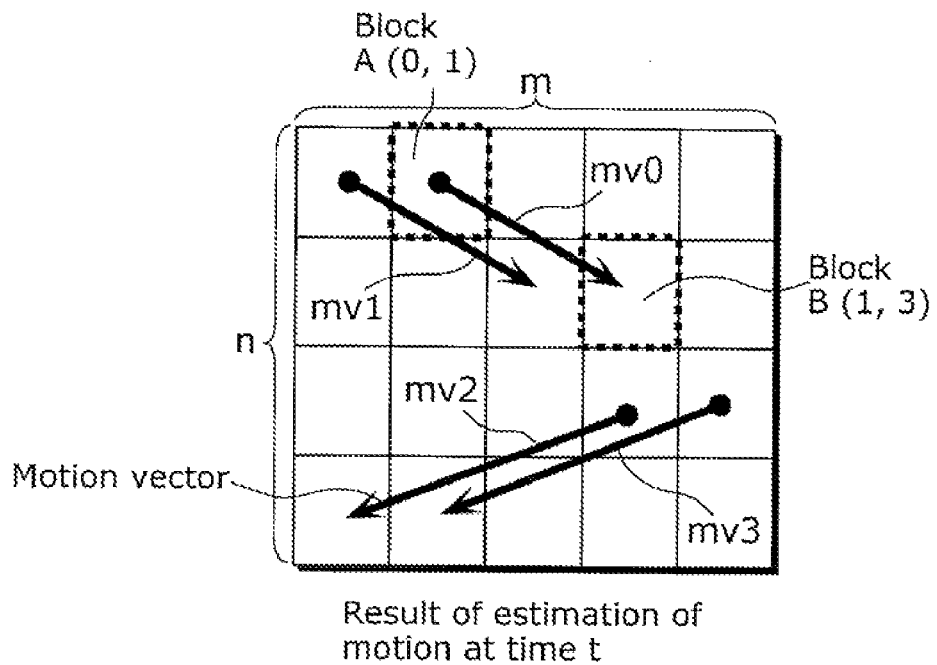
FIG. 3B is a diagram showing an example of motion vectors at the time t in the view picture shown in FIG. 3A.

First, the view picture at the time t is divided into n×m blocks. Then, for each block (target block) of the divided view picture at the time t, pixel value matching is performed with the view picture at the time t−1, and a difference in pixel position between the target block and the block with the smallest matching cost among the blocks in the view picture at the time t−1 is determined as the motion vector of the target block. As the matching cost, SAD (Sum of Absolute Differences) or the like is used. FIG. 3B shows an example of a result of motion vector estimation at the time t. As shown in FIG. 3B, motion vectors are estimated in regions which include a moving object from the time t−1 to the time t.

It is to be noted that although the first embodiment has shown an example of a block-matching-based method as the motion vector estimation method, any technique may be used as long as it estimates a motion, such as the Lucas-Kanade method. In addition, although the picture at the time t−1 is used as the reference picture, it is also possible to refer to a picture at a time before the time t−1 or after the time t.

Figure 4:
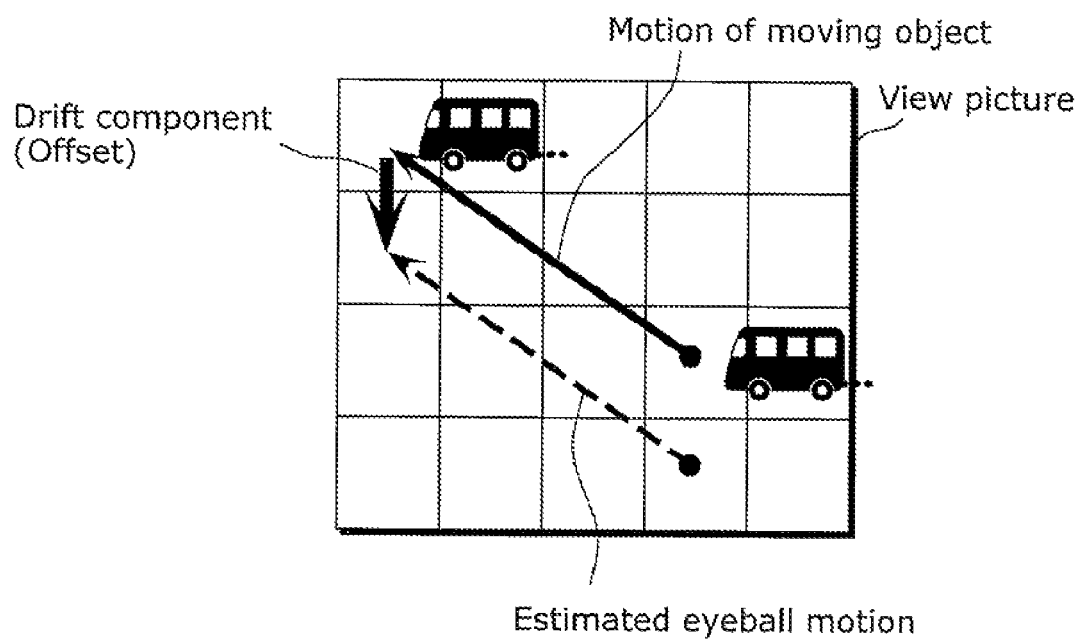
FIG. 4 is a diagram showing an example of a drift component estimated according to the first embodiment.

The drift change amount estimating unit 170 detects occurrence of tracking movement, which is one form of eyeball movement, using an amount of change in motion vector in a view picture and an electro-oculography change amount. The drift change amount estimating unit 170 then estimates, as a drift component (drift change amount), a difference (hereinafter referred to as offset) between a motion-vector-generated position and an estimated eyeball position at the time of detecting the tracking movement. More specifically, as shown in FIG. 4, the drift change amount estimating unit 170 estimates a drift change amount over a predetermined time period in the past, assuming that a change in the gaze direction indicated by the electro-oculography change amount follows the motion of the moving object indicated by the corresponding motion vector.

Figure 5:
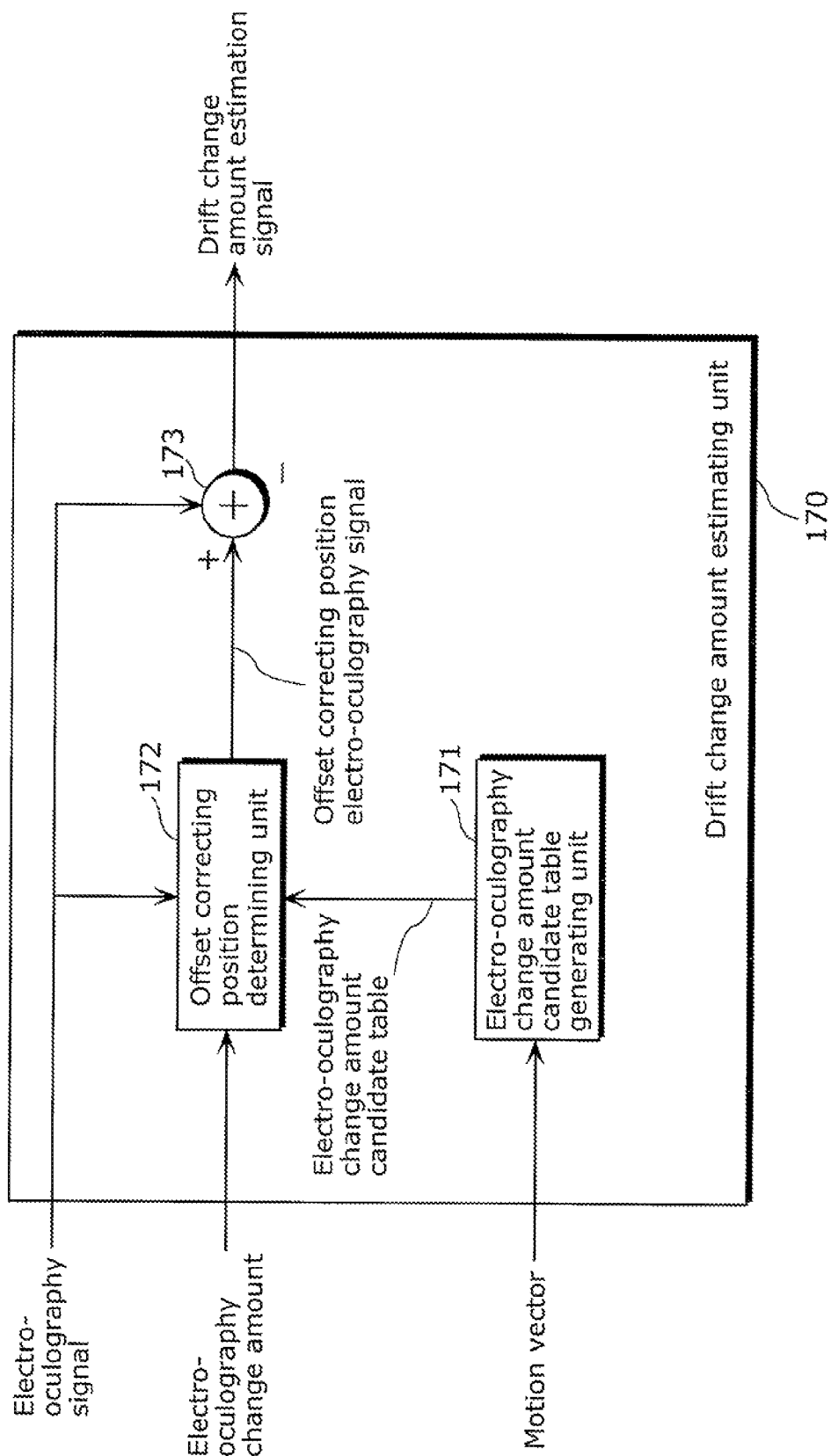
FIG. 5 is a block diagram of a drift change amount estimating unit in FIG. 1.

The drift change amount estimating unit 170 according to the first embodiment will be described with reference to FIG. 5. FIG. 5 is a diagram showing a configuration of the drift change amount estimating unit 170 according to the first embodiment. The drift change amount estimating unit 170 according to the first embodiment includes an electro-oculography change amount candidate table generating unit 171, an offset correcting position determining unit 172, and a subtractor 173.

The electro-oculography change amount candidate table generating unit 171 converts each motion vector, which is estimated on a block-by-block basis and output from the motion vector estimating unit 160, into a motion-vector-equivalent electro-oculography change amount, so as to generate an electro-oculography change amount candidate table for determination of an offset correcting position.

For example, a motion vector mv0 of a block (0, 1) as shown in FIG. 3B is converted into a motion-vector-equivalent electro-oculography change amount generated assuming that the user's eyeball has moved along the motion vector mv0 (in this example, assuming that the eyeball has moved in the direction opposite to the motion vector direction). Specifically, as for the motion vector mv0, in order to show that the moving object has moved from a block B (1, 3) to a block A (0, 1) between the time t−1 and the time t, an electro-oculography change amount which is generated when the eyeball has likewise moved from the block B to the block A is calculated as the motion-vector-equivalent electro-oculography change amount.

The calculation method is not limited to a specific method. For example, it is possible to calculate the motion-vector-equivalent electro-oculography change amount using, as shown in FIG. 6, a generated-electro-oculogram table prepared in advance, e.g. before the measuring experiment. The generated-electro-oculogram table shown in FIG. 6 is a table in which a gaze direction of the user and an electro-oculogram generated in that gaze direction are associated with each other.

In the example case of the first embodiment where the generated-electro-oculogram table shown in FIG. 6 is used, −100 μV (generated electro-oculogram at the block A)−150 μV (generated electro-oculogram at the block B)=−250 μV is the motion-vector-equivalent electro-oculography change amount for the motion vector mv0. Motion-vector-equivalent electro-oculography change amounts are calculated also for the other motion vectors in the same manner, and are transmitted to the offset correcting position determining unit 172 as an electro-oculography change amount candidate table as shown in FIG. 7.

It is to be noted that although in the first embodiment, the motion vector conversion is performed using the generated-electro-oculogram table as shown in FIG. 6, the electro-oculography change amount may be calculated using a linear equation (for example, Expression 1 below) assuming that an eyeball position and a generated electro-oculogram have a linear relationship.

In addition, although it is stated above that the generated-electro-oculogram table as shown in FIG. 6 is prepared in advance, e.g. before the measuring experiment, it may be regularly updated during the measurement.

The offset correcting position determining unit 172 determines an offset correcting position using an electro-oculography signal, an electro-oculography change amount, and an electro-oculography change amount candidate table, and outputs a corresponding electro-oculography signal.

Specifically, the offset correcting position determining unit 172 first performs matching comparison between an electro-oculography change amount and each of electro-oculography change amounts which correspond to the block positions on a one-to-one basis and are indicated in the electro-oculography change amount candidate table. Then, when the matching cost is equal to or below a certain value, the offset correcting position determining unit 172 determines that an amount of change in the motion of the eyeball and an amount of change in the motion of the moving object are similar, that is, there is a possibility that the user's eyeball is tracking the moving object at the target block position, and thus determines that block position as an offset correcting position candidate.

In other words, the offset correcting position determining unit 172 extracts, from among a plurality of motion vectors estimated by the motion vector estimating unit 160, one or more motion vectors having a difference equal to or below a predetermined threshold between a corresponding motion-vector-equivalent electro-oculography change amount and the electro-oculography change amount calculated by the electro-oculography change amount calculating unit 140. Then, the respective start positions of the extracted one or more motion vectors are determined as offset correcting position candidates.

Next, electro-oculograms generated at the determined offset correcting position candidates are calculated using the generated-electro-oculogram table in FIG. 6. Subsequently, matching comparison is performed between the calculated electro-oculograms and the electro-oculography signal output from the subtractor 120 at the time t. Then, the offset correcting position candidate having a matching cost which is equal to or below a certain value and is smallest is determined as the offset correcting position. Such processing makes it possible to select, from among a plurality of offset correcting position candidates, the correcting position closest to the position indicated by the electro-oculography signal calculated by the electro-oculography change amount calculating unit 140, thereby enabling suppression of an influence of false drift detection.

It is to be noted that although the first embodiment shows an example of using a square difference as the matching cost, a square-root of a square difference, an absolute difference, or the like may be used.

Figure 8:
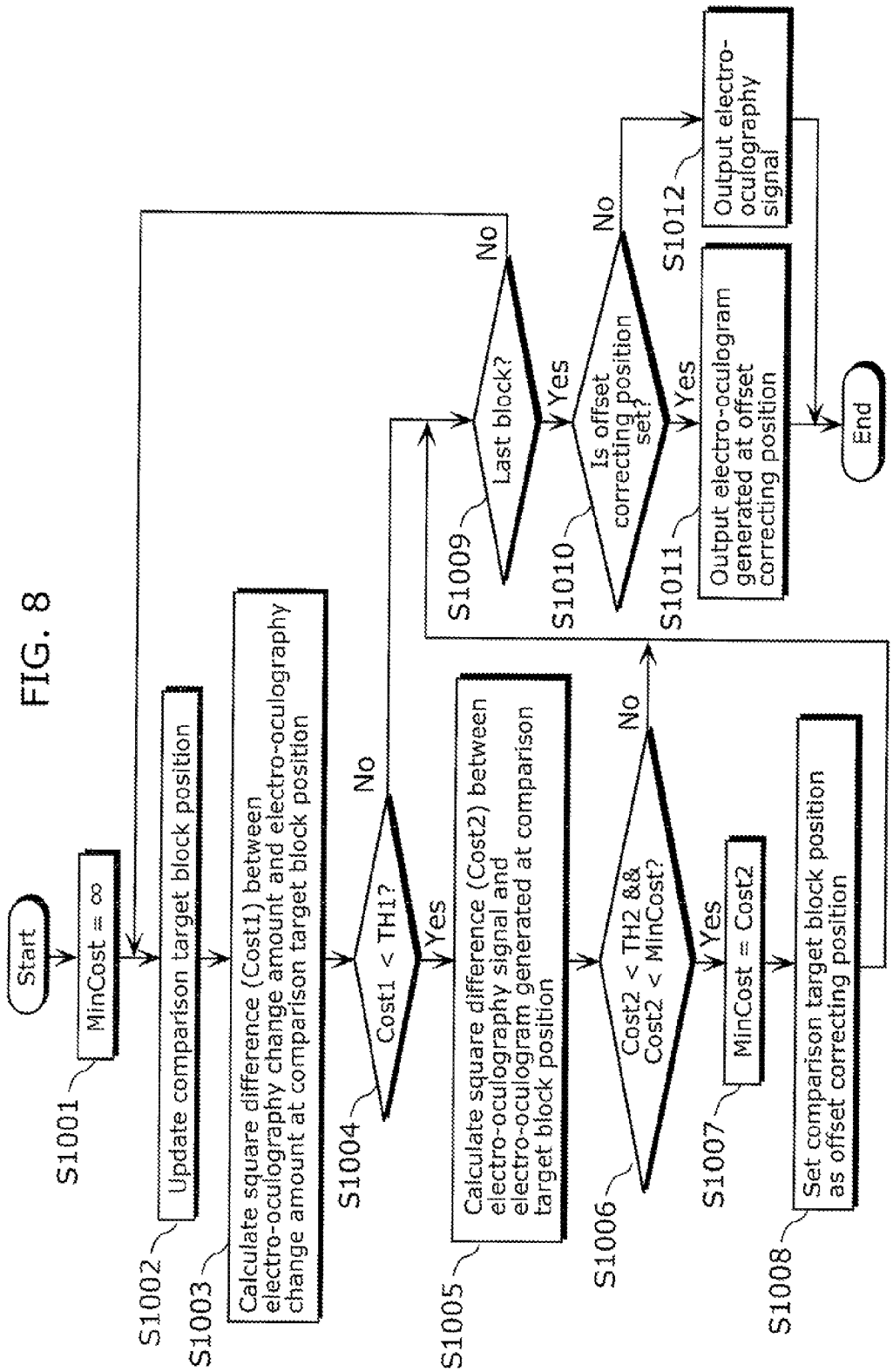
FIG. 8 is a flow chart showing an operation of an offset correcting position determining unit according to the first embodiment.

FIG. 8 shows a processing procedure of the offset correcting position determining unit 172. First, a variable MinCost is initialized (S1001). Next, a comparison target block position, which is a target block position for the electro-oculography change amount comparison, is updated (S1002). Although the comparison order is not limited to a specific order, the comparison may be performed in an order starting from the block (0, 0), the block (0, 1), the block (0, 2), . . . the block (1, 0), . . . , and the block (3, 4), for example.

Subsequently, a square difference Cost1, which is a matching cost, is calculated using an electro-oculography change amount and a motion-vector-equivalent electro-oculography change amount which is generated at the comparison target block position and is indicated in the electro-oculography change amount candidate table (S1003). Then, it is determined whether or not the calculated square difference Cost1 is smaller than a preset threshold TH1 (S1004).

When the comparison result is true, the comparison target block position is determined as an offset correcting position candidate, and a square difference Cost2 between an electro-oculogram generated at the comparison target block position and the electro-oculography signal calculated by the electro-oculography change amount calculating unit 140 is calculated (S1005). Then, it is determined whether or not the square difference Cost2 is smaller than a preset threshold TH2 and is smallest (S1006). When the result is true, MinCost is updated (S1007), and the comparison target block position is set as the offset correcting position (S1008).

When the comparison is finished for all the blocks (S1009), it is determined whether or not an offset correcting position has been finally set, that is, whether or not tracking movement has been detected (S1010). When the result is true, the electro-oculogram generated at the offset correcting position is output (S1011). On the other hand, when the result is false, the electro-oculography signal is output without correction, and the processing is terminated (S1012).

As an example of the offset correcting position determination, in the case where, for example: the electro-oculography signal output from the subtractor 120 at the time t is −50 µV; the electro-oculography change amount between the time t−1 and the time t is −300 µV; and an electro-oculography change amount candidate table as shown in FIG. 7 is given, following the processing procedure in FIG. 8 results in selecting, as the offset correcting position candidates, of the block positions (0, 0) and (0, 1) at which the square difference between corresponding electro-oculography change amounts is small. Then, the block position (0, 1) at which the generated electro-oculogram has the smallest least-square value is finally determined as the offset correcting position, and the electro-oculogram generated at the block position (0, 1) shown in FIG. 6 is output as an electro-oculogram corresponding to the offset correcting position. (Note that the least-square value is a value calculated using the least square method.)

Figure 9:
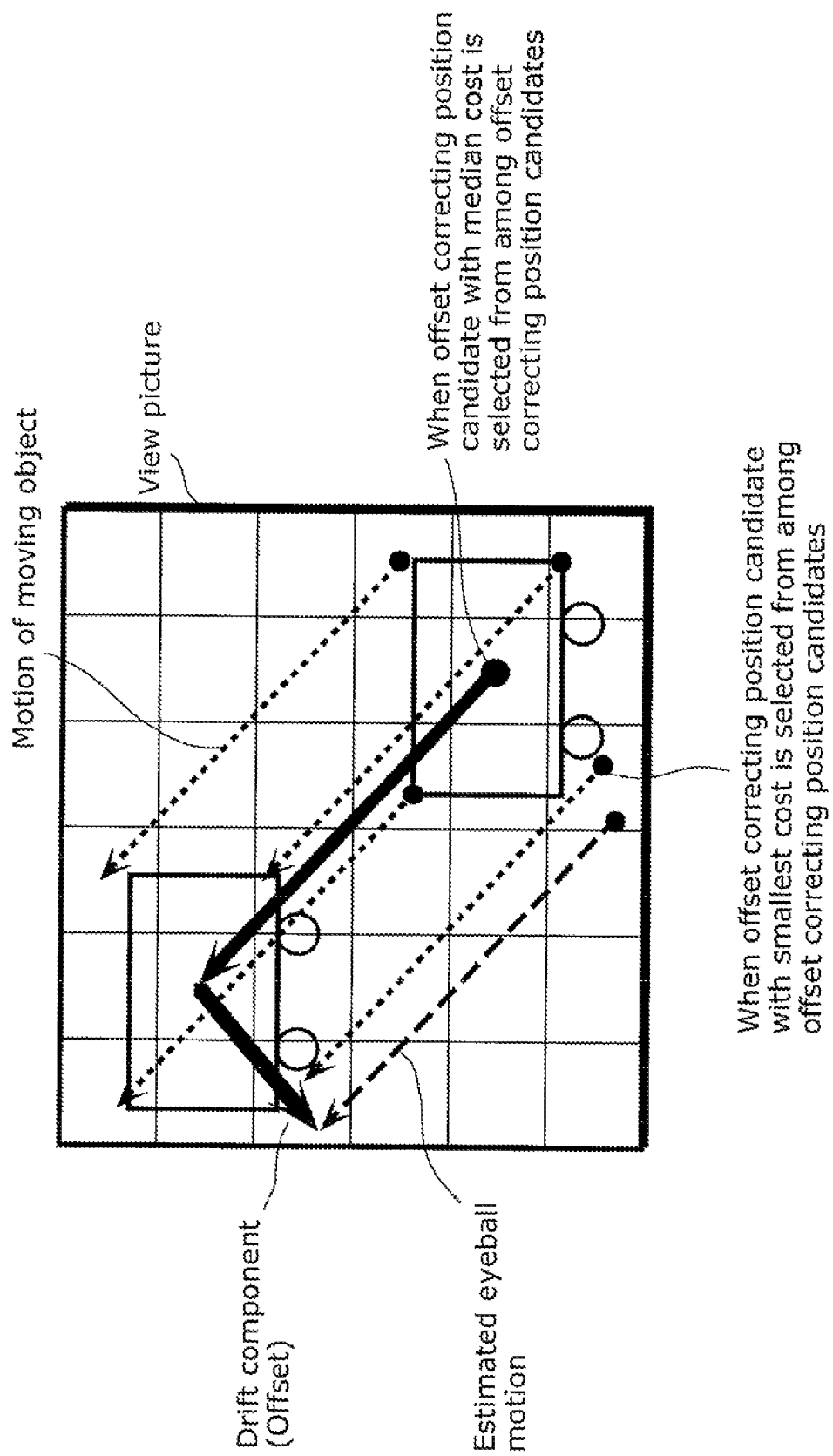
FIG. 9 is a diagram showing an example of a drift component which is estimated when selecting a median cost in determining an offset correcting position according to the first embodiment.

It is to be noted that although in the first embodiment, the position at which the square difference Cost2 between the electro-oculogram generated at the comparison target block position and the electro-oculography signal at the time t is the smallest is determined as the offset correcting position, it does not necessarily have to be the smallest. For example, for each of offset correcting position candidates, a square difference Cost2 between a corresponding generated electro-oculogram and an electro-oculography signal at the time t is calculated. Then, the offset correcting position candidate having the median value of the calculated square differences Cost2 may be selected as the offset correcting position. This allows correction to the center of the moving object as shown in FIG. 9.

The subtractor 173 subtracts the electro-oculography signal output from the subtractor 120 at the time t from the electro-oculogram corresponding to the offset correcting position output from the offset correcting position determining unit 172, so as to generate a drift change amount estimation signal.

The drift estimating unit 180 adds the drift change amount estimation signal at a time t, which is output from the drift change amount estimating unit 170, to a drift estimation signal at a time t−1 according to the saccade detection signal and the fixation detection signal, so as to calculate a drift estimation signal at the time t. Specifically, the drift estimation signal is updated only when the eyeball movement is neither a saccade nor a fixation.

Figure 10:
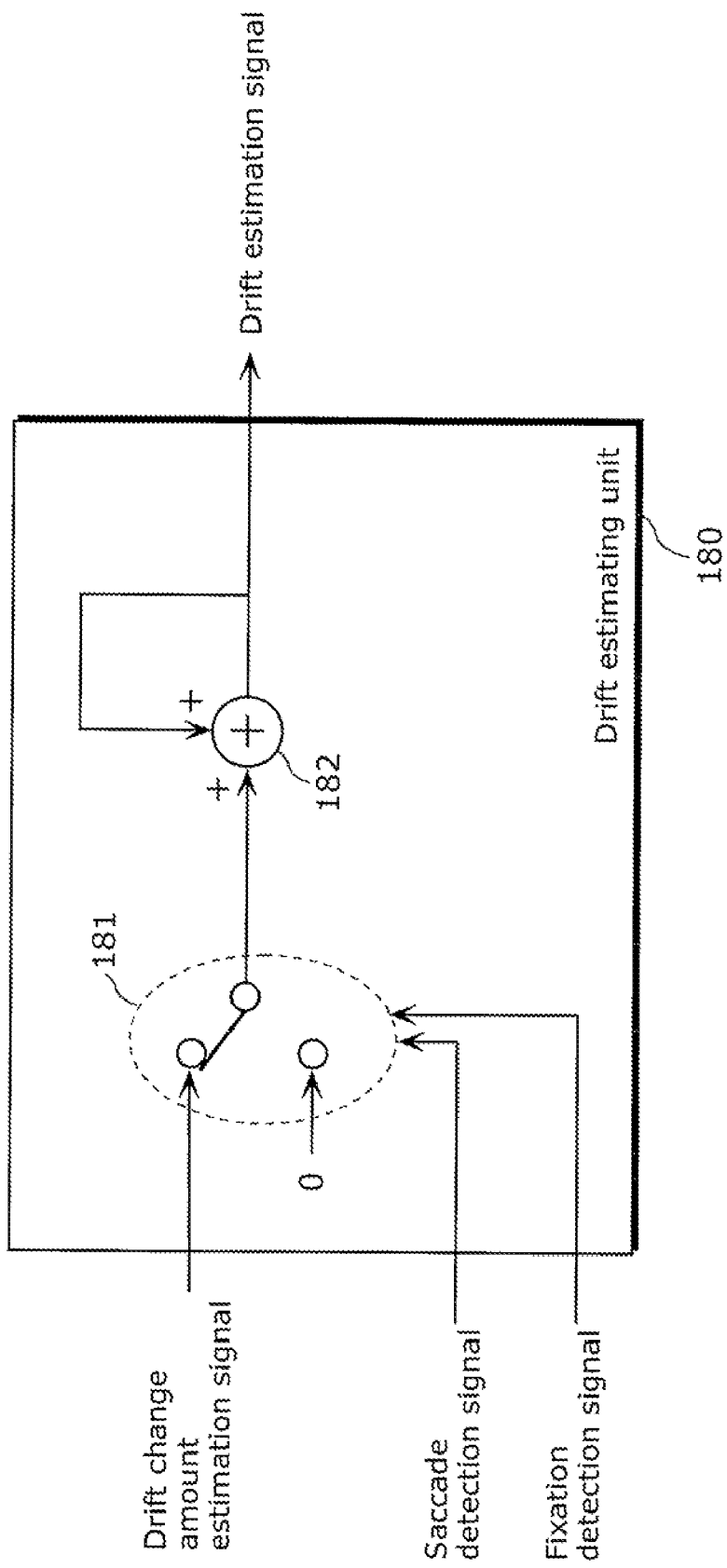
FIG. 10 is a block diagram of a drift estimating unit in FIG. 1.

With reference to FIG. 10, the drift estimating unit 180 according to the first embodiment will be described. FIG. 10 is a diagram showing a configuration of the drift estimating unit 180 according to the first embodiment. The drift estimating unit 180 includes a switch 181 and an adder 182.

The switch 181 performs switching to change what is to be output to the adder 182, according to the saccade detection signal provided from the saccade detecting unit 130 and the fixation detection signal provided from the electro-oculography change amount calculating unit 140. Specifically, when the saccade detection signal is high (when a saccade is detected) or the fixation detection signal is high (when a fixation is detected), the switching is performed so that 0 is output. On the other hand, when both the saccade detection signal and the fixation detection signal are low (neither a saccade nor fixation is detected), the switching is performed so that the drift change amount estimation signal provided from the drift change amount estimating unit 170 is output.

Such a switching operation allows the drift estimation signal to be updated only when neither a saccade nor fixation is detected, that is, only when the eyeball is performing tracking movement. This is because the drift change amount is estimated based on the premise that the user's gaze tracks the motion of the moving object. That is to say, a drift change amount estimation signal when the eyeball is performing movement other than tracking (that is, when the eyeball is performing a saccade or a fixation) does not accurately represent a drift component, and thus such a drift change amount estimation signal is not added to a past drift estimation signal.

The adder 182 adds up an output signal at the time t (0 or a drift change amount estimation signal), which is provided via the switch 181, and a drift estimation signal at the time t−1, which is provided from the adder 182, so as to generate a drift estimation signal at the time t.

According to the configuration of the first embodiment described above, (i) tracking movement is detected based on a motion vector in a view picture and an electro-oculography change amount, (ii) a difference between a motion-vector-generated position and an estimated eyeball position at the time of detecting the tracking movement is estimated as a drift component, and (iii) the drift component is subtracted from the user's electro-oculography original signal which has been measured. This makes it possible to output an electro-oculography signal from which an influence of a drift is removed.

In addition, a saccade and fixation are detected from a past electro-oculography signal, and the drift estimation signal is not updated when a saccade or fixation is detected. This allows reduction in false drift detection.

It is to be noted that although the example in the first embodiment has shown the case where the electro-oculography original signal measured from the user is a one-channel signal, it is unnecessary to limit the number of channels to a specific number. It is also possible to increase the number of channels so that a drift estimation signal is estimated from each of multi-channel electro-oculography original signals to thereby measure multi-channel electro-oculography signals. In that case, the matching cost Cost1 in the processing procedure of the offset correcting position determining unit 172 shown in FIG. 8 is extended to a sum of square differences each of which is calculated on a channel-by-channel basis between an electro-oculography change amount and a motion-vector-equivalent electro-oculography change amount at a comparison target block position. Likewise, Cost2 is extended to a sum of square differences each of which is calculated on a channel-by-channel basis between an electro-oculogram and an electro-oculogram generated at a comparison target block position. Such an increase in the number of channels further reduces false detection of the offset correcting position.

Second Embodiment

Figure 11:
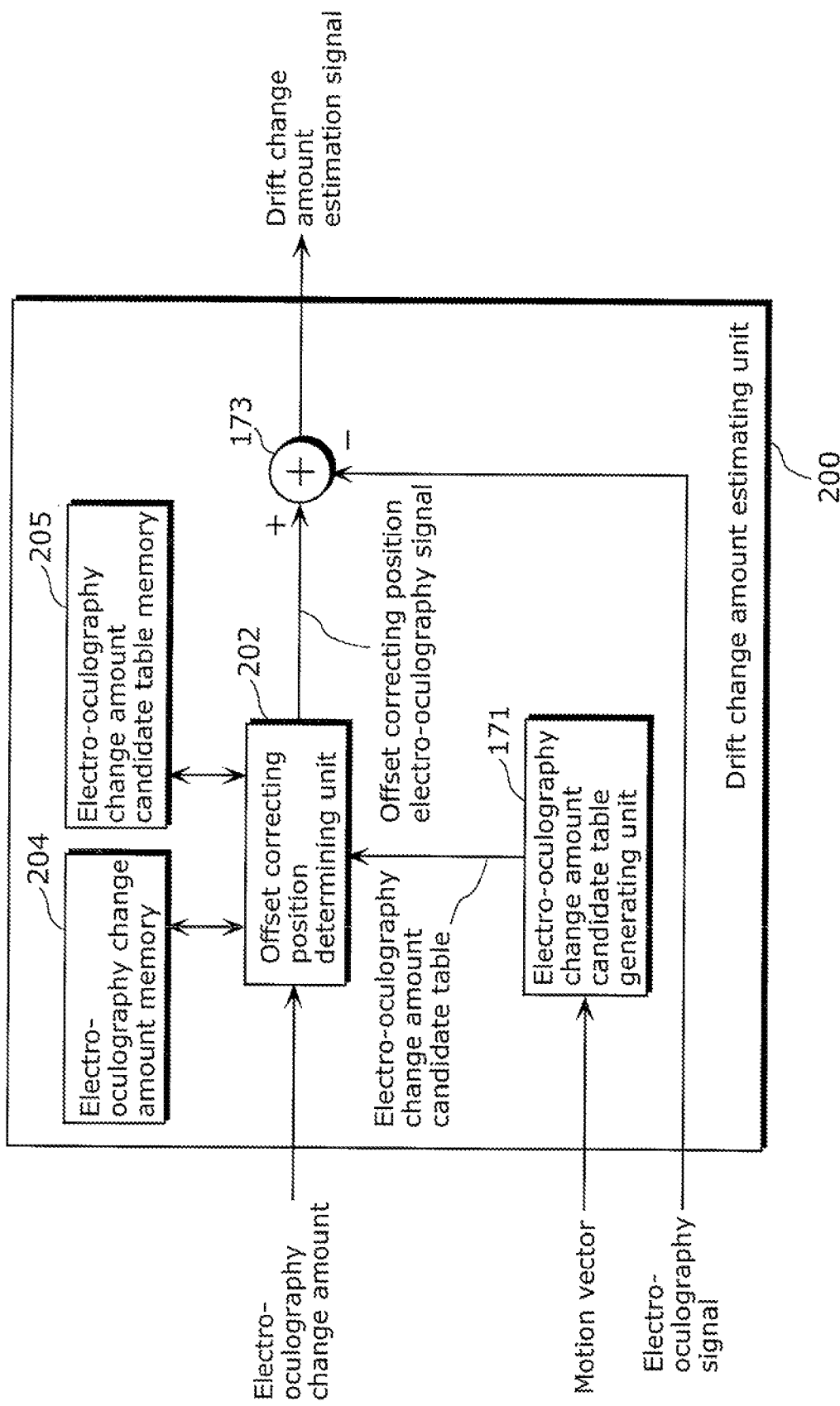
FIG. 11 is a block diagram of a drift change amount estimating unit according to a second embodiment.

FIG. 11 is a block diagram showing a configuration of a drift change amount estimating unit 200 according to a second embodiment of the present invention.

The drift change amount estimating unit 200 according to the second embodiment includes the electro-oculography change amount candidate table generating unit 171, an offset correcting position determining unit 202, an electro-oculography change amount memory 204, an electro-oculography change amount candidate table memory 205, and the subtractor 173. That is, the second embodiment is different from the first embodiment in newly including, in the drift change amount estimating unit 170 shown in FIG. 5, the electro-oculography change amount memory 204, the electro-oculography change amount candidate table memory 205, and the offset correcting position determining unit 202.

The constituent elements in FIG. 11 which are the same as those in FIG. 5 have already been described, and thus the same reference numerals are assigned and the descriptions thereof will not be repeated.

The electro-oculography change amount memory 204 and the electro-oculography change amount candidate table memory 205 store electro-oculography change amounts and electro-oculography change amount candidate tables, respectively, which correspond to a predetermined time period and are input from the offset correcting position determining unit 202.

The offset correcting position determining unit 202 determines an offset correcting position using the electro-oculography change amounts and the electro-oculography change amount candidate tables corresponding to the predetermined time period, which are respectively stored in the electro-oculography change amount memory 204 and the electro-oculography change amount candidate table memory 205.

Figure 12:
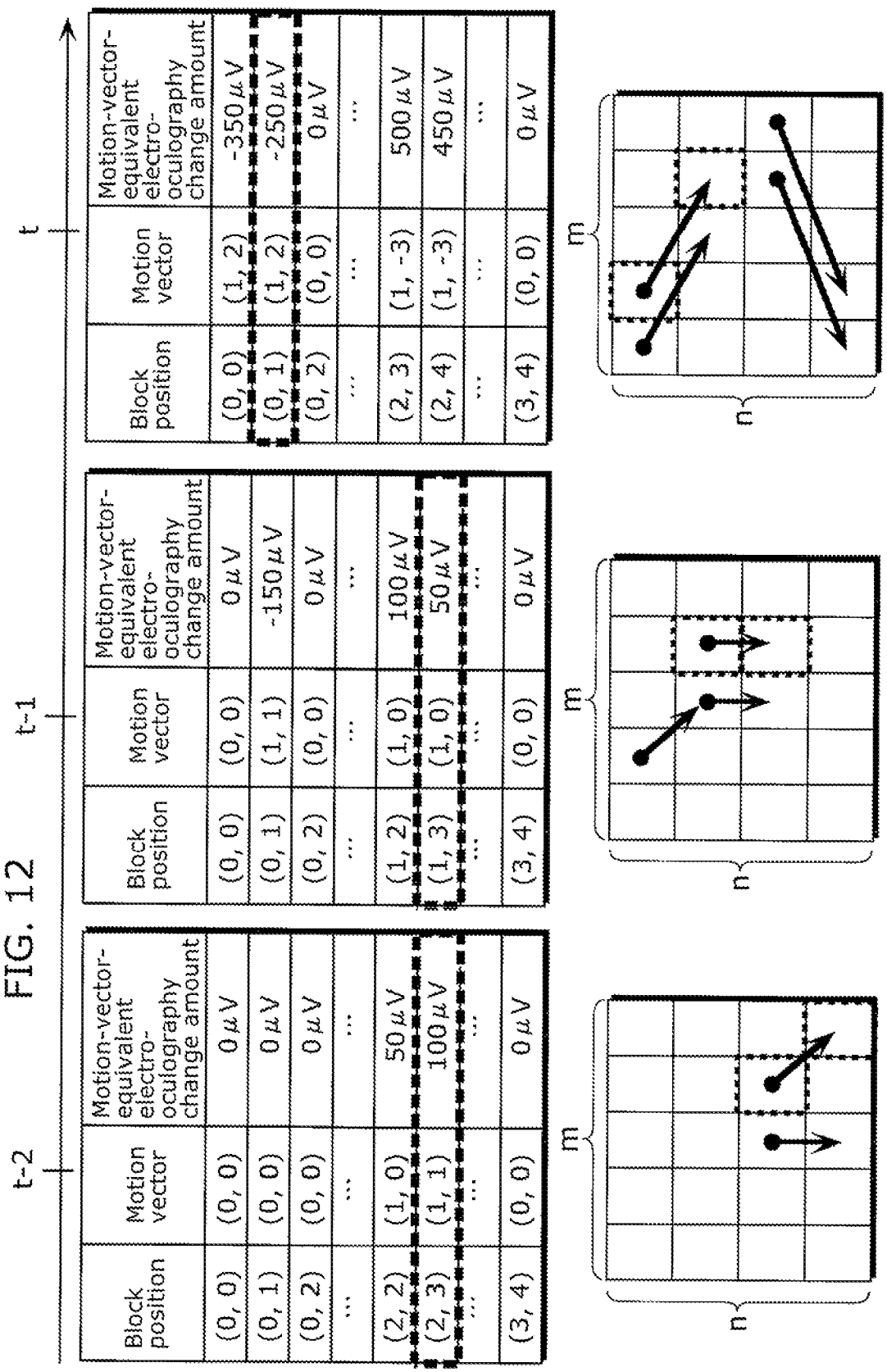
FIG. 12 is a diagram showing an example of electro-oculography change amount candidate tables between a time t−2 and a time t according to the second embodiment.

A method of determining the offset correcting position will be described using a specific example in FIG. 12. FIG. 12 shows electro-oculography change amount candidate tables and corresponding motion vectors at a time t (a first time point), a time t−1 (a second time point), and a time t−2 (a third time point).

The offset correcting position determining unit 202 first determines, using the electro-oculography change amount candidate tables at the time t, the time t−1, and the time t−2, a temporal trajectory of a moving object, by which the motion vector of each block at the time t is caused.

For example, a motion vector (1, 2) is generated from the block (0, 1) at the time t, indicating that there was a moving object at the block (1, 3) at the time t−1. Likewise, there is a motion vector (1, 0) at the block (1, 3) at the time t−1, indicating that there was a moving object at the block (2, 3) at the time t−2. This shows that the moving object at the block (0, 1) at the time t had moved from the block (2, 3) to (1, 3), and then to (0, 1) between the time t−2 and the time t, and the electro-oculography change amount candidate tables show that electro-oculography change amounts corresponding to these motions are 100 µV, 50 µV, and −250 µV.

Figure 13A:
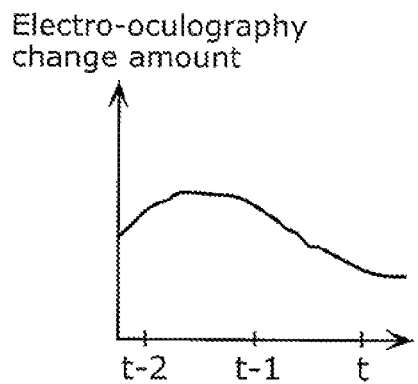
FIG. 13A is a diagram showing an example of an electro-oculography change amount vector according to the second embodiment.
Figure 13B:
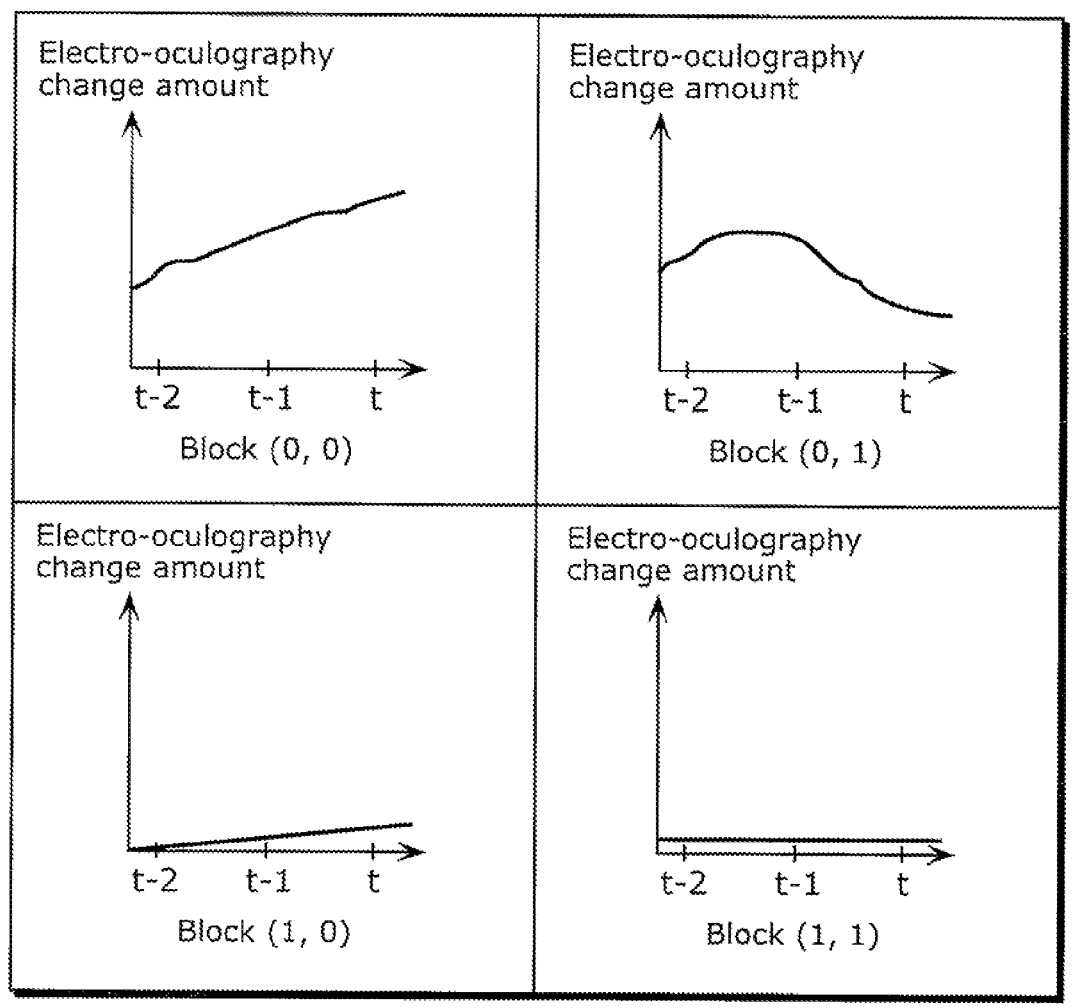
FIG. 13B is a diagram showing an example of electro-oculography change amount vectors according to the second embodiment.

By applying the same processing to all the block positions, electro-oculography change amount candidate vectors between the time t−2 and the time t as shown in FIG. 13B can be obtained. Each electro-oculography change amount candidate vector shown in FIG. 13B represents temporal variations (transition) in motion-vector-equivalent electro-oculography change amounts corresponding to a combination of motion vectors at the time points (the time t, the time t−1, and the time t−2) that represent motions with respect to the same block.

Next, an electro-oculography change amount vector as shown in FIG. 13A is determined using an electro-oculography change amount between the time t−2 and the time t, which is stored in the electro-oculography change amount memory 204. The electro-oculography change amount vector shown in FIG. 13A represents temporal variations (transition) in the electro-oculography change amounts between the time t−2 and the time t, which is calculated by the electro-oculography change amount calculating unit 140.

Then, the offset correcting position is determined according to a processing procedure in FIG. 14, using the determined electro-oculography change amount vector and the electro-oculography change amount candidate vector of each block. Specifically, one or more combinations of motion vectors having a matching cost equal to or below a predetermined threshold with respect to the electro-oculography change amount vector shown in FIG. 13A is extracted from a plurality of electro-oculography change amount candidate vectors shown in FIG. 13B. Then, the start positions of the motion vectors at the time t among each of the extracted combinations are determined as offset correcting position candidates. The processing of determining the offset correcting position from here is common to that in the first embodiment, and thus the description thereof will not be repeated.

FIG. 14 shows a processing procedure of the offset correcting position determining unit 202. First, a variable MinCost is initialized (S2001). Next, the above-described electro-oculography change amount vector and electro-oculography change amount candidate vectors are determined (S2002). Then, a comparison target block position, which is a target block position for the electro-oculography change amount comparison, is updated (S2003).

Subsequently, a sum of square differences Cost3, which is a matching cost, is calculated using the electro-oculography change amount vector and an electro-oculography change amount candidate vector at the comparison target block position (S2004). Next, it is determined whether or not the calculated sum of square differences Cost3 is smaller than a preset threshold TH3 (S2005).

When the comparison result is true, the comparison target block position is determined as an offset correcting position candidate, and a square difference Cost2 between an electro-oculogram generated at the comparison target block position and the electro-oculography signal calculated by the electro-oculography change amount calculating unit 140 is calculated (S2006). Then, it is determined whether or not the square difference Cost2 is smaller than a preset threshold TH2 and is smallest (S2007). When the result is true, MinCost is updated (S2008), and the comparison target block position is set as the offset correcting position (S2009).

Then, when the comparison is finished for all the blocks (S2010), it is determined whether or not an offset correcting position has been finally set, that is, whether or not tracking movement has been detected (S2011). When the result is true, the electro-oculogram generated at the offset correcting position is output (S2012). On the other hand, when the result is false, the electro-oculography signal is output without correction, and the processing is terminated (S2013).

It is to be noted that although a sum of square differences is used in the second embodiment as a matching cost between an electro-oculography change amount vector and each electro-oculography change amount candidate vector, a square-root of a sum of square differences, a sum of absolute differences, or the like may be used.

It is also to be noted that although in the second embodiment, the position at which the square difference Cost2 between the electro-oculogram generated at the comparison target block position and the electro-oculography signal calculated by the electro-oculography change amount calculating unit 140 is the smallest is determined as the offset correcting position, it does not necessarily have to be the smallest as in the first embodiment.

In addition, although the electro-oculography change amount memory 204 and the electro-oculography change amount candidate table memory 205 store electro-oculography change amounts and electro-oculography change amount candidate tables, respectively, which correspond to a predetermined time period and are input from the offset correcting position determining unit 202, the electro-oculography change amounts and the electro-oculography change amount candidate tables may be directly input from the electro-oculography change amount calculating unit 140 and the electro-oculography change amount candidate table generating unit 171, respectively.

Furthermore, although the second embodiment has been described using, as an example, the electro-oculography change amounts between the time t−2 and the time t, the present invention is not limited to this, and a greater amount of time information may be used.

According to the configuration of the second embodiment described above, offset correcting position candidates can be selected in consideration of temporal variations in electro-oculogram. As a result, a drift can be estimated with high precision.

Third Embodiment

Figure 15:
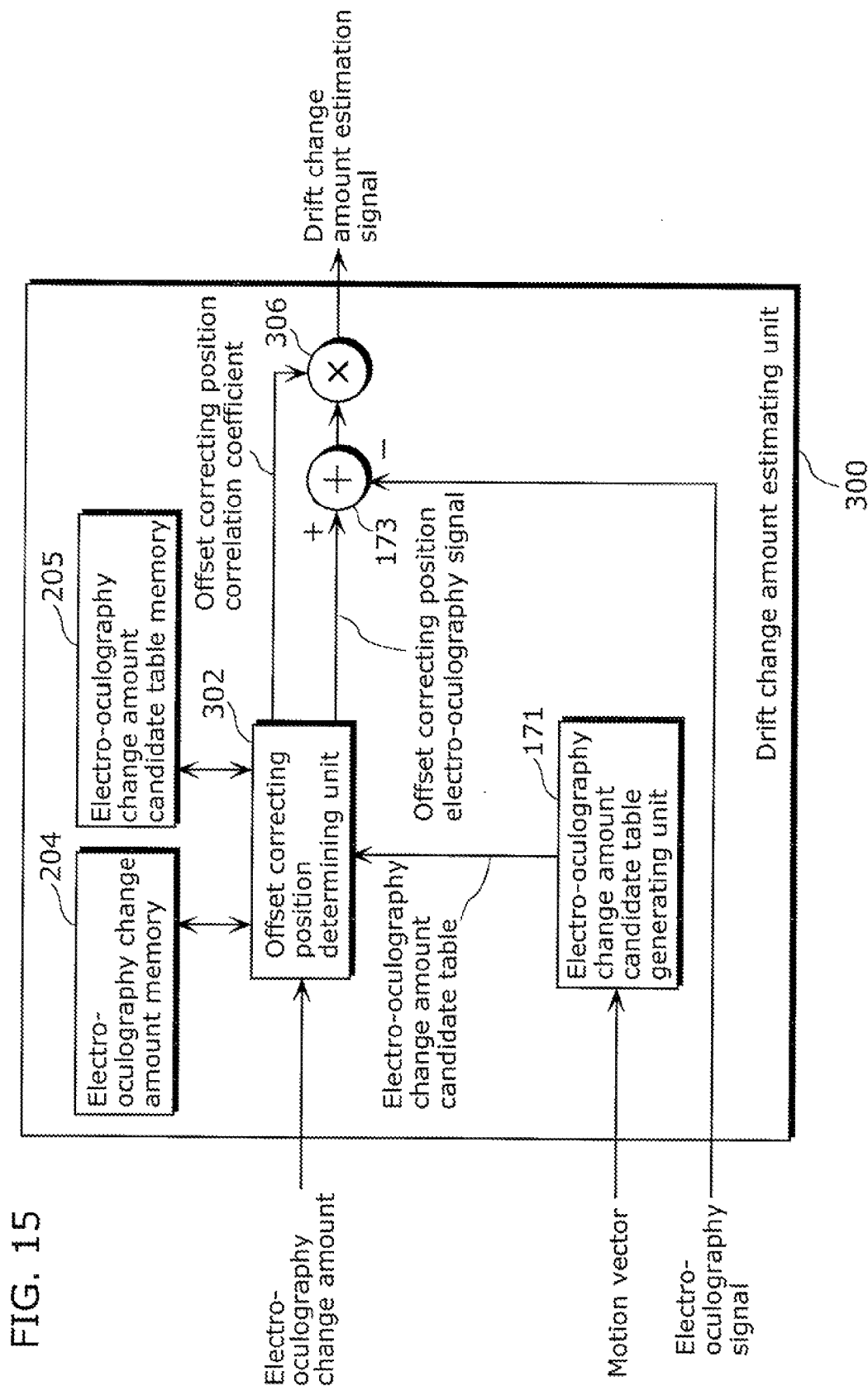
FIG. 15 is a block diagram of a drift change amount estimating unit according to a third embodiment.

FIG. 15 is a block diagram showing a configuration of a drift change amount estimating unit 300 according to a third embodiment of the present invention.

The drift change amount estimating unit 300 according to the third embodiment includes the electro-oculography change amount candidate table generating unit 171, an offset correcting position determining unit 302, the electro-oculography change amount memory 204, the electro-oculography change amount candidate table memory 205, the subtractor 173, and a multiplier 306. That is, the third embodiment is different from the second embodiment in newly including, in the drift change amount estimating unit 200 shown in FIG. 11, the multiplier 306 and the offset correcting position determining unit 302.

The constituent elements in FIG. 15 which are the same as those in FIG. 11 have already been described, and thus the same reference numerals are assigned and the descriptions thereof will not be repeated.

Figure 16:
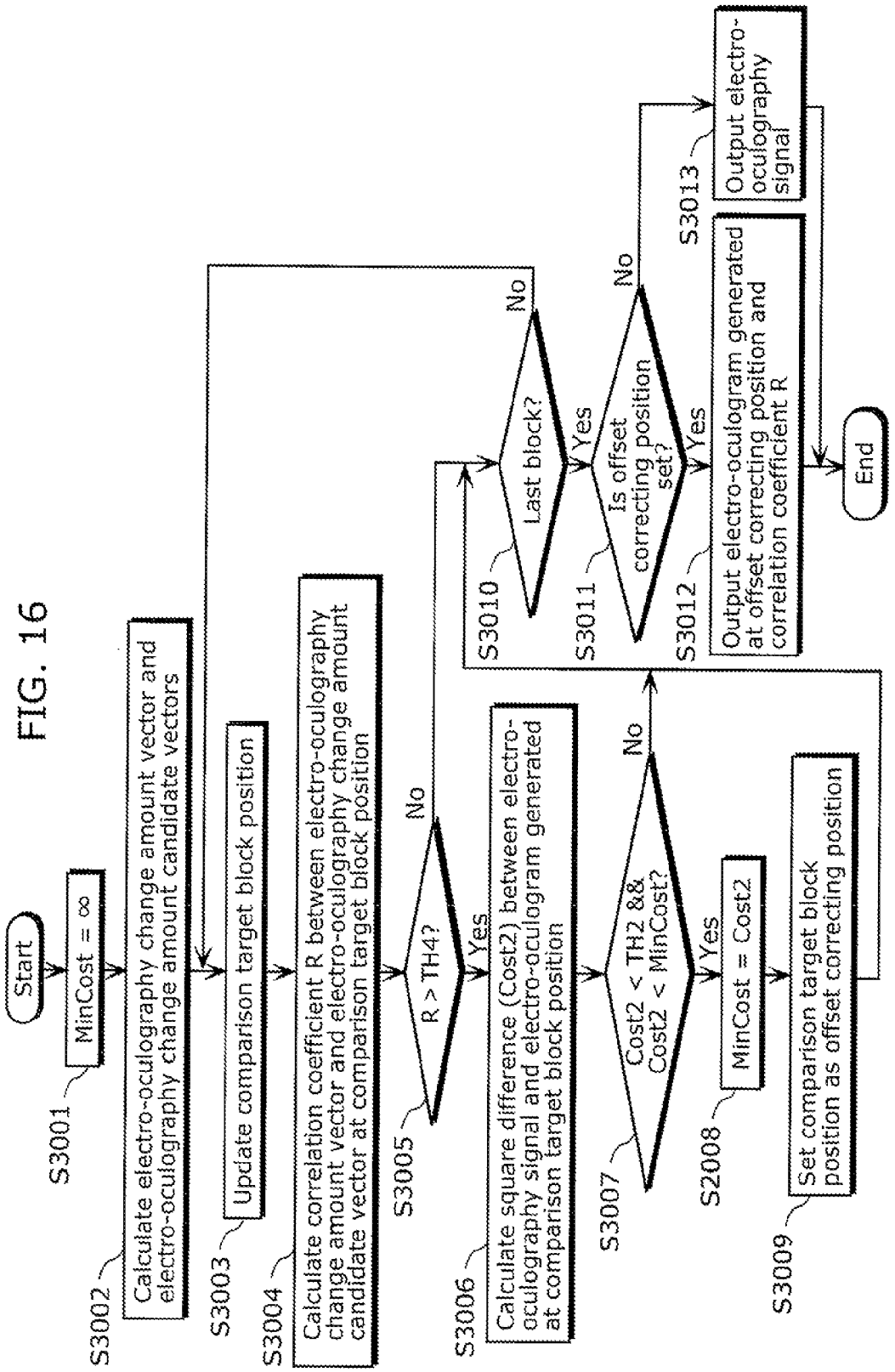
FIG. 16 is a flow chart showing an operation of an offset correcting position determining unit according to the third embodiment.

A processing procedure of the offset correcting position determining unit 302 according to the third embodiment will be described with reference to FIG. 16. First, a variable Min-Cost is initialized (S3001). Next, an electro-oculography change amount vector and electro-oculography change amount candidate vectors are determined (S3002). Then, a comparison target block position, which is a target block position for the electro-oculography change amount comparison, is updated (S3003).

Subsequently, a correlation coefficient R is calculated using the electro-oculography change amount vector and an electro-oculography change amount candidate vector at the comparison target block position (S3004). The method of calculating the correlation coefficient R is not limited to a specific method; an inner product of vectors may be used, for example. More specifically, the correlation coefficient R may be a result obtained by dividing an inner product of two vectors by the magnitudes of the two vectors. In this case, the smaller the angle θ between the two vectors, the larger the correlation coefficient R (approaches 1).

Next, it is determined whether or not the calculated correlation coefficient R is larger than a preset threshold TH4 (S3005). When the comparison result is true, the comparison target block position is determined as an offset correcting position candidate, and a square difference Cost2 between an electro-oculogram generated at the comparison target block position and the electro-oculography signal calculated by the electro-oculography change amount calculating unit 140 is calculated (S3006).

Then, it is determined whether or not the square difference Cost2 is smaller than a preset threshold TH2 and is smallest (S3007). When the result is true, MinCost is updated (S3008), and the comparison target block position is set as the offset correcting position (S3009).

When the comparison is finished for all the blocks (S3010), it is determined whether or not an offset correcting position has been finally set, that is, whether or not tracking movement has been detected (S3011). When the result is true, the electro-oculogram generated at the offset correcting position and the corresponding correlation coefficient R, as an offset correcting position correlation coefficient, are output (S3012). On the other hand, when the result is false, the electro-oculography signal is output without correction, and the processing is terminated (S3013).

The multiplier 306 multiplies, by the offset correcting position correlation coefficient which is output from the offset correcting position determining unit 302, an output value calculated by the subtractor 173 by subtracting the electro-oculography signal from the electro-oculogram generated at the offset correcting position, and outputs the product as a drift change amount estimation signal.

It is to be noted that although in the third embodiment, the position at which the square difference Cost2 between the electro-oculogram generated at the comparison target block position and the electro-oculography signal calculated by the electro-oculography change amount calculating unit 140 is the smallest is determined as the offset correcting position, it does not necessarily have to be the smallest as in the first and second embodiments.

According to the configuration of the third embodiment described above, the drift change amount estimation signal is adjusted according to the correlation coefficient R between the electro-oculography change amount vector and the electro-oculography change amount candidate vector at the determined offset correcting position. As a result, an influence of false drift detection can be reduced.

Fourth Embodiment

In a fourth embodiment of the present invention, using the properties of eyeball movement that an amount of change in eyeball movement does not exceed an amount of change in motion of a moving object in view at times other than a saccade, that is, at the time of tracking movement or fixation, the drift estimation signal is generated by estimating, as a drift change amount, an electro-oculography change amount exceeding the value of the largest motion vector in view at the time of tracking movement or fixation.

Figure 17:
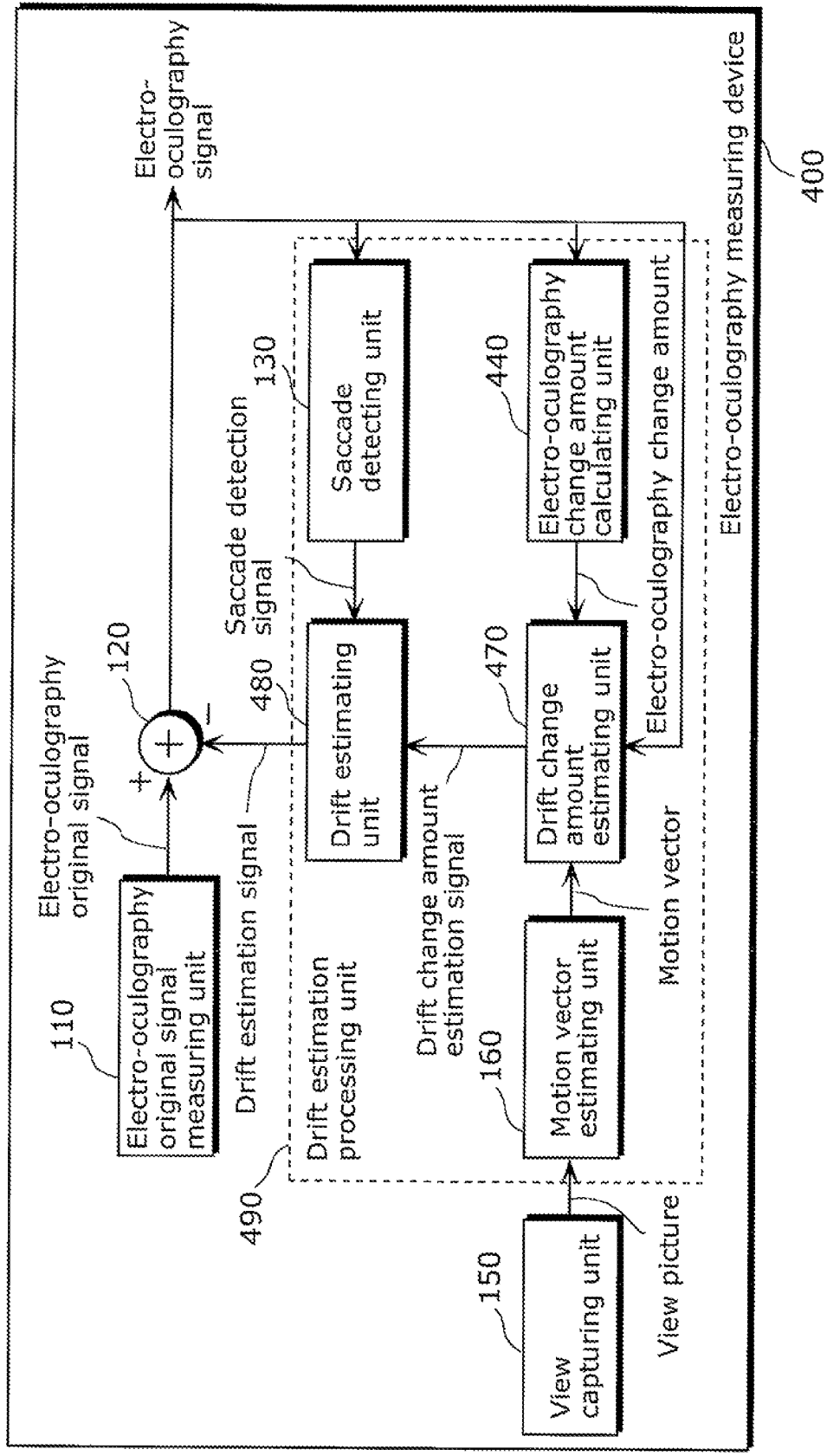
FIG. 17 is a block diagram of an electro-oculography measuring device according to a fourth embodiment.

FIG. 17 is a block diagram showing a configuration of an electro-oculography measuring device 400 according to the fourth embodiment. The electro-oculography measuring device 400 according to the fourth embodiment includes the electro-oculography original signal measuring unit 110, the subtractor 120, the view capturing unit 150, and a drift estimation processing unit 490. In addition, the drift estimation processing unit 490 includes the saccade detecting unit 130, an electro-oculography change amount calculating unit 440, the motion vector estimating unit 160, a drift change amount estimating unit 470, and a drift estimating unit 480. That is, the electro-oculography change amount calculating unit 440, the drift change amount estimating unit 470, and the drift estimating unit 480 are configured and operate differently from those in the first embodiment.

The constituent elements in FIG. 17 which are the same as those in FIG. 1 have already been described, and thus the same reference numerals are assigned and the descriptions thereof will not be repeated.

The electro-oculography change amount calculating unit 440 calculates an amount of change in electro-oculogram using an electro-oculography signal.

Figure 18:
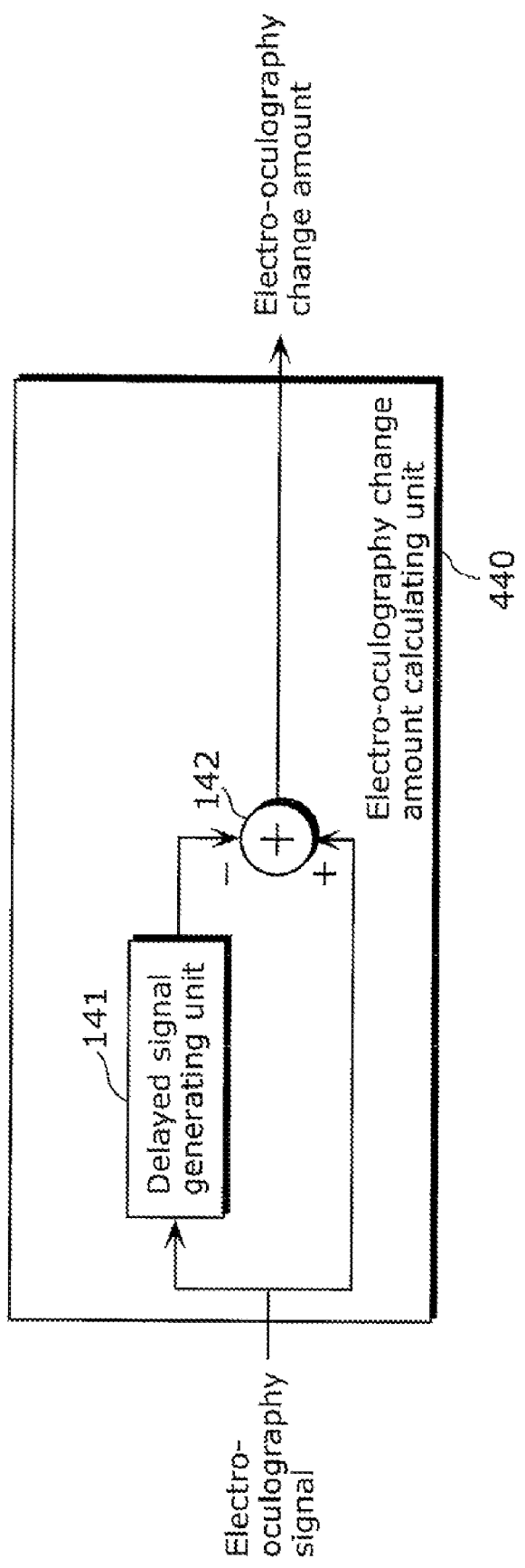
FIG. 18 is a block diagram of an electro-oculography change amount calculating unit in FIG. 17.

The electro-oculography change amount calculating unit 440 according to the fourth embodiment will be described with reference to FIG. 18. FIG. 18 is a diagram showing a configuration of the electro-oculography change amount calculating unit 440 according to the fourth embodiment. The electro-oculography change amount calculating unit 440 includes the delayed signal generating unit 141 and the subtractor 142. That is, the electro-oculography change amount calculating unit 440 is different from the electro-oculography change amount calculating unit 140 according to the first embodiment shown in FIG. 2 in that the fixation determining unit 143 is not included and thus the fixation detection signal is not output. The constituent elements in FIG. 18 which are the same as those in FIG. 2 have already been described, and thus the same reference numerals are assigned and the descriptions thereof will not be repeated.

The drift change amount estimating unit 470 generates a drift change amount estimation signal by clipping, at the value of the largest motion vector in a view picture, an electro-oculography change amount at a time t which is output from the electro-oculography change amount calculating unit 440.

Figure 19:
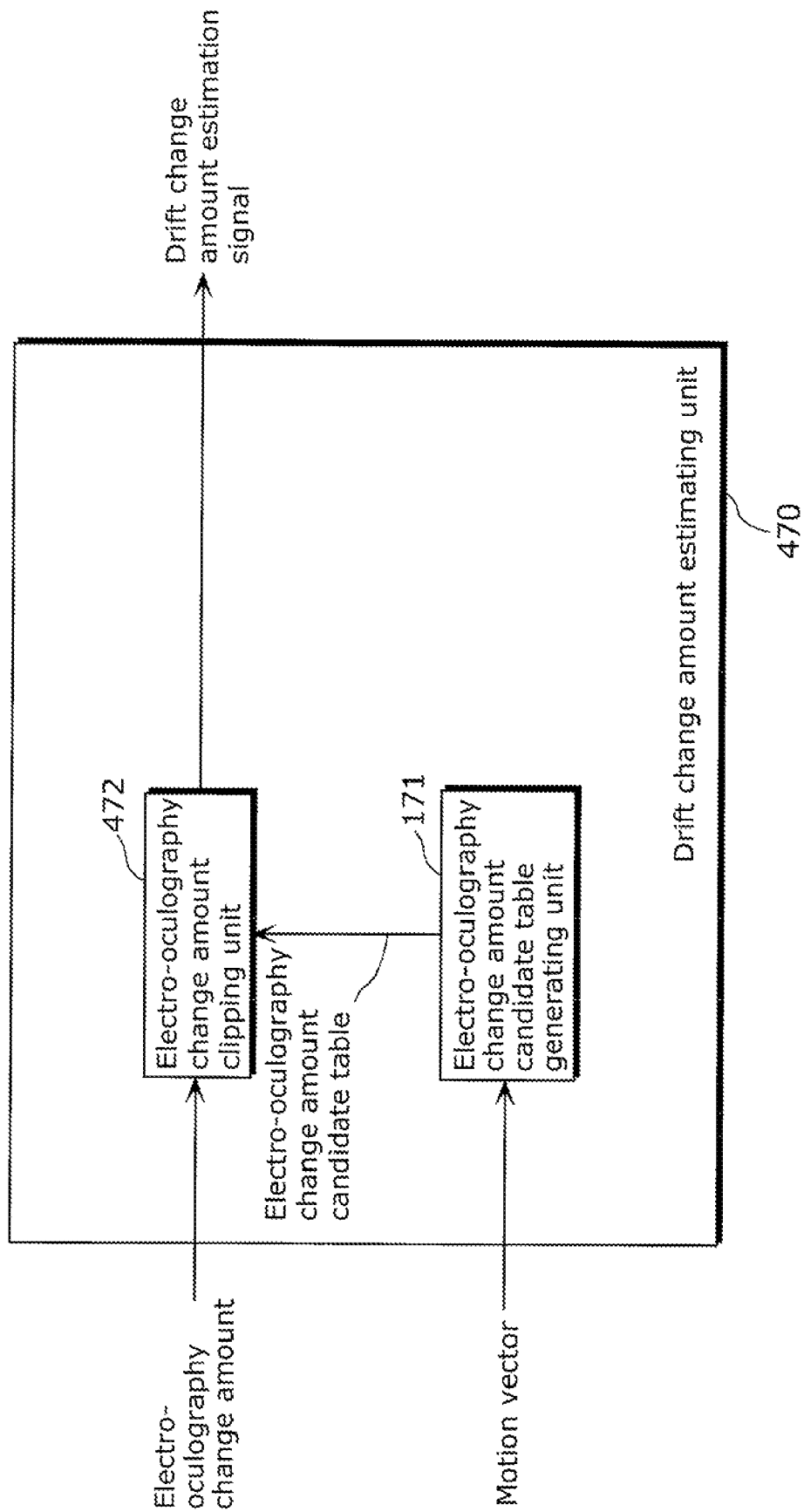
FIG. 19 is a block diagram of a drift change amount calculating unit in FIG. 17.

The drift change amount estimating unit 470 according to the fourth embodiment will be described with reference to FIG. 19. FIG. 19 is a diagram showing a configuration of the drift change amount estimating unit 470 according to the fourth embodiment. The drift change amount estimating unit 470 includes the electro-oculography change amount candidate table generating unit 171 and an electro-oculography change amount clipping unit 472. That is, the fourth embodiment is different from the first embodiment in not including, in the drift change amount estimating unit 170 shown in FIG. 5, the offset correcting position determining unit 172 and the subtractor 173, and newly including the electro-oculography change amount clipping unit 472. The constituent elements in FIG. 19 which are the same as those in FIG. 5 have already been described, and thus the same reference numerals are assigned and the descriptions thereof will not be repeated.

The electro-oculography change amount clipping unit 472 estimates a drift change amount using an electro-oculography change amount and an electro-oculography change amount candidate table.

Figure 20:
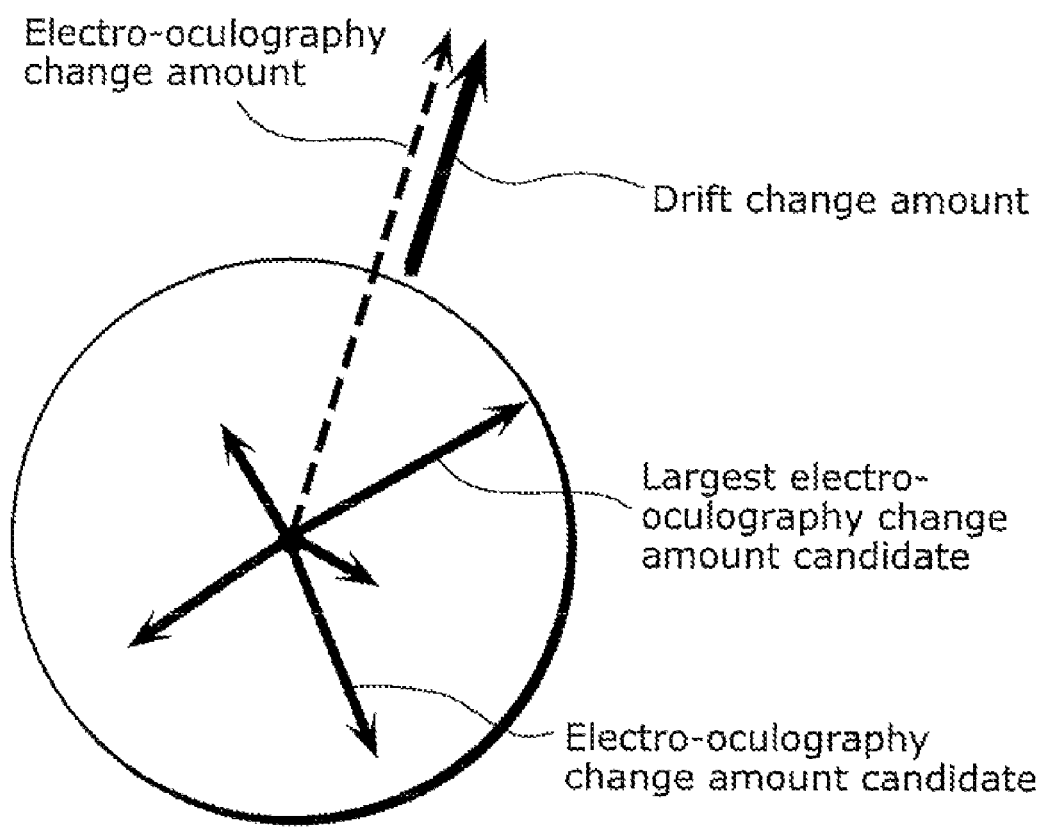
FIG. 20 is a diagram showing an example of a drift change amount estimated according to the fourth embodiment.

Specifically, using the electro-oculography change amount candidate table, the electro-oculography change amount clipping unit 472 first searches for the largest motion-vector-equivalent electro-oculography change amount having the largest amplitude among motion-vector-equivalent electro-oculography change amounts at respective block positions. Then, as shown in FIG. 20, a portion of the electro-oculography change amount at the time t, by which the electro-oculography change amount exceeds the largest motion-vector-equivalent electro-oculography change amount, is estimated as a drift change amount.

Figure 21:
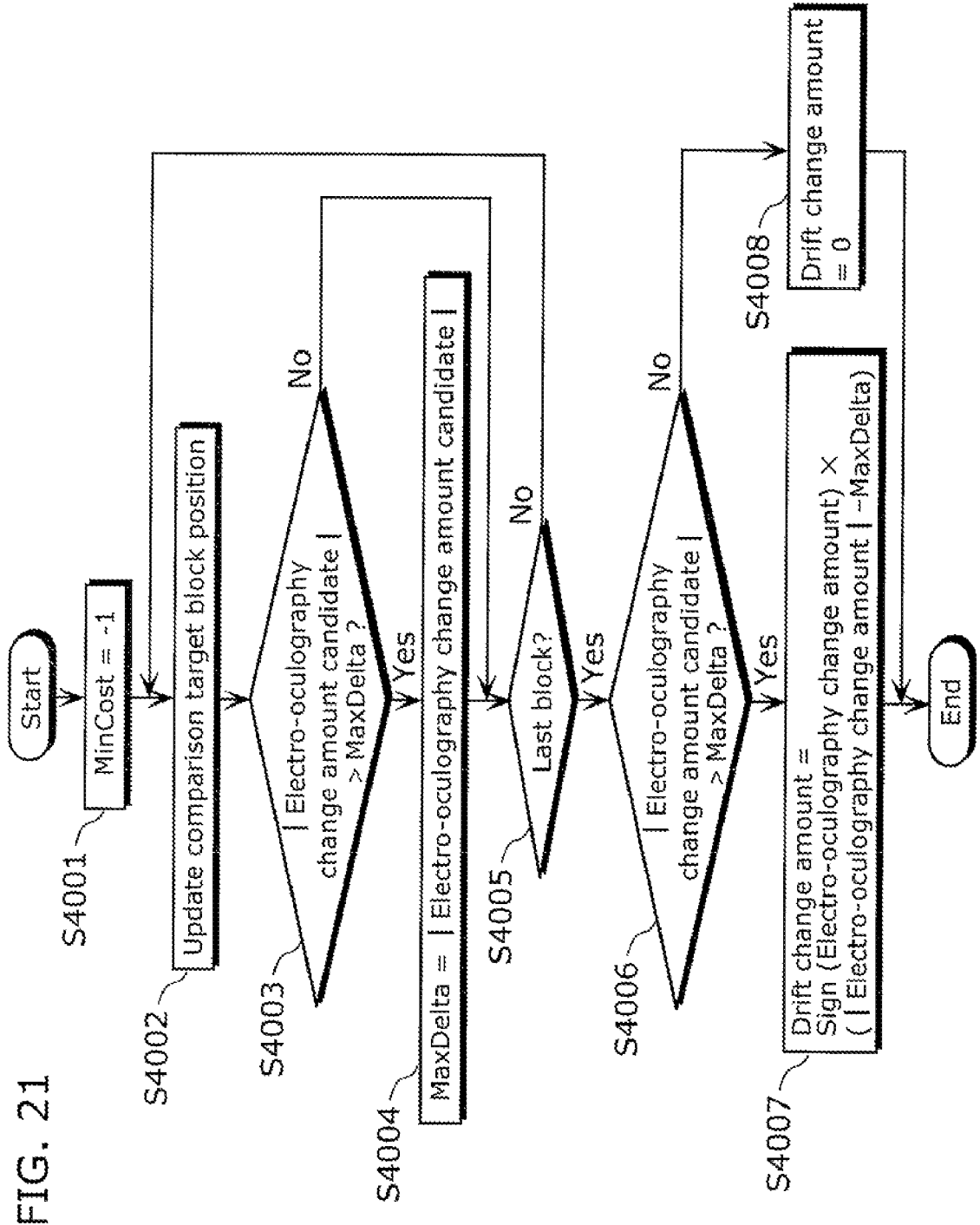
FIG. 21 is a flow chart showing an operation of an electro-oculography change amount clipping unit according to the fourth embodiment.

FIG. 21 shows a processing procedure of the electro-oculography change amount clipping unit 472. First, the largest motion-vector-equivalent electro-oculography change amount MaxDelta having the largest amplitude among electro-oculography change amount candidates is calculated (S4001 to S4005).

Then, the amplitude of the electro-oculography change amount at the time t and MaxDelta are compared (S4006). When the comparison result is true, the drift change amount is calculated by multiplying, by the sign of the electro-oculography change amount, the portion of the electro-oculography change amount by which the electro-oculography change amount exceeds MaxDelta (S4007). On the other hand, when the comparison result is false, 0 is output as the drift change amount (S4008). It is to be noted that Sign (electro-oculography change amount) in FIG. 21 indicates the sign of the electro-oculography change amount; it indicates 1 when the electro-oculography change amount is plus, and −1 when minus.

As an example of the electro-oculography change amount clipping process, in the case where the electro-oculography change amount at the time t is 800 μV and an electro-oculography change amount candidate table as shown in FIG. 7 is given, for example, following the processing procedure in FIG. 21 results in selecting, as MaxDelta, of the motion vector equivalent electro-oculography change amount 500 μV corresponding the block position (2, 3), which thereby gives a calculation result of 300 μV as the drift change amount.

The drift estimating unit 480 generates a drift estimation signal from the drift change amount estimation signal and the saccade detection signal.

Figure 22:
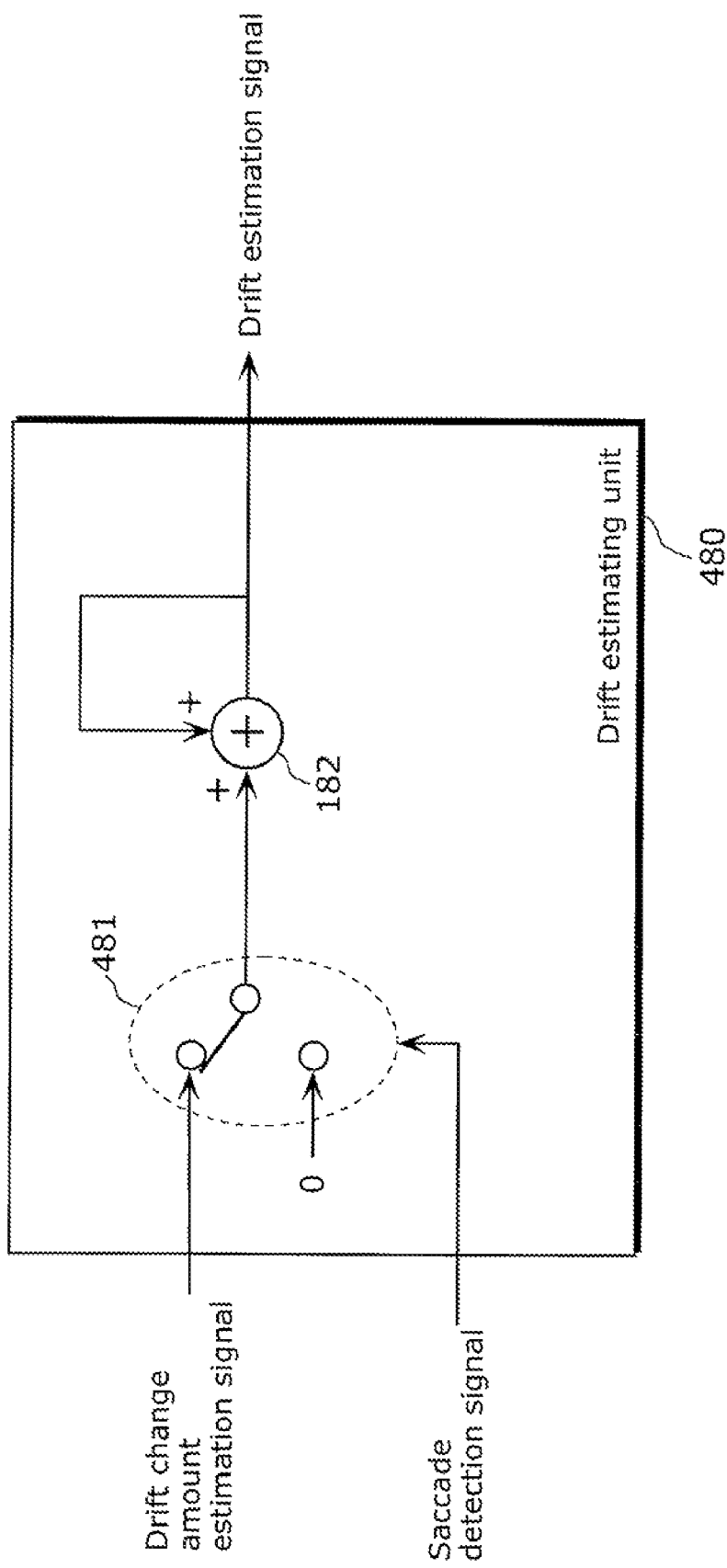
FIG. 22 is a block diagram of a drift estimating unit in FIG. 17.

The drift estimating unit 480 according to the fourth embodiment will be described with reference to FIG. 22. FIG. 22 is a diagram showing a configuration of the drift estimating unit 480 according to the fourth embodiment. The drift estimating unit 480 includes a switch 481 and the adder 182. That is, the switch 481 operates differently from the switch in the first embodiment. The constituent elements in FIG. 22 which are the same as those in FIG. 10 have already been described, and thus the same reference numerals are assigned and the descriptions thereof will not be repeated.

The switch 481 performs switching to change an output signal provided to the adder 182, according to the saccade detection signal from the saccade detecting unit 130. Specifically, when the saccade detection signal is high (when a saccade is detected), the switching is performed so that 0 is output. On the other hand, when the saccade detection signal is low (saccade is not detected), the switching is performed so that the drift change amount estimation signal from the drift change amount estimating unit 470 is output.

Such a switching operation allows the drift estimation signal to be updated only when a saccade is not detected, that is, only at the time of tracking movement or a fixation.

According to the configuration of the fourth embodiment described above, at the times other than a saccade, that is, at the time of tracking movement or a fixation, a portion of an electro-oculography change amount, by which the electro-oculography change amount exceeds the value of the largest motion vector in view, is estimated as the drift change amount, thereby allowing precise drift component estimation especially when there is no moving object in view.

Next, the method by which the saccade detecting unit 130 detects the saccade signal in the electro-oculography signal (hereinafter referred as electro-oculography original signal) will be described in detail. It is to be noted that the saccade signal is widely used for detecting eyeball movement and a state of a user, not only in the electro-oculography measuring device 100 described above but also in the fields such as medical equipment, driver supporting devices, and user interfaces. Therefore, it is significantly effective to detect the saccade signal with ease and high accuracy.

For example, the following Patent Literatures 3 to 5 disclose techniques of detecting a saccade signal from an electro-oculography original signal.

Japanese Unexamined Patent Application Publication No. 11-276461 (Patent Literature 3) discloses a technique of detecting a saccade signal from an operator and determining the attentiveness of the operator based on the occurrence frequency of the saccade signal. It is to be noted that a high-pass filter having a cutoff frequency of approximately 0.05 to 0.1 Hz is used for detecting a saccade signal.

Japanese Unexamined Patent Application Publication No. 9-034631 (Patent Literature 4) discloses a technique for eliminating the need for manually aligning a pointer on the display screen and a gaze point of an operator. Specifically, when a saccade signal is detected within a predetermined period of time after a calibration symbol is generated on the display screen, it is determined that the calibration symbol and the gaze point of the operator have matched, and thus the position of the pointer is calibrated. It is to be noted that a high-pass filter having a cutoff frequency of approximately 0.05 to 0.1 Hz is used for detecting a saccade signal.

Japanese Unexamined Patent Application Publication No. 2002-272693 (Patent Literature 5) discloses a technique of detecting an end time point of saccadic movement on the basis of an eyeball movement signal. Then, every time saccadic movement ends, brain waves within a certain period of time from the end time point are consecutively stored for a plurality of parts of the brain as unit brain waves, so that an eyeball-fixation-related potential is obtained. It is to be noted that a saccade signal is detected by determining whether or not the direction of eyeball movement has changed after continuously staying in the same direction within a predetermined period of time.

Figure 24:
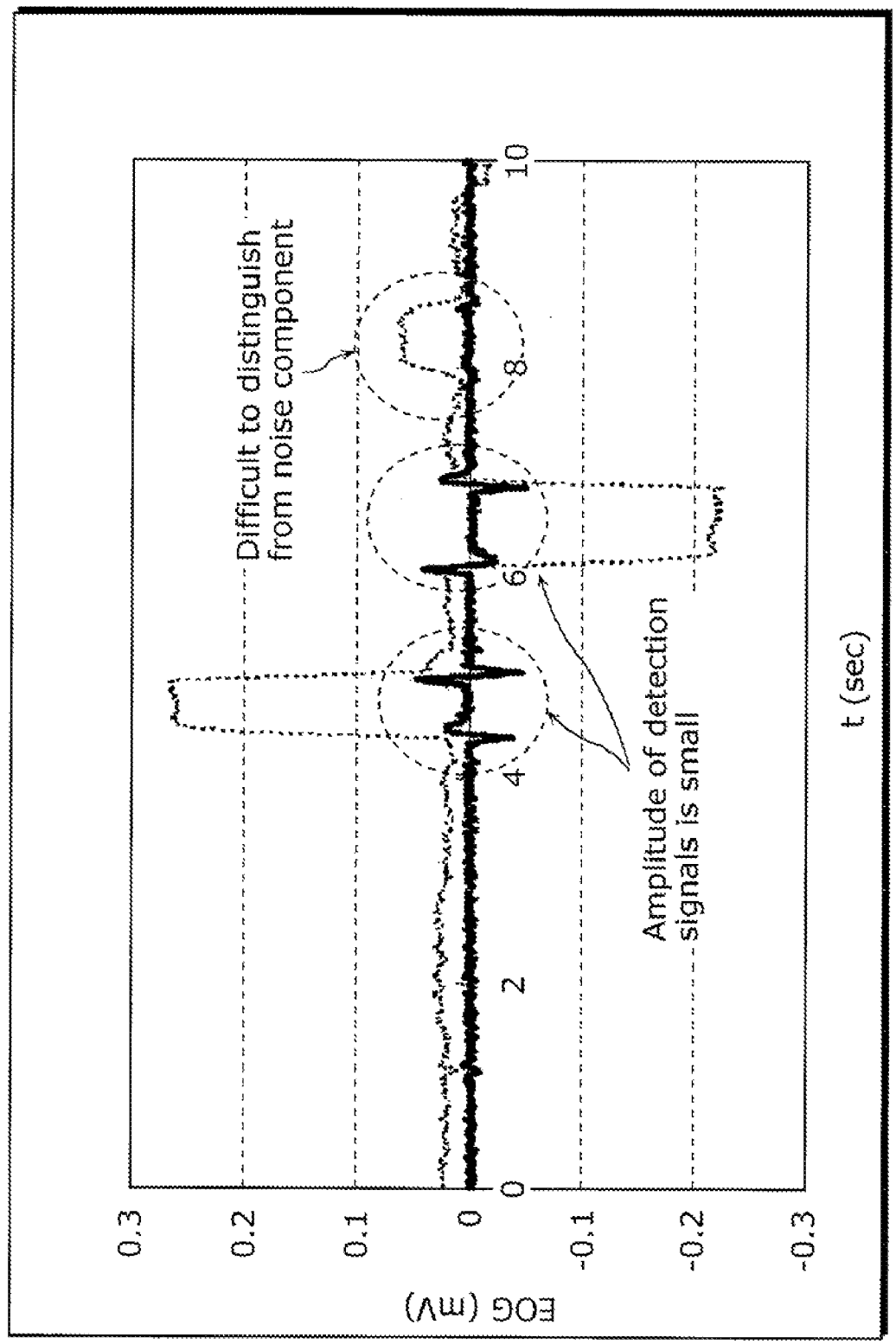
FIG. 24 is a diagram showing an electro-oculography signal obtained by applying a high-pass filter to the electro-oculography signal in FIG. 23.

The saccade detection methods as disclosed in Patent Literatures 3 to 5 may be adopted for the saccade detecting unit 130 shown in FIG. 1. However, with the methods disclosed in Patent Literatures 3 and 4, a saccade signal is detected using a high-pass filter. When the electro-oculography signal shown in FIG. 23 passes through a high-pass filter, the amplitude of a saccade signal decreases in some cases as shown in FIG. 24. Particularly a saccade signal with a small amplitude cannot be distinguished from noise components in some cases.

In addition, with the method disclosed in Patent Literature 5, there is a possibility of false saccade detection. For example, when detecting the direction of eyeball movement, it fails to determine, due to an influence of a noise component or the like, that the direction of eyeball movement is continuously the same even in saccadic movement.

In view of the above, a method of accurately and easily detecting a saccade signal from an electro-oculography original signal of a user will be described in fifth through eleventh embodiments of the present invention. It is to be noted that although the following description shows an example of detecting a saccade signal from an electro-oculography original signal including a drift signal, which is obtained from the electrodes attached to the user, the same description can be applied to the case where a saccade signal is detected from an electro-oculography signal from which a drift signal has been removed, as described in the first through fourth embodiments.

Fifth Embodiment

Figure 25:
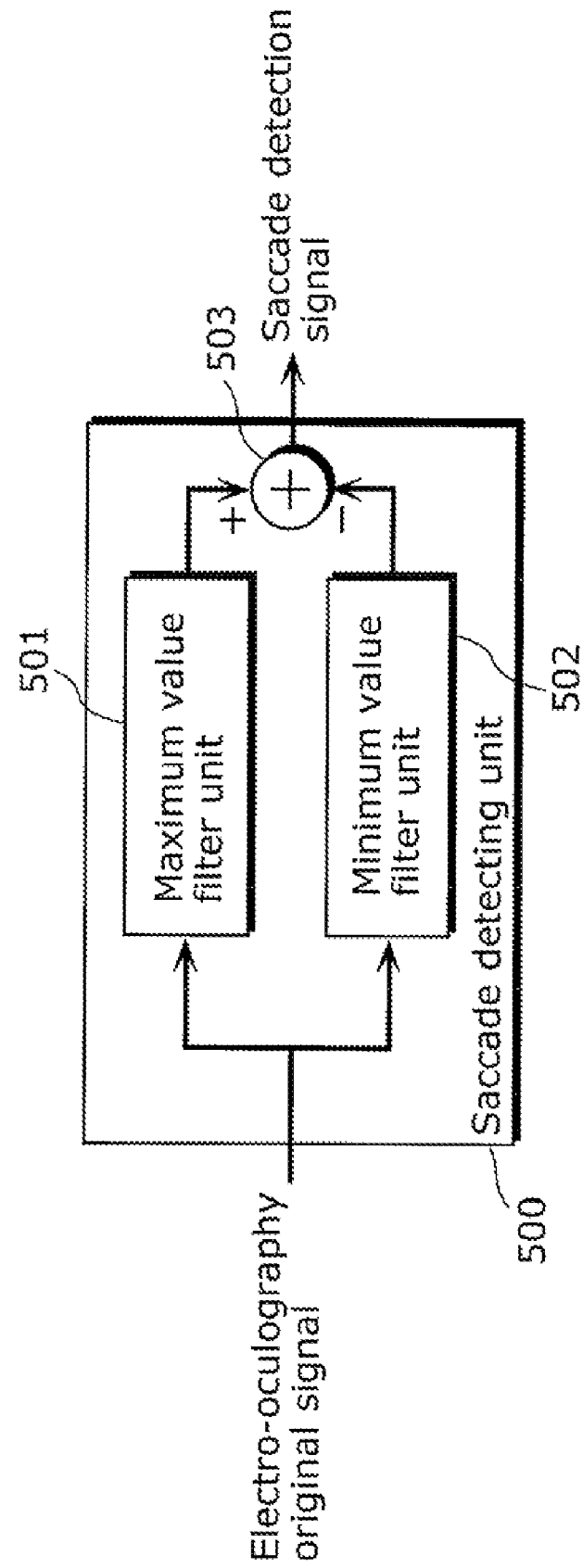
FIG. 25 is a block diagram of a saccade detecting unit according to a fifth embodiment.

FIG. 25 is a block diagram showing a configuration of a saccade detecting unit 500 according to a fifth embodiment of the present invention. The saccade detecting unit 500 shown in FIG. 25 includes: a maximum value filter unit (the first filtering unit) 501 which performs maximum value filtering on an electro-oculography original signal; a minimum value filter unit (the second filtering unit) 502 which performs minimum value filtering on the electro-oculography original signal; and a subtractor 503.

More specifically, the maximum value filter unit 501 and the minimum value filter unit 502 are connected in parallel to each other. The maximum value filter unit 501 performs the maximum value filtering on the electro-oculography original signal to output a first electro-oculography signal. The minimum value filter unit 502 performs the minimum value filtering on the electro-oculography original signal to output a second electro-oculography signal. Then, the subtractor 503 subtracts the second electro-oculography signal from the first electro-oculography signal to generate an output signal.

It is to be noted that the present invention is intended for the case where the electro-oculography original signal does not include a blink component of a user as seen in attaching the electrodes to the right and left of an eyeball as shown in FIGS. 64A and 64B or in the measuring method in which the electrodes are attached at a position away from the eye. The detection of a saccade signal by using such a measuring method will be hereinafter described.

Next, processing of the maximum value filter unit 501 in FIG. 25 will be described. The maximum value filter unit 501 performs filtering described below on an electro-oculography original signal f(x).

$$f\max(x) = \max(f\max(x), f(x+i))$$

when n is an odd number, $(-n/2 \leq i \leq n/2)$ when n is an even number, $(-n/2 \leq n/2)$ or $(-n/2 \leq n/2)$ Here, fmax (x) is an electro-oculography signal after the maximum value filtering is performed, n is the number of filter taps, and i is an integer. In addition, max (a, b) is a function that returns a larger value of a and b. Thus, the maximum value filtering outputs a sampled value having the largest amplitude among n samples centering on an arbitrary sample f(x) included in the electro-oculography original signal. By performing this processing on each of the samples of the electro-oculography original signal, it is possible to obtain the first electro-oculography signal.

Figure 26:
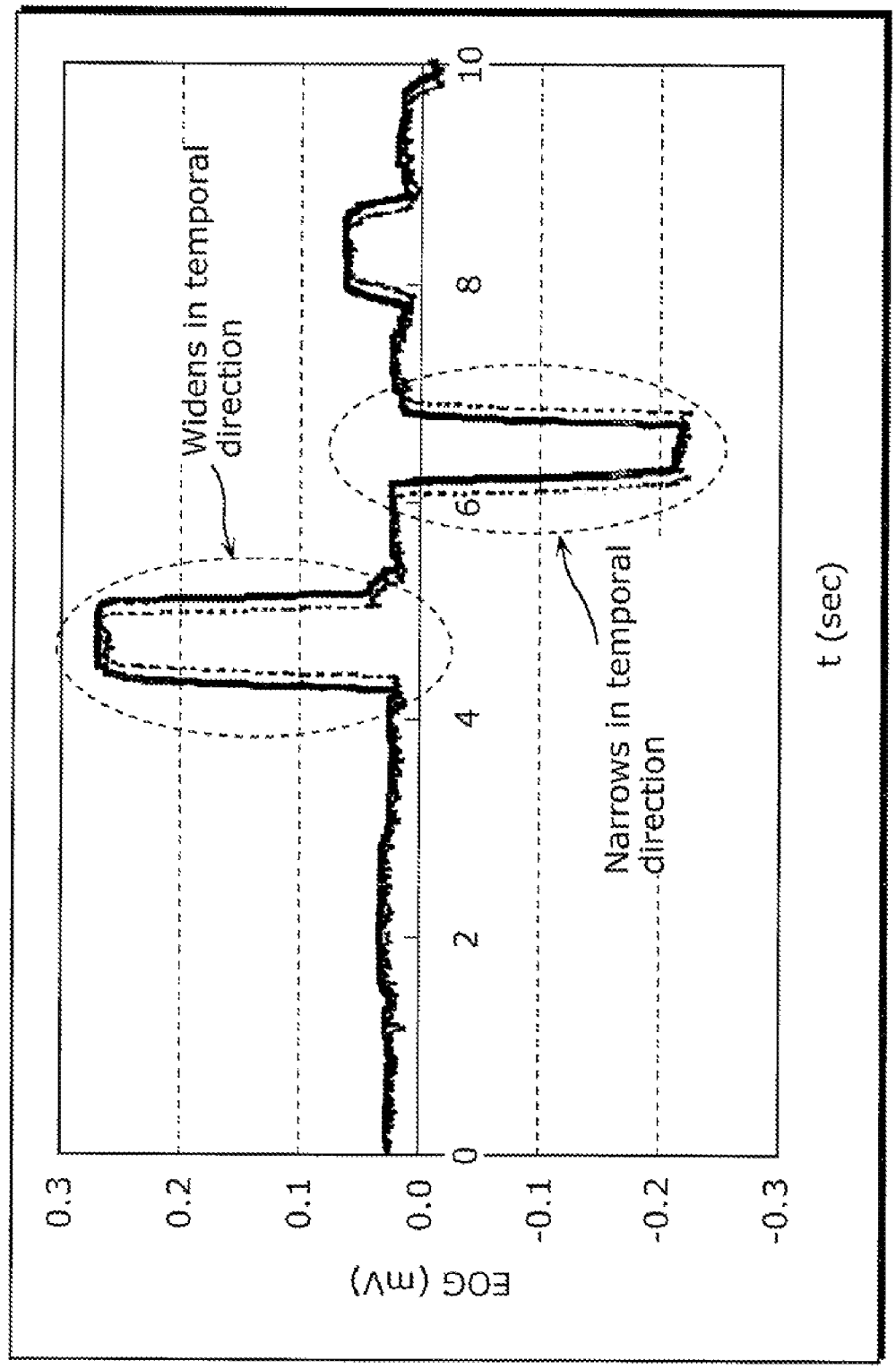
FIG. 26 is a diagram showing an electro-oculography signal obtained by applying maximum value filtering (unit processing period=0.25 seconds) to the electro-oculography signal in FIG. 23.

FIG. 26 shows an example of performing the above-described filtering on the electro-oculography original signal in FIG. 23. It is to be noted that the unit processing period for the maximum value filtering is set to 0.25 seconds for detecting the saccade signal from the electro-oculography original signal. It is to be noted that the unit processing period indicates a time interval including a sample on which a single maximum value filtering is to be performed. In addition, the number of filter taps n of the maximum value filter unit 501 is the number of samples included in the unit processing period (0.25 seconds). Thus, it is possible to calculate the number of filter taps n, using the unit processing period and a sampling frequency for performing A/D conversion on the electro-oculography original signal.

Figure 27:
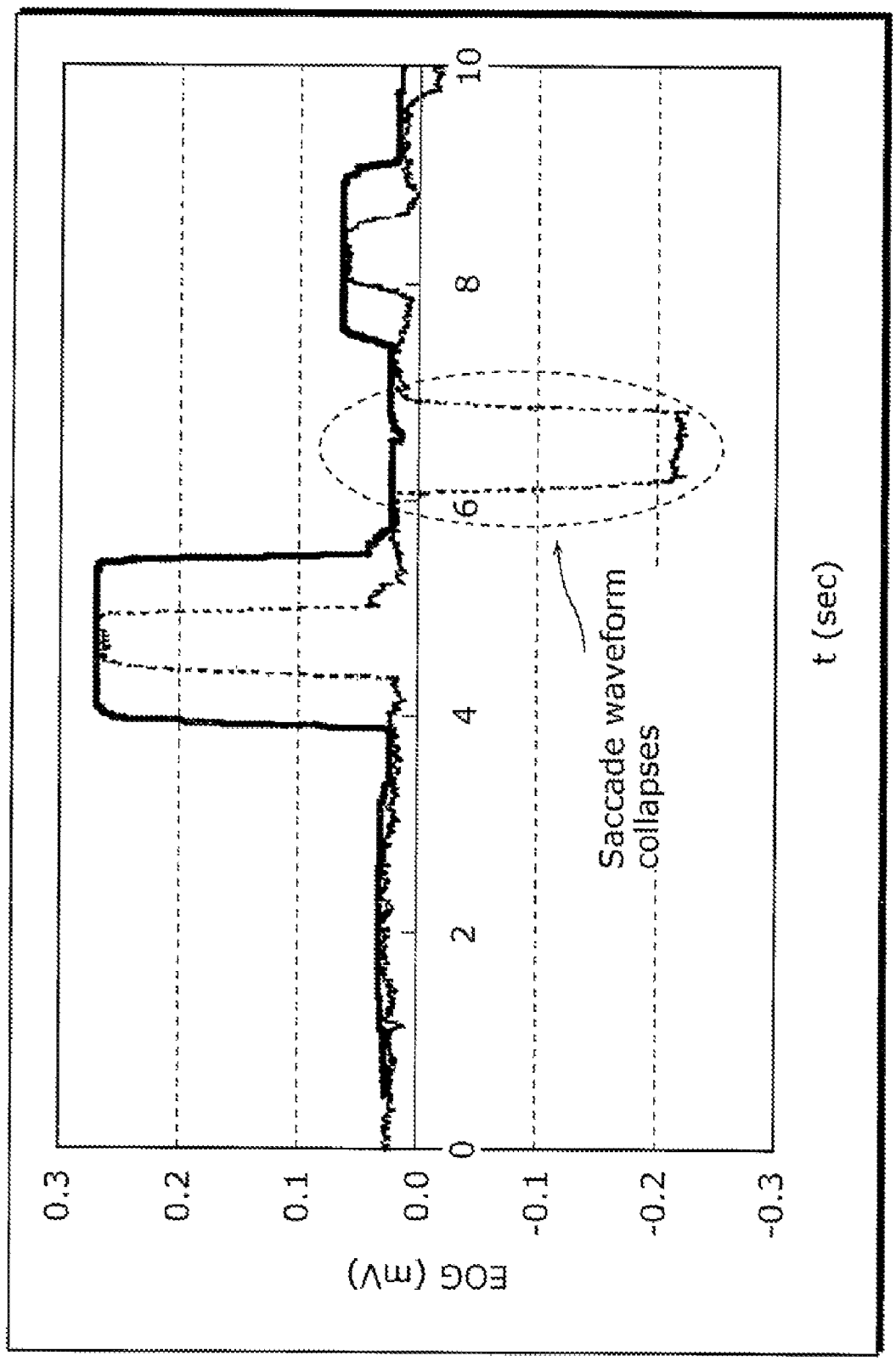
FIG. 27 is a diagram showing an electro-oculography signal obtained by applying maximum value filtering (unit processing period=1.0 second) to the electro-oculography signal in FIG. 23.

As shown in FIG. 26, when the maximum value filtering is performed on the electro-oculography original signal, a plus signal widens in the temporal direction and a minus signal narrows in the temporal direction. However, when the unit processing period of the maximum value filter unit 501 is set longer than a general single fixation time (approximately 0.3 to 0.4 seconds), the saccade waveform in the minus direction collapses as shown in FIG. 27. FIG. 27 is an example of the maximum value filtering performed with the unit processing period set to 1.0 second. Since the saccade signal cannot be detected when the saccade waveform collapses as shown in FIG. 27, it is necessary to make the unit processing period of the maximum value filter unit 501 shorter than the general single fixation time.

It is to be noted that, although an example in which the unit processing period of the maximum value filtering is 0.25 seconds has been described in the fifth embodiment, the unit processing period may be any value as long as it is shorter than the general single fixation time.

Next, processing of the minimum value filter unit 502 will be described. The minimum value filter unit 502 performs filtering on the electro-oculography original signal f(x) as described below.

$$fmin(x)=min(fmin(x), f(x+i))$$

when n is an odd number, $(-n/2 < i \leq n/2)$
when n is an even number, $(-n/2 \geq i < n/2)$ or $(-n/2 < i \geq n/2)$ Here, fmin (x) is an electro-oculography signal after the minimum value filtering is performed, n is the number of filter taps, and i is an integer. In addition, min (a, b) is a function that returns a smaller value of a and b. Thus, the minimum value filtering outputs a sampled value having the smallest amplitude among n samples centering on an arbitrary sample f(x) included in the electro-oculography original signal. By performing this processing on each of the samples of the electro-oculography original signal, it is possible to obtain the second electro-oculography signal.

Figure 28:
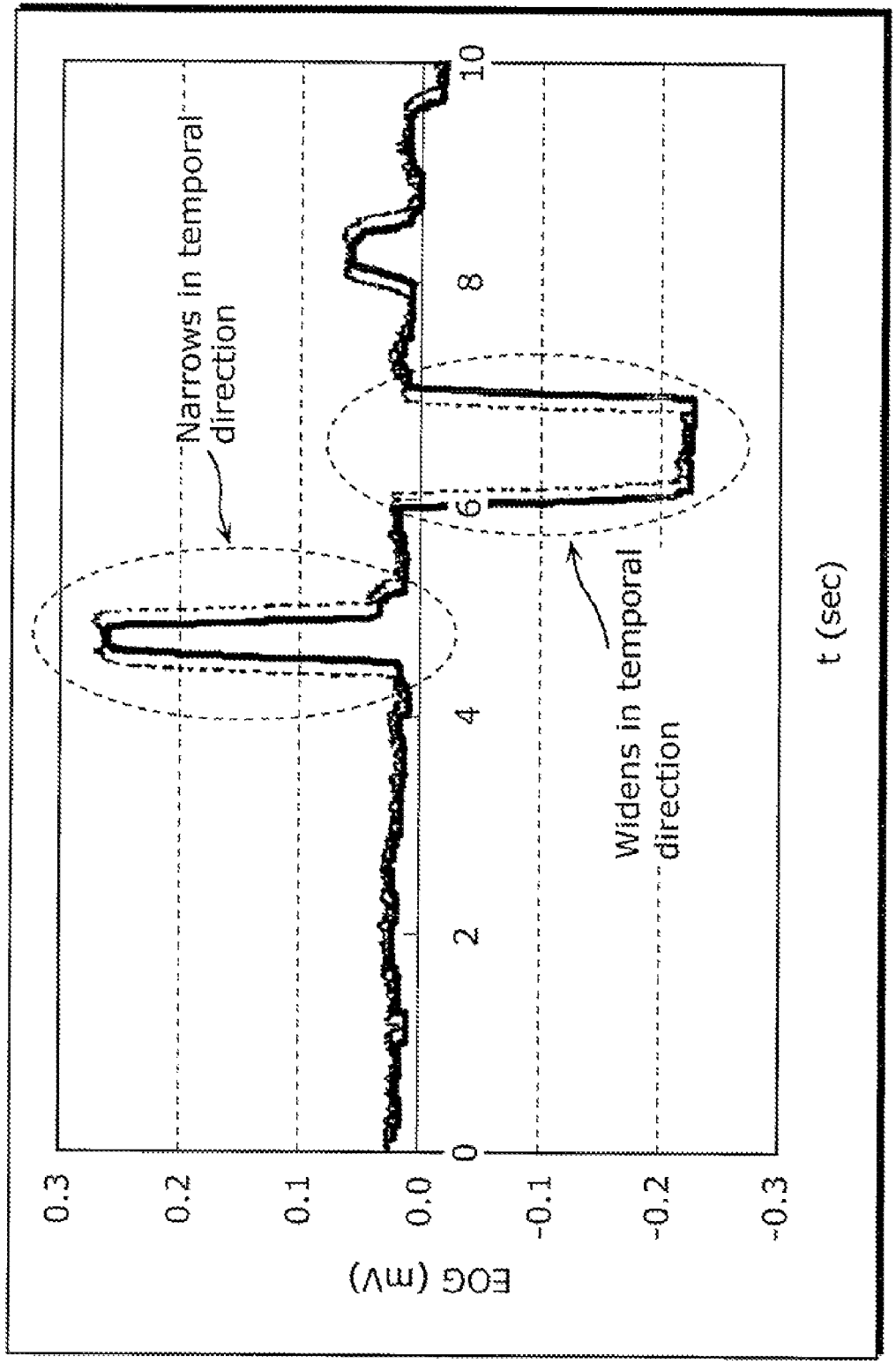
FIG. 28 is a diagram showing an electro-oculography signal obtained by applying minimum value filtering (unit processing period=0.25 seconds) to the electro-oculography signal in FIG. 23.

FIG. 28 shows an example of performing the above-described filtering on the electro-oculography original signal in FIG. 23.

In FIG. 28, the unit processing period for the minimum value filtering is set to 0.25 seconds for detecting the saccade signal from the electro-oculography original signal.

Figure 29:
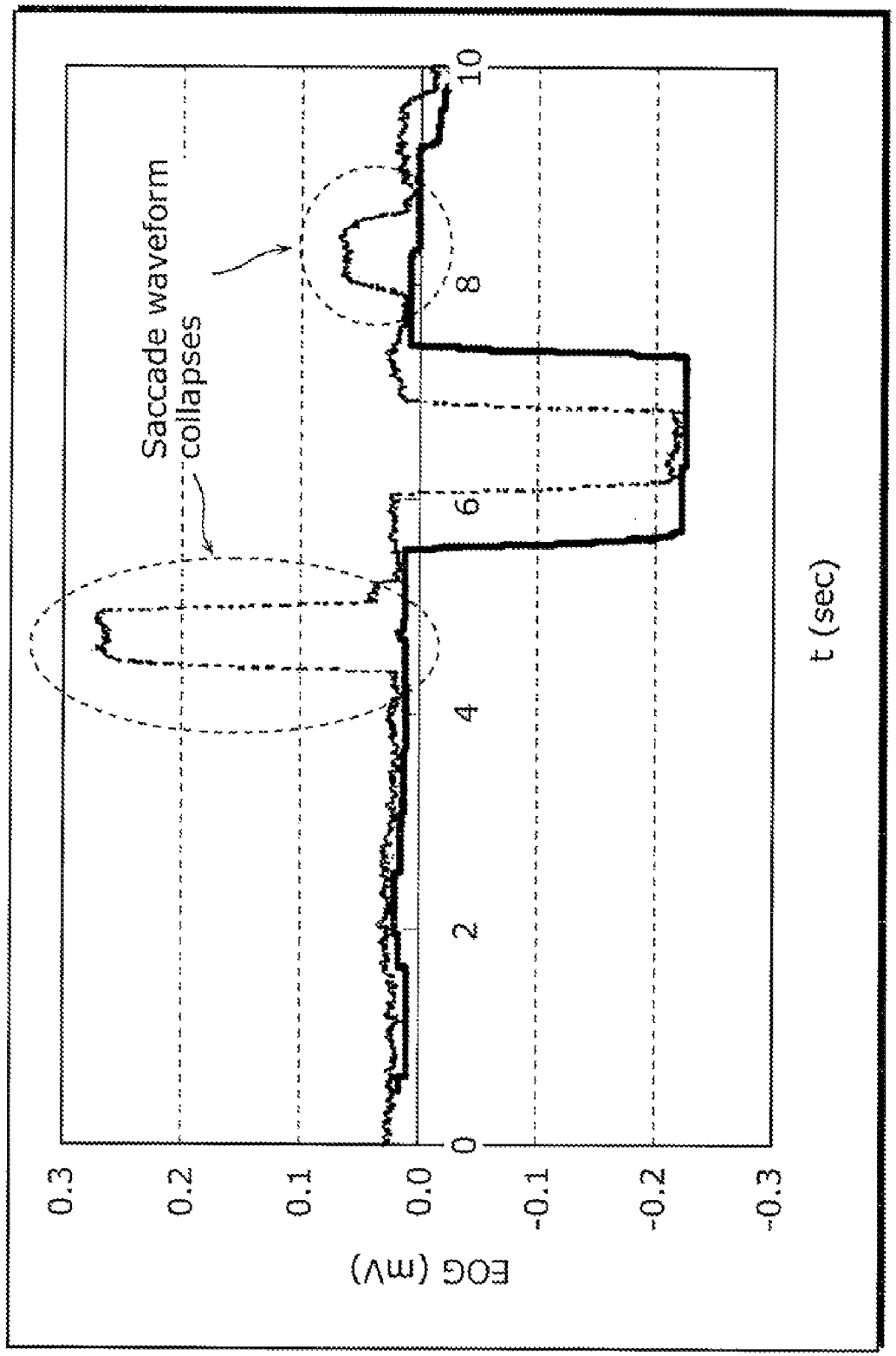
FIG. 29 is a diagram showing an electro-oculography signal obtained by applying minimum value filtering (unit processing period=1.0 second) to the electro-oculography signal in FIG. 23.

As shown in FIG. 28, when the minimum value filtering is performed on the electro-oculography original signal, a plus signal narrows in the temporal direction and a minus signal widens in the temporal direction. Here, when the unit processing period of the minimum value filter unit 502 is set longer than a general single fixation time, the saccade waveform in the plus direction collapses as shown in FIG. 29. FIG. 29 is an example of the minimum value filtering performed with the unit processing period set to 1.0 second. Since the saccade component cannot be detected when the saccade waveform collapses as shown in FIG. 29, it is necessary to make the unit processing period of the minimum value filter unit 502 shorter than the general single fixation time.

It is to be noted that, although the fifth embodiment has shown an example in which the unit processing period of the minimum value filter unit is 0.25 seconds, the unit processing period may be any value as long as it is shorter than the general single fixation time.

Next, the processing of the subtractor 503 will be described. The subtractor 503 subtracts the second electro-oculography signal fmin (x) that is output from the minimum value filter unit 502 from the first electro-oculography signal fmax (x) that is output from the maximum value filter unit 501, to thereby extract the saccade signal.

FIG. 30 shows a signal indicating a difference between the first electro-oculography signal shown in FIG. 26 and the second electro-oculography signal shown in FIG. 28. Referring to FIG. 30, it can be seen that a detection signal including a period of time in which a saccade has occurred is obtained.

The saccade detecting unit 500 generates a saccade detection signal based on an output signal as shown in FIG. 30, and outputs the saccade detection signal to the drift estimating unit 180. For example, when the amount of change in sampled values within a period of time corresponding to a period of time required for saccadic movement is above a predetermined threshold, it is determined that saccadic movement has occurred, and thus a saccade detection signal is output.

It is to be noted that, although the maximum value filter unit 501 and the minimum value filter unit 502 are used in the fifth embodiment, a filter that selects a value close to the maximum value or the minimum value may be used. In this case, it is preferable to use a filter that selects a value approximately 90% of the maximum value or the minimum value.

In addition, although the fifth embodiment has shown an example in which the unit processing periods (the number of filter taps) of the maximum value filter unit 501 and the minimum value filter unit 502 are set to the same value, different values may be set.

According to the configuration of the fifth embodiment as described above, a saccade signal is detected by performing each of the maximum value filtering and the minimum value filtering on the electro-oculography original signal and subtracting the second electro-oculography signal on which the minimum value filtering has been performed from the first electro-oculography signal on which the maximum value filtering has been performed. As a result, it is possible to easily obtain a saccade signal that includes the time at which a saccade has occurred.

Sixth Embodiment

Figure 31:
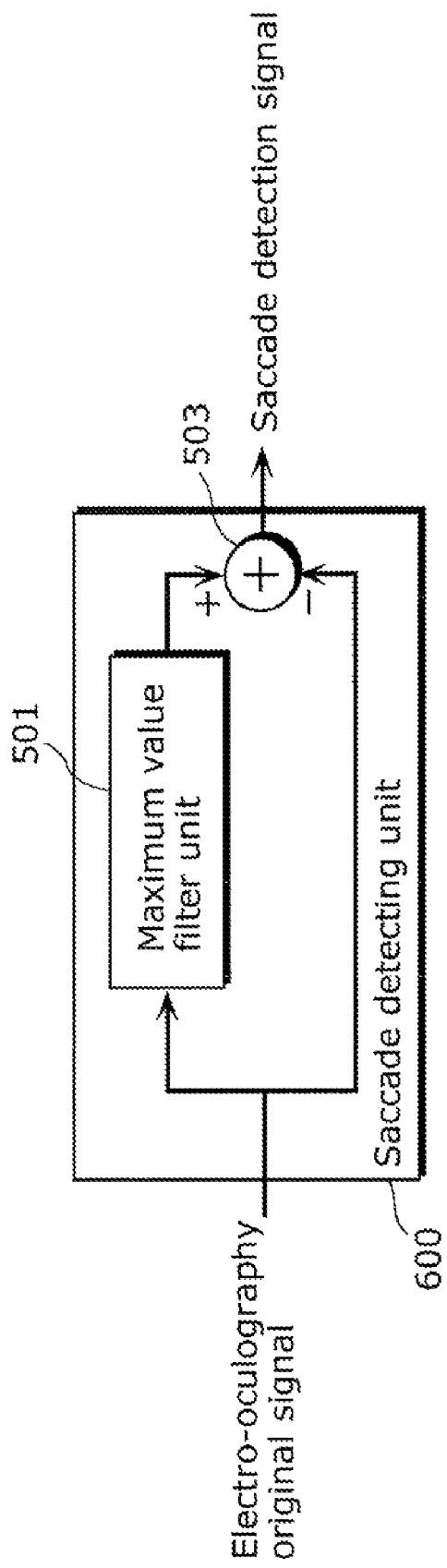
FIG. 31 is a block diagram of a saccade detecting unit according to a sixth embodiment.

FIG. 31 is a block diagram showing a configuration of a saccade detecting unit 600 according to a sixth embodiment of the present invention.

The saccade detecting unit 600 according to the sixth embodiment includes the maximum value filter unit (the first filtering unit) 501 and the subtractor 503. More specifically, it is different from the fifth embodiment in that the minimum value filter unit 502 is omitted. By omitting the minimum value filter unit 502, it is possible to easily obtain a saccade signal while reducing the amount of processing.

The constituent elements in FIG. 31 which are the same as those in FIG. 25 have already been described above, and thus the same reference numerals are assigned and the descriptions thereof will not be repeated. In the saccade detecting unit 600 according to the sixth embodiment, an electro-oculography original signal is branched into two signals. One of the branched signals is input into the subtractor 503 as the first electro-oculography signal via the maximum value filter unit 501, and the other is directly input into the subtractor 503 as the second electro-oculography signal. Then, the subtractor 503 subtracts the electro-oculography original signal f(x) (corresponding to "the second electro-oculography signal") from the first electro-oculography signal fmax (x) on which the maximum value filtering has been performed, so as to output the saccade signal. This is the point different from the fifth embodiment.

Figure 32:
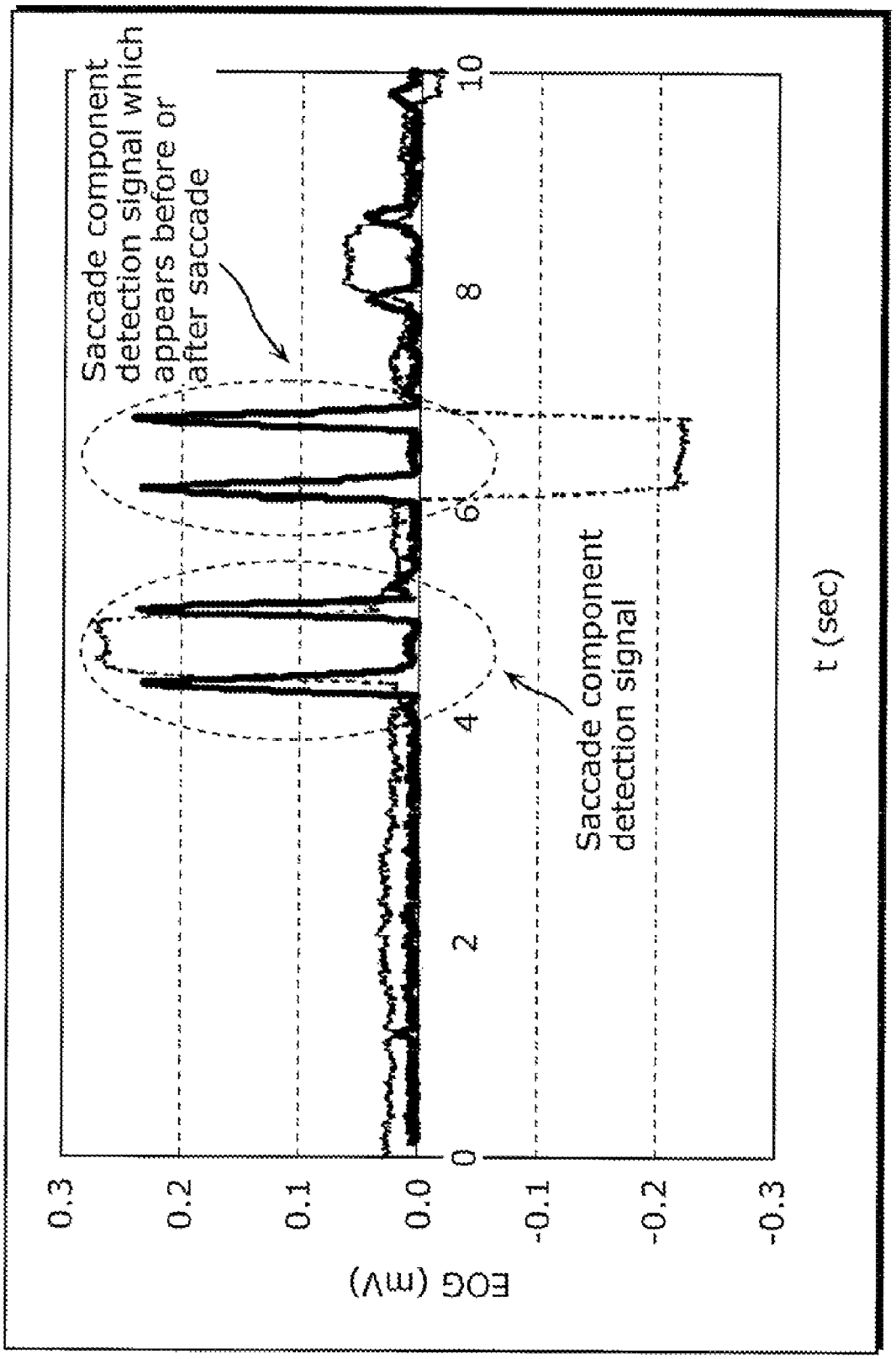
FIG. 32 is a diagram showing a saccade detection signal obtained by subtracting the electro-oculography signal in FIG. 23 from the electro-oculography signal in FIG. 26.

FIG. 32 shows a signal indicating a difference between the first electro-oculography signal on which the maximum value filtering has been performed as shown in FIG. 26 and the electro-oculography original signal shown in FIG. 23. Referring to FIG. 32, it can be seen that the detection signal is obtained when a saccade occurs.

The saccade detecting unit 600 generates a saccade detection signal based on an output signal as shown in FIG. 32, and outputs the saccade detection signal to the drift estimating unit 180. For example, when the amount of change in sampled values within a period of time corresponding to a period of time required for saccadic movement is above a predetermined threshold, it is determined, that saccadic movement has occurred, and thus a saccade detection signal is output.

The saccade component detection signal in the minus direction, however, appears before or after the time at which a saccade occurs. Thus, the sixth embodiment is effective in terms of the processing amount when an occurrence frequency and the like of a saccade, which does not require temporal information, is to be obtained.

It is to be noted that, although the maximum value filter unit 501 is used in the sixth embodiment, a filter that selects a value close to the maximum value may be used. In this case, it is preferable to use a filter that selects a value approximately 90% of the maximum value.

According to the configuration of the sixth embodiment as described above, it is possible to easily obtain a saccade signal because the saccade signal is detected by subtracting an electro-oculography original signal from the first electro-oculography signal obtained by performing the maximum value filtering on the electro-oculography original signal.

Seventh Embodiment

Figure 33:
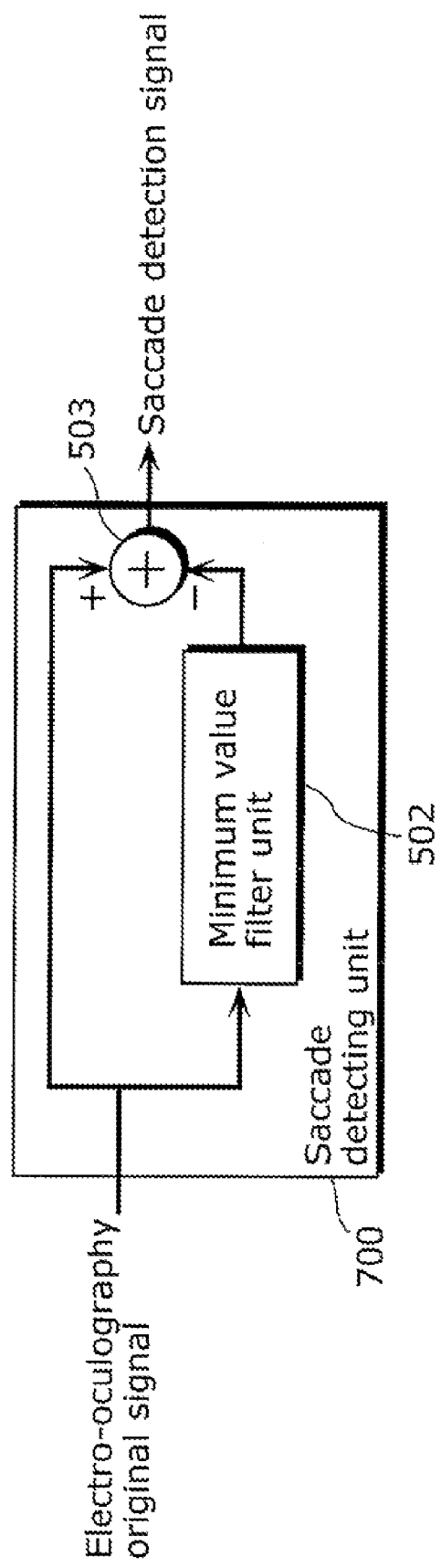
FIG. 33 is a block diagram of a saccade detecting unit according to a seventh embodiment.

FIG. 33 is a block diagram showing a configuration of a saccade detecting unit 700 according to a seventh embodiment of the present invention.

The saccade detecting unit 700 according to the seventh embodiment includes the minimum value filter unit (the first filtering unit) 502 and the subtractor 503. More specifically, it is different from the fifth embodiment in that the maximum value filter unit 501 is omitted. By omitting the maximum value filter unit 501, it is possible to easily obtain a saccade signal while reducing the amount of processing.

The constituent elements in FIG. 33 which are the same as those in FIG. 25 have already been described above, and thus the same reference numerals are assigned and the descriptions thereof will not be repeated. In the saccade detecting unit 700 according to the seventh embodiment, an electro-oculography original signal is branched into two signals. One of the branched signals is input into the subtractor 503 as the first electro-oculography signal via the minimum value filter unit 502, and the other is directly input into the subtractor 503 as the second electro-oculography signal. Then, the subtractor 503 subtracts the first electro-oculography signal fmin (x) on which the minimum value filtering has been performed from the electro-oculography original signal f(x) (corresponding to "the second electro-oculography signal"), so as to output the saccade signal. This is the point different from the fifth embodiment.

Figure 34:
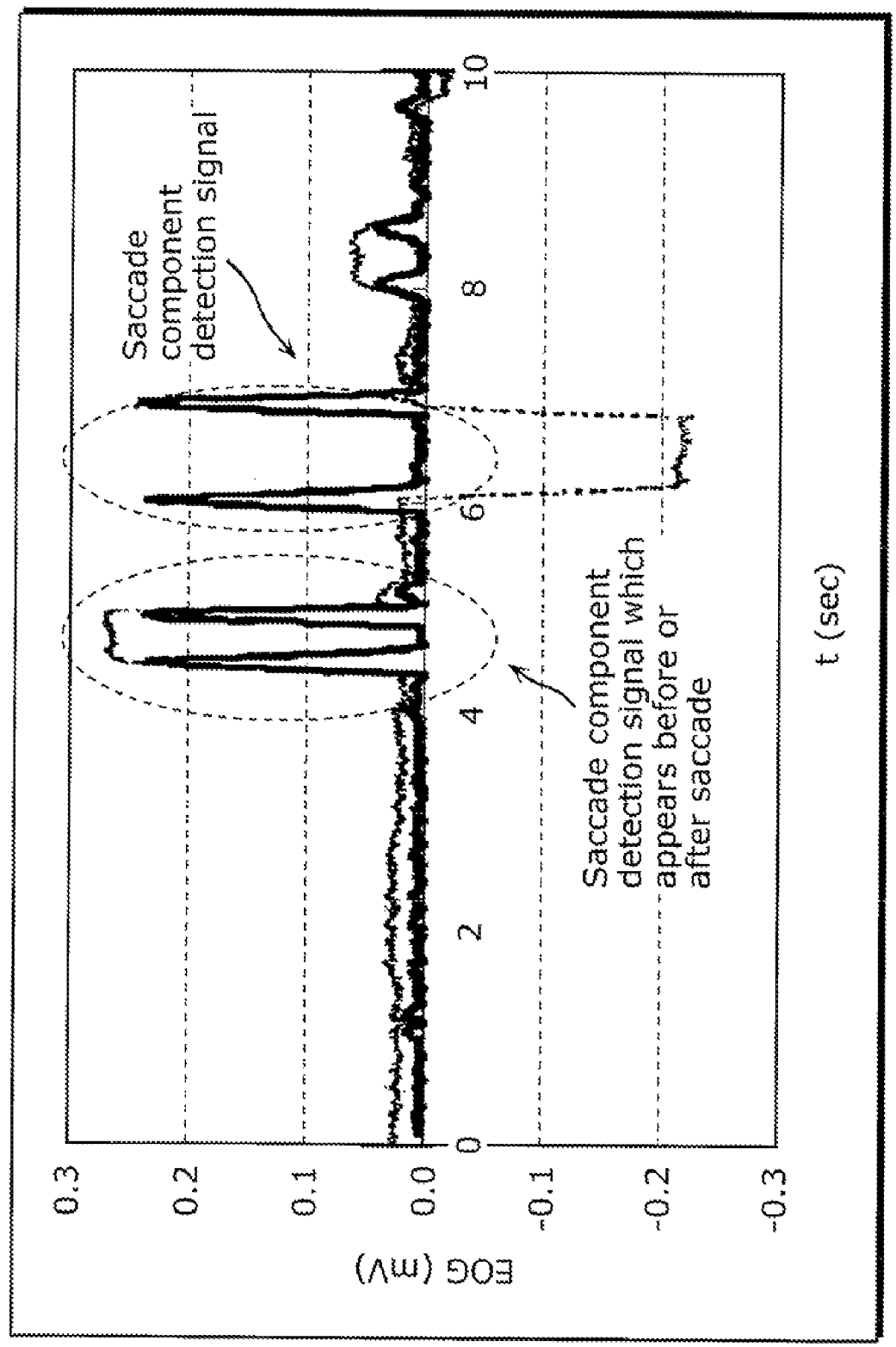
FIG. 34 is a diagram showing a saccade detection signal obtained by subtracting the electro-oculography signal in FIG. 28 from the electro-oculography signal in FIG. 23.

FIG. 34 shows a signal indicating a difference between the electro-oculography original signal shown in FIG. 23 and the second electro-oculography signal on which the minimum value filtering has been performed as shown in FIG. 28. Referring to FIG. 34, it can be seen that the detection signal is obtained when a saccade occurs.

The saccade detecting unit 700 generates a saccade detection signal based on an output signal as shown in FIG. 34, and outputs the saccade detection signal to the drift estimating unit 180. For example, when the amount of change in sampled values within a period of time corresponding to a period of time required for saccadic movement is above a predetermined threshold, it is determined that saccadic movement has occurred, and thus a saccade detection signal is output.

The saccade signal in the plus direction, however, appears before or after the time at which a saccade occurs. Thus, the seventh embodiment is effective in terms of the processing amount when an occurrence frequency and the like of a saccade, which does not require temporal information, is to be obtained.

It is to be noted that, although the minimum value filter unit 502 is used in the seventh embodiment, a filter that selects a value close to the minimum value may be used. In this case, it is preferable to use a filter that selects a value approximately 90% of the minimum value.

According to the configuration of the seventh embodiment as described above, it is possible to easily obtain a saccade signal because the saccade signal is detected by subtracting, from the electro-oculography original signal (the second electro-oculography signal), the first electro-oculography signal obtained by performing the minimum value filtering on the electro-oculography original signal.

Eighth Embodiment

Figure 35:
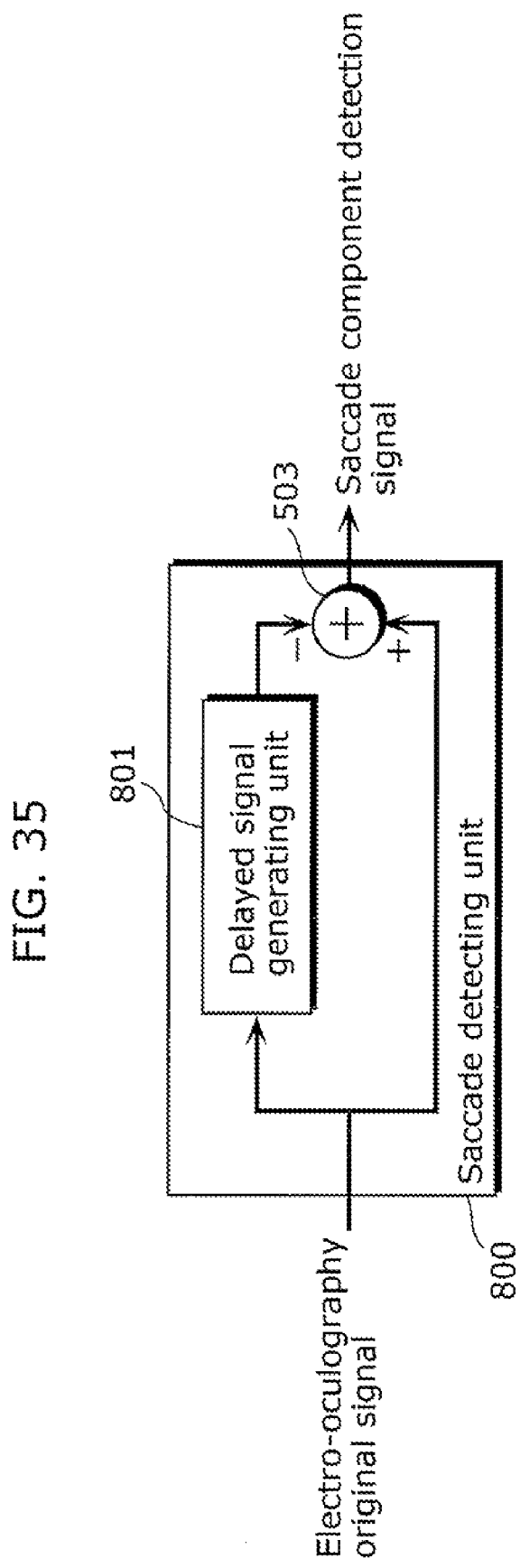
FIG. 35 is a block diagram of a saccade detecting unit according to an eighth embodiment.

Next, FIG. 35 shows a block diagram of a saccade detecting unit 800 according to an eighth embodiment.

The saccade detecting unit 800 according to the eighth embodiment includes a delayed signal generating unit 801 and the subtractor 503. The delayed signal generating unit 801 delays an electro-oculography original signal for a predetermined time period to output a delayed signal. In addition, an electro-oculography original signal input into the saccade detecting unit 800 is branched into two signals. One of the branched signals is input into the subtractor 503 as the delayed signal via the delayed signal generating unit 801, and the other is directly input into the subtractor 503. Then, the subtractor 503 subtracts the delayed signal from the electro-oculography original signal to output a saccade signal. It is possible to easily obtain a plus or minus signed saccade signal by including the delayed signal generating unit 801.

Processing performed by the delayed signal generating unit 801 as shown in FIG. 35 will be described next. The delayed signal, generating unit 801 performs the following processing on an electro-oculography original signal f(x).

$$f\text{delay}(x) = f(x-t)$$

Figure 36:
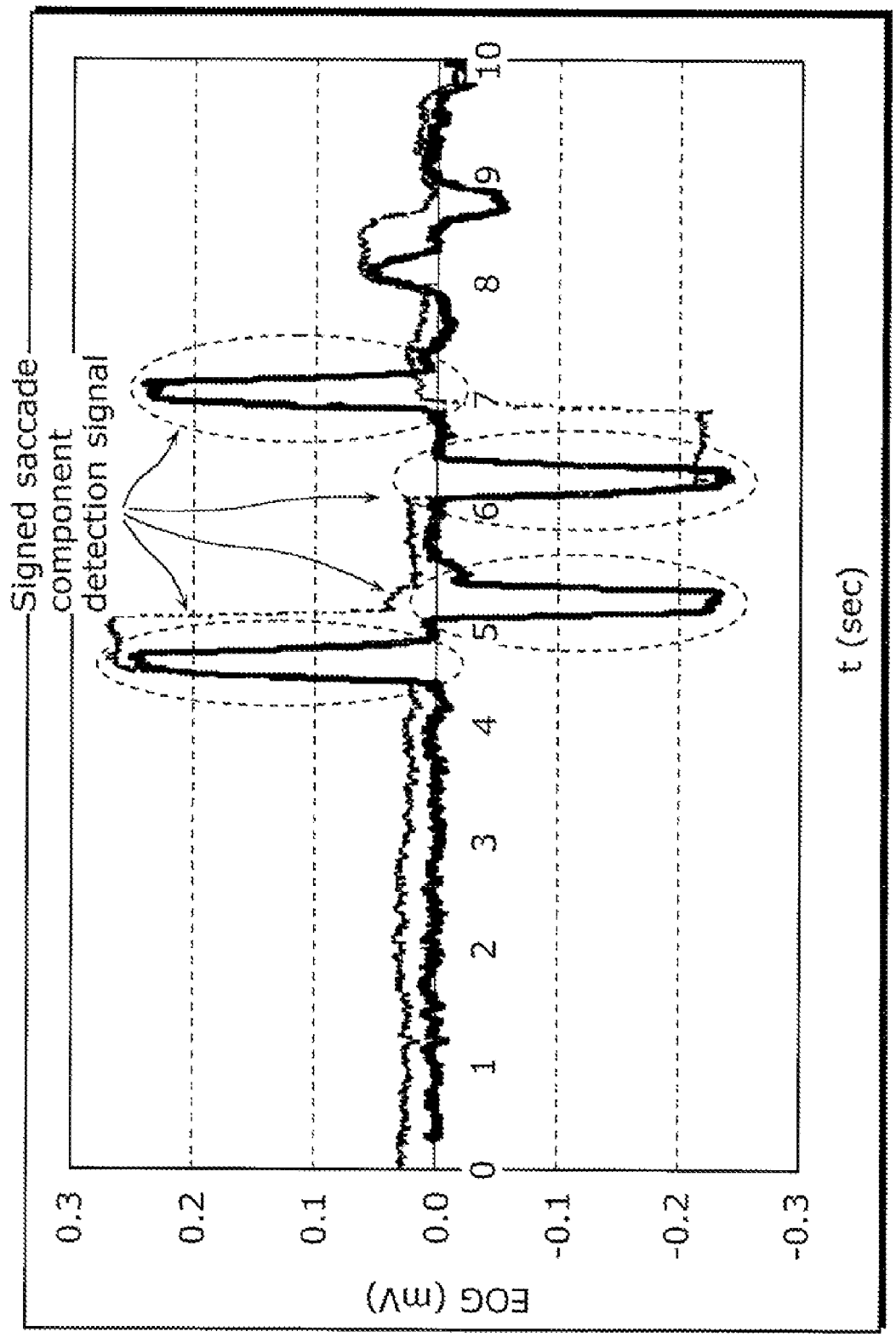
FIG. 36 is a diagram showing a saccade detection signal when a delay time of a delayed signal generating unit is 0.25 seconds.

Here, fdelay (x) is an electro-oculography signal after the delay processing (delayed signal), and t is a delay time. The delayed signal can be obtained by performing the delay processing described above on the electro-oculography original signal shown in FIG. 23. FIG. 36 shows an example where the subtractor 503 subtracts the delayed signal from the electro-oculography original signal. It is to be noted that to detect a signed saccade component from an electro-oculography original signal, the delay time t is set to 0.25 seconds. Referring to FIG. 36, it can be seen that the signed saccade signal including a period of time in which a saccade has occurred is obtained.

The saccade detecting unit 800 generates a saccade detection signal based on an output signal as shown in FIG. 36, and outputs the saccade detection signal to the drift estimating unit 180. For example, when the amount of change in sampled values within a period of time corresponding to a period of time required for saccadic movement is above a predetermined threshold, it is determined that saccadic movement has occurred, and thus a saccade detection signal is output.

Figure 37:
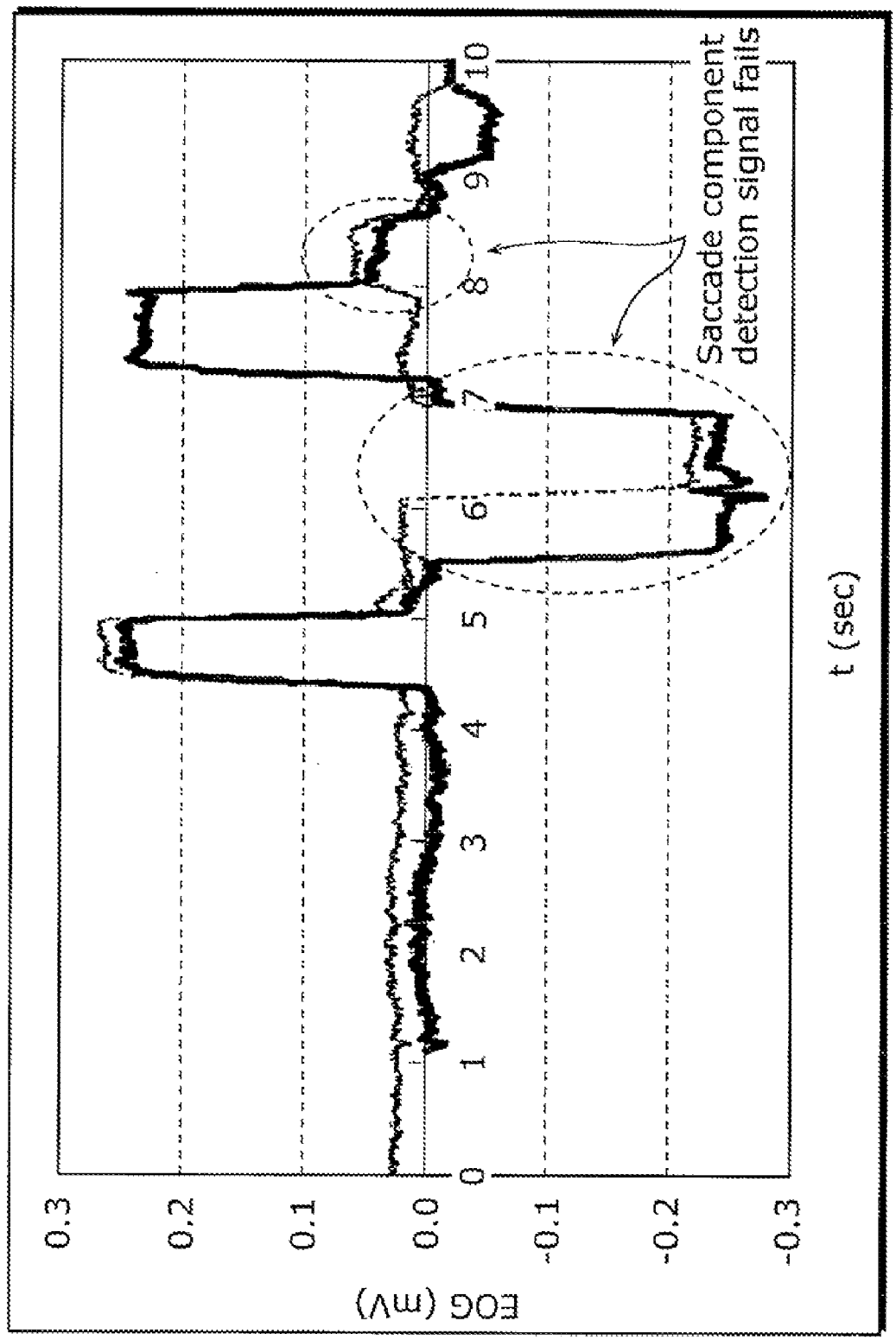
FIG. 37 is a diagram showing a saccade detection signal when a delay time of a delayed signal generating unit is 1.1 seconds.

Here, when the delay time t is set longer than a general single fixation time=(approximately 0.3 to 0.4 seconds), the saccade signal fails as shown in FIG. 37. FIG. 37 is an example where the delay time t is 1.1 seconds. When the saccade signal fails as shown in FIG. 37, the saccade signal cannot be extracted. Thus, it is necessary to make the delay time t of the delayed signal generating unit 801 shorter than the general single fixation time. It is to be noted that, although the eighth embodiment has shown an example where the delay time is 0.25 seconds, it may be any value as long as it is shorter than the general single fixation time.

The configuration of the eighth embodiment as described above is effective in making it possible to distinguish between a plus and a minus saccade signal, because a signed saccade signal is detected by generating a delayed signal from an electro-oculography original signal and subtracting the delayed signal from the electro-oculography original signal.

Next, a method of measuring an electro-oculogram in consideration of an influence of blink will be described. When detecting eyeball movement by utilizing a change in electro-oculogram as in the EOG method and the like, there is a problem of an influence of a signal generated by a blink of a user (hereinafter referred to as "blink signal").

In some cases, the blink signal is generated invariably in the plus direction, or invariably in the minus direction, depending on the method of measuring the electro-oculogram. FIG. 38A to FIG. 38D show examples of attachment patterns of the electro-oculography measuring unit and the methods of measuring the electro-oculography original signal.

With the attachment pattern shown in FIG. 38A, the electrodes A and B are attached above and below an eye, respectively, and a difference potential Va−Vb is obtained, where Va is an electro-oculogram measured by the electrode A attached above the eye and Vb is an electro-oculogram measured by the electrode B attached below the eye. In this case, the blink signal is generated invariably in the plus direction. This is because, when a human blinks, the eyeball always moves upward.

Figure 38A:
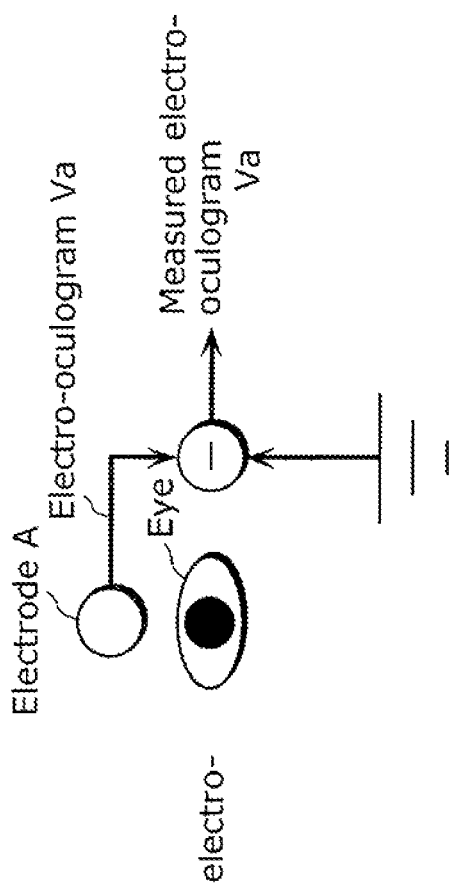
FIG. 38A is a diagram showing an example of an electrode attachment pattern.
Figure 38B:
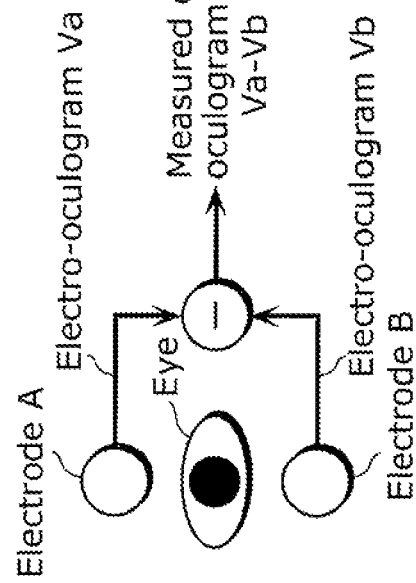
FIG. 38B is a diagram showing another example of an electrode attachment pattern.

With the attachment pattern shown in FIG. 38B, the electrode A is attached above the eye and the other electrode is attached to the earth or a place less subject to the electro-oculogram, so as to measure the electro-oculogram Va from the electrode A. In this case also, the blink signal is generated invariably in the plus direction (at a value larger than a reference value).

Likewise, with the attachment pattern shown in FIG. 38C, the electrodes A and B are attached above and below the eye, respectively, and a difference potential Vb−Va is obtained, where Vb is an electro-oculogram measured by the electrode B attached below the eye and Va is an electro-oculogram measured by the electrode A attached above the eye. In this case, the blink signal is generated invariably in the minus direction. With the attachment pattern shown in FIG. 38D, the electrode B is attached below the eye and the other electrode is attached to the earth or a place less subject to the electro-oculogram, so as to measure the electro-oculogram Vb from the electrode B. In this case also, the blink signal is generated invariably in the minus direction.

Figure 39:
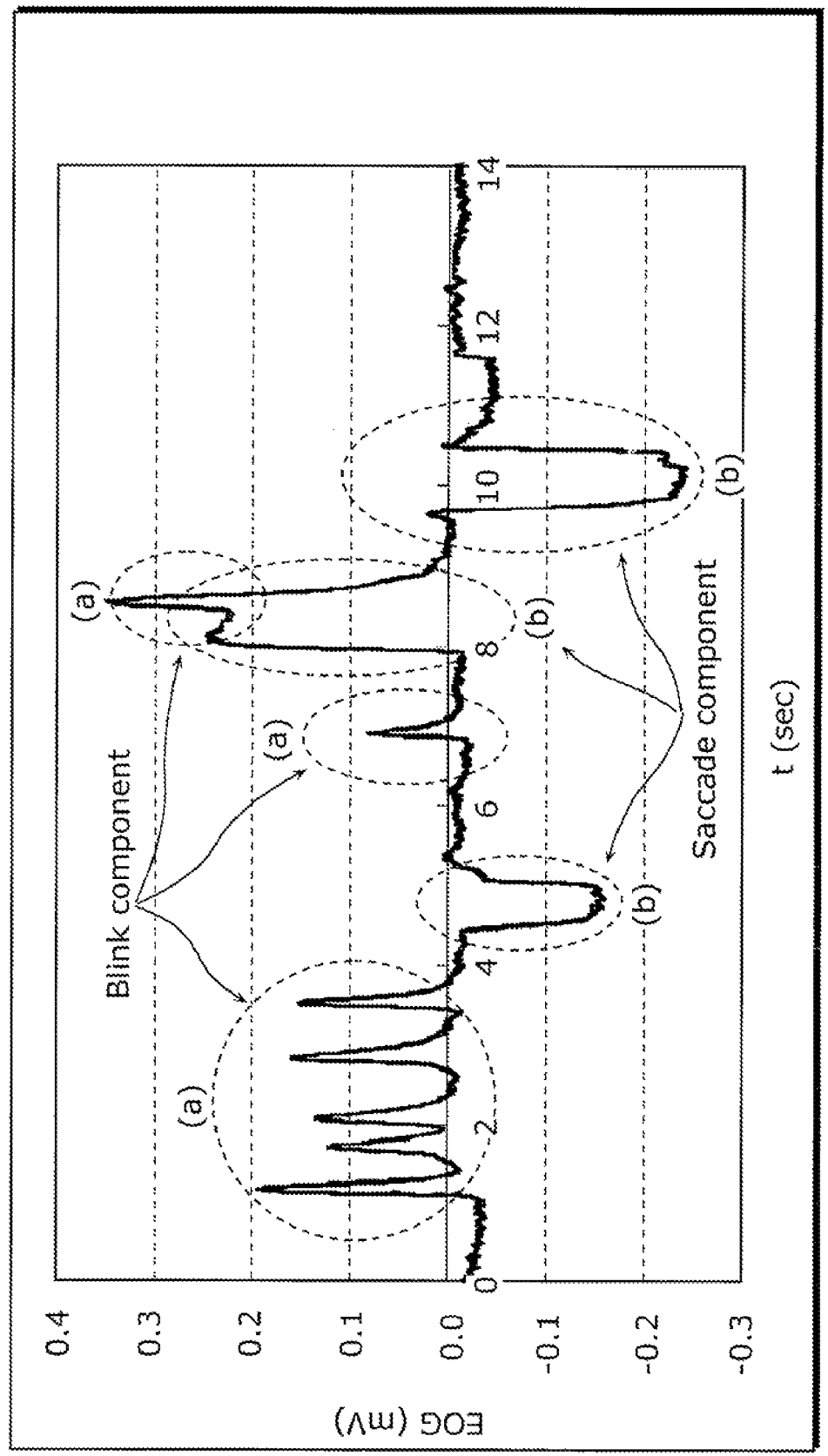
FIG. 39 is a diagram showing an example of an electro-oculography signal that includes a blink signal.

When the user blinks during the measurement with the attachment patterns shown in FIG. 38A and FIG. 38B, a steep potential is generated in the plus direction (this is the "blink signal") as shown in regions (a) in FIG. 39. When the blink signal is directly used for detecting a gaze position, the gaze position changes rapidly and the gaze path cannot be tracked accurately.

In view of the above, there is a technique disclosed in Japanese Unexamined Patent Application Publication No. 11-85384 (Patent Literature 6) as a method to reduce the influence of the blink signal (a component of a signal generated by a blink) and the like from an electro-oculography original signal.

The technique disclosed in Patent Literature 6 aims to detect an electro-oculogram of a user and to input a gaze position (cursor) in real time. In doing so, a delay element is introduced into a fluctuating waveform of the electro-oculogram, so that temporal variations in the gaze position (cursor) are smoothed and a rapid change in the gaze position caused by a blink is reduced.

In addition, there is a technique disclosed in "Full-time Wearable Headphone-Type Gaze Detector", Interaction 2006, pages 23-24, 2006 (Non-Patent Literature 1), Hiroyuki Manabe and Masaaki Fukumoto, as a technique of reducing the influence of the blink signal.

According to the technique disclosed in Non-Patent Literature 1, a total of eight electrodes are attached to the right and left of a headphone. To changes in the electro-oculograms obtained from the eight electrodes, a median filter is applied at 0.4 second intervals to remove a blink signal shorter than 0.4 seconds.

However, as in the method disclosed in Patent Literature 6, merely temporally smoothing the electro-oculography original signal causes an adverse effect that the smoothing is performed even on a saccade waveform indicating a change in component of a saccade (rapid movement of a human eye from one gaze point to another (saccadic movement)) that is important in tracking a gaze path.

Figure 40:
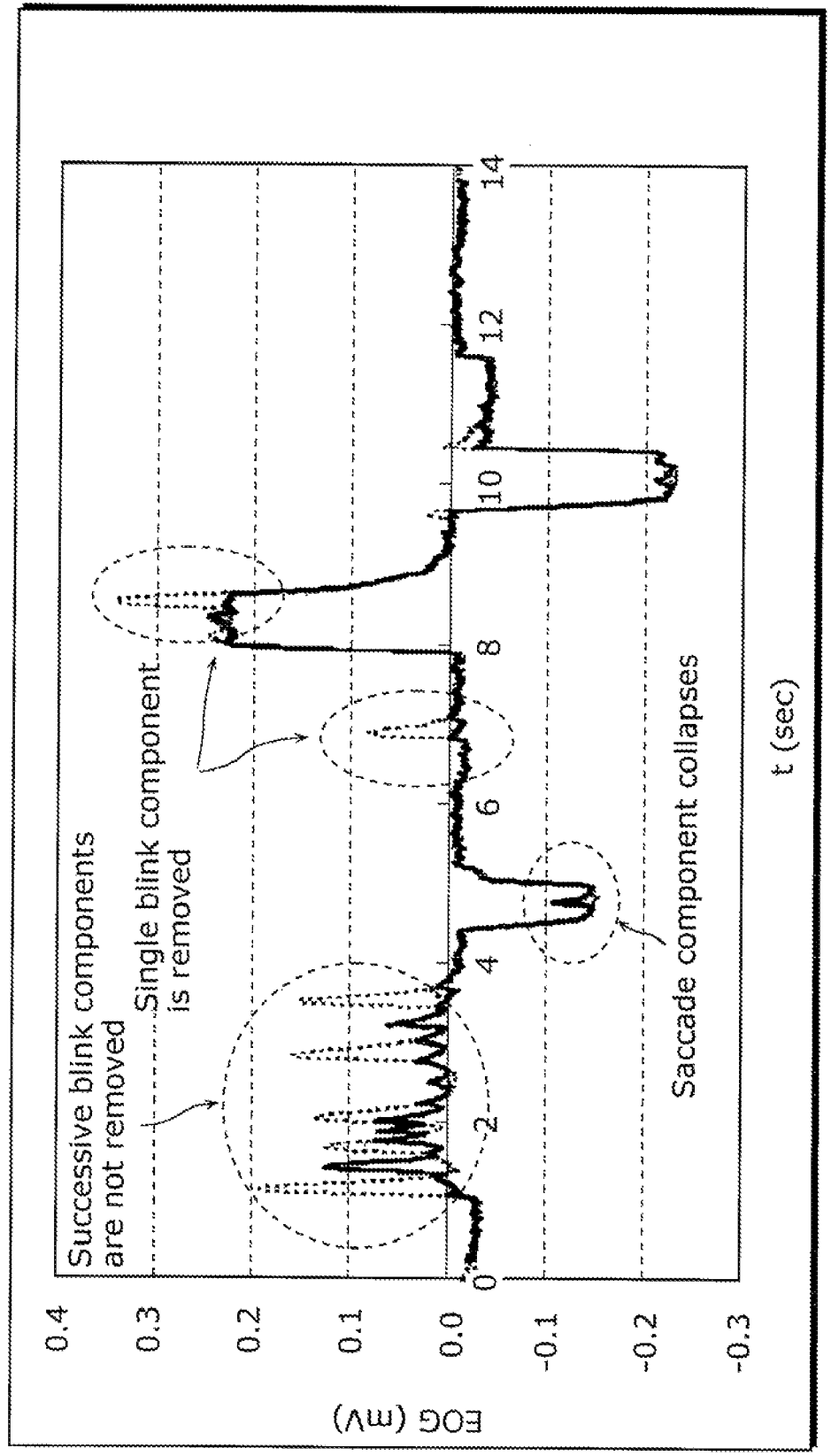
FIG. 40 is a diagram showing an electro-oculography signal obtained by applying a median filter to the electro-oculography signal in FIG. 39.

Moreover, when a median filter is applied to the electro-oculography original signal as disclosed in Non-Patent Literature 1, a singly-generated blink signal can be removed, but the influence of blink signals generated successively for a predetermined time period or longer cannot be completely removed as shown in FIG. 40. In addition, there is an adverse effect that part of the saccade waveform collapses.

In other words, the above-mentioned literatures have not made it clear what kind of smoothing filter should be applied for how long and in what order to produce an optimum outcome, in consideration of the removal of the blink signal and retaining of the saccade signal.

Thus, in ninth through eleventh embodiments, a method of easily and accurately removing or detecting a blink signal from an electro-oculography original signal of a user and further detecting a saccade signal will be described. It is to be noted that although the following description shows an example of removing or detecting a blink signal from an electro-oculography original signal including a drift signal, which is obtained from the electrodes attached to the user, the same description can be applied to the case where a blink signal is removed or detected from an electro-oculography signal from which a drift signal has been removed as described in the first through fourth embodiments.

Ninth Embodiment

Figure 41:
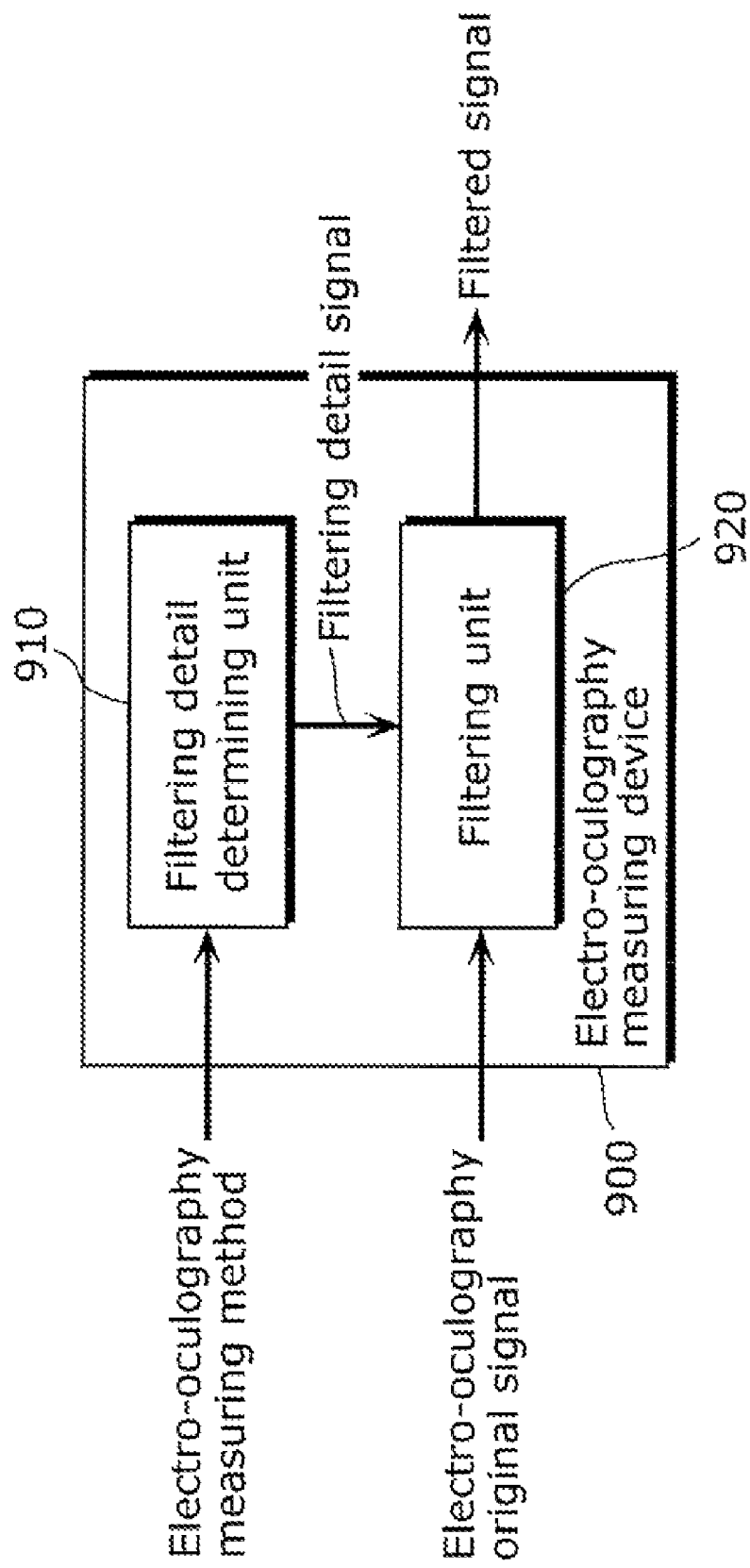
FIG. 41 is a block diagram of an electro-oculography measuring device according to a ninth embodiment.

FIG. 41 is a block diagram showing a configuration of an electro-oculography measuring device 900 according to a ninth embodiment of the present invention.

The electro-oculography measuring device 900 includes: an electro-oculography measuring unit (illustration omitted) attached near a user's eye to measure an electro-oculogram and output an electro-oculography original signal; a filtering detail determining unit 910 that determines the details of filtering based on a signal indicating a method of measuring electro-oculogram (in the diagram: electro-oculography measuring method); and a filtering unit 920 that filters the electro-oculography original signal according to a filtering detail signal which is output from the filtering detail determining unit 910.

First, the electro-oculography measuring method may be specified in advance by an experimenter or a user, or may be estimated based on a pattern of change in the electro-oculography original signal.

More specifically, the user may specify that the measuring method is a method in which the electrodes A and B are respectively attached to the right and left of an eyeball as shown in FIGS. 64A and 64B. In addition, in the case where an upward signal is generated in the electro-oculography original signal whenever the user blinks, it may be estimated that the measuring method is a method for which the attachment patterns shown in FIG. 38A and FIG. 38B are employed.

Figure 42:
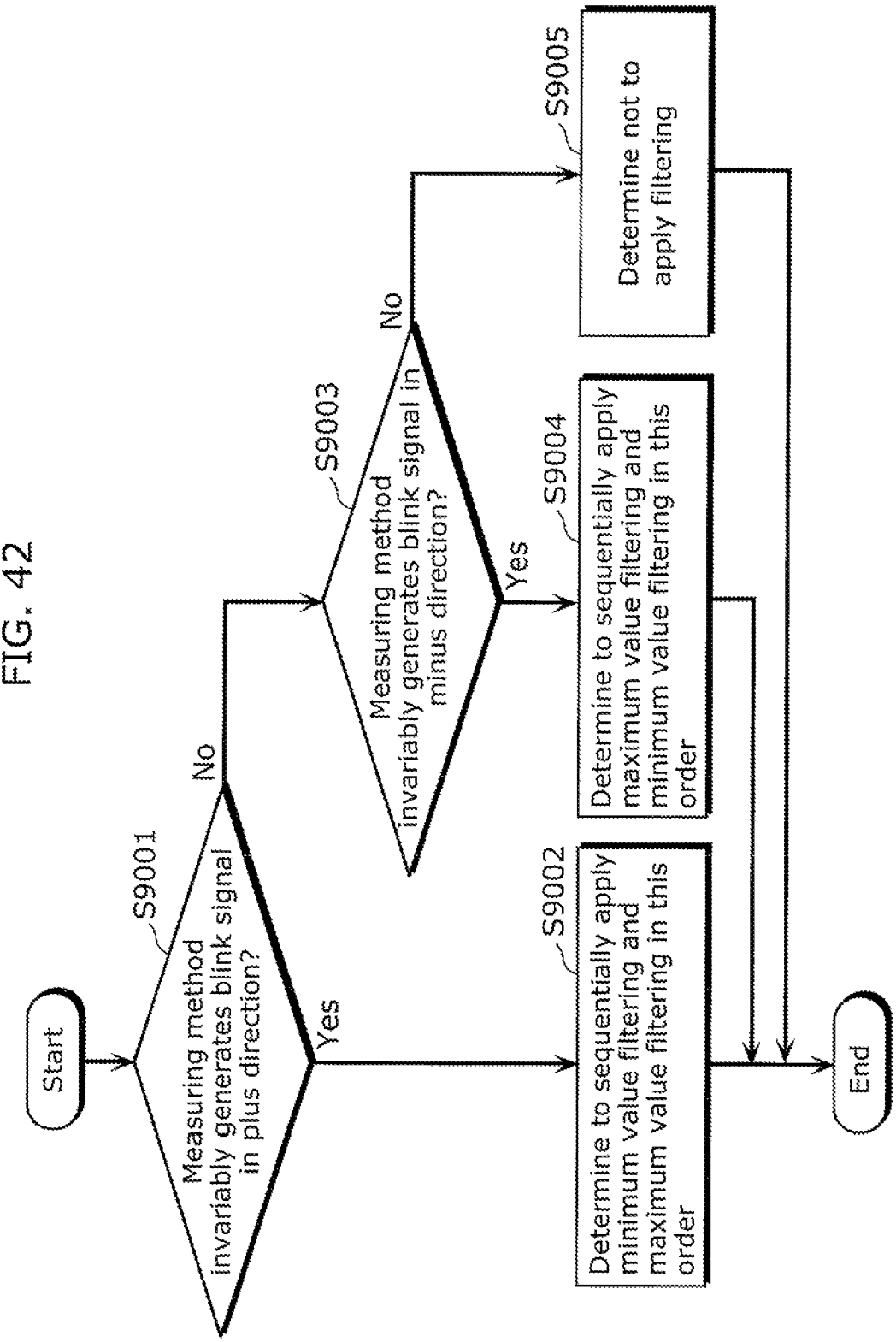
FIG. 42 is a flow chart showing an operation of a filtering detail determining unit.

FIG. 42 is a flow chart showing a filtering detail determining operation of the filtering detail determining unit 910. The filtering detail determining unit 910 first determines an order in which the filtering unit 920 applies filters (described later) to remove an influence of blink. Although not shown, the number of necessary taps (time) is also determined according to the difference in electro-oculography measuring methods. Furthermore, whether or not a filter is to be applied is changed depending on whether the electrodes attached in advance are attached in the horizontal direction or in the vertical direction.

Specifically, it is determined whether or not the measuring method is a method which invariably generates a blink signal in the plus direction as in the case of the attachment patterns in FIG. 38A and FIG. 38B (Step S9001). When the blink signal invariably indicates a plus potential (Yes in Step S9001), the filtering details are determined so that the minimum value filtering and the maximum value filtering are performed in this order (Step S9002).

Figure 38C:
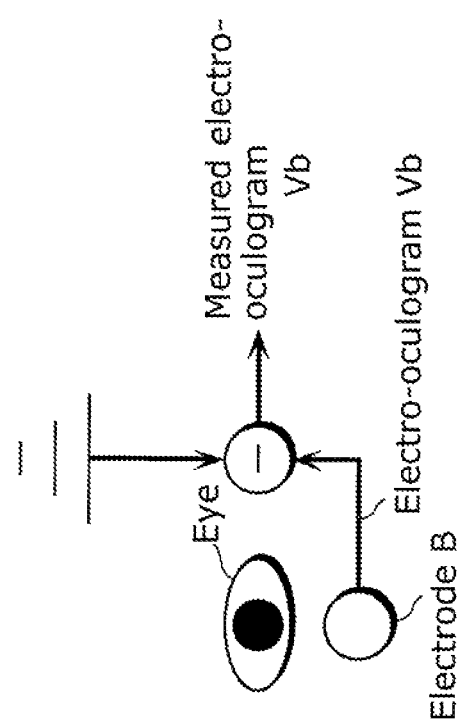
FIG. 38C is a diagram showing another example of an electrode attachment pattern.
Figure 38D:
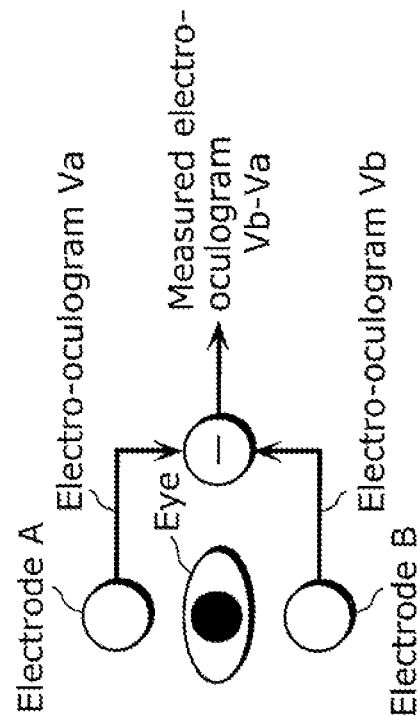
FIG. 38D is a diagram showing another example of an electrode attachment pattern.

When the blink signal does not indicate a plus potential (No in Step S9001), it is determined whether or not the measuring method is a method which invariably generates the blink signal in the minus direction as in the case of the attachment patterns in FIG. 38C and FIG. 38D (Step S9003). When the blink signal invariably indicates a minus potential (Yes in Step S9003), the filtering details are determined so that the maximum value filtering and the minimum value filtering are performed in this order (Step S9004).

When the blink signal does not indicate a minus potential (No in Step S9003), it is determined that the measuring method is not affected by blink, and it is thus determined that the filtering for the blink signal removal is not to be performed (Step S9005). It is to be noted that examples of the case where the measuring method is not affected by blink include the case where the electrodes A and B are attached to the right and left of an eye, respectively, as shown in FIG. 64A and FIG. 64B, to measure a difference in the electro-oculograms obtained, and the case where the electrodes A and B are attached away from the eye.

The filtering detail determining unit 910 outputs a filtering detail signal (order, the number of taps n, and whether or not filtering is to be performed (n=0 may be output)) by including information such as the filter application order determined in the above process, the number of taps n of the filter, and unit processing period. It is to be noted that the order of the determination in the above-described flow chart is a mere example, and any other determination order may be employed.

Figure 43:
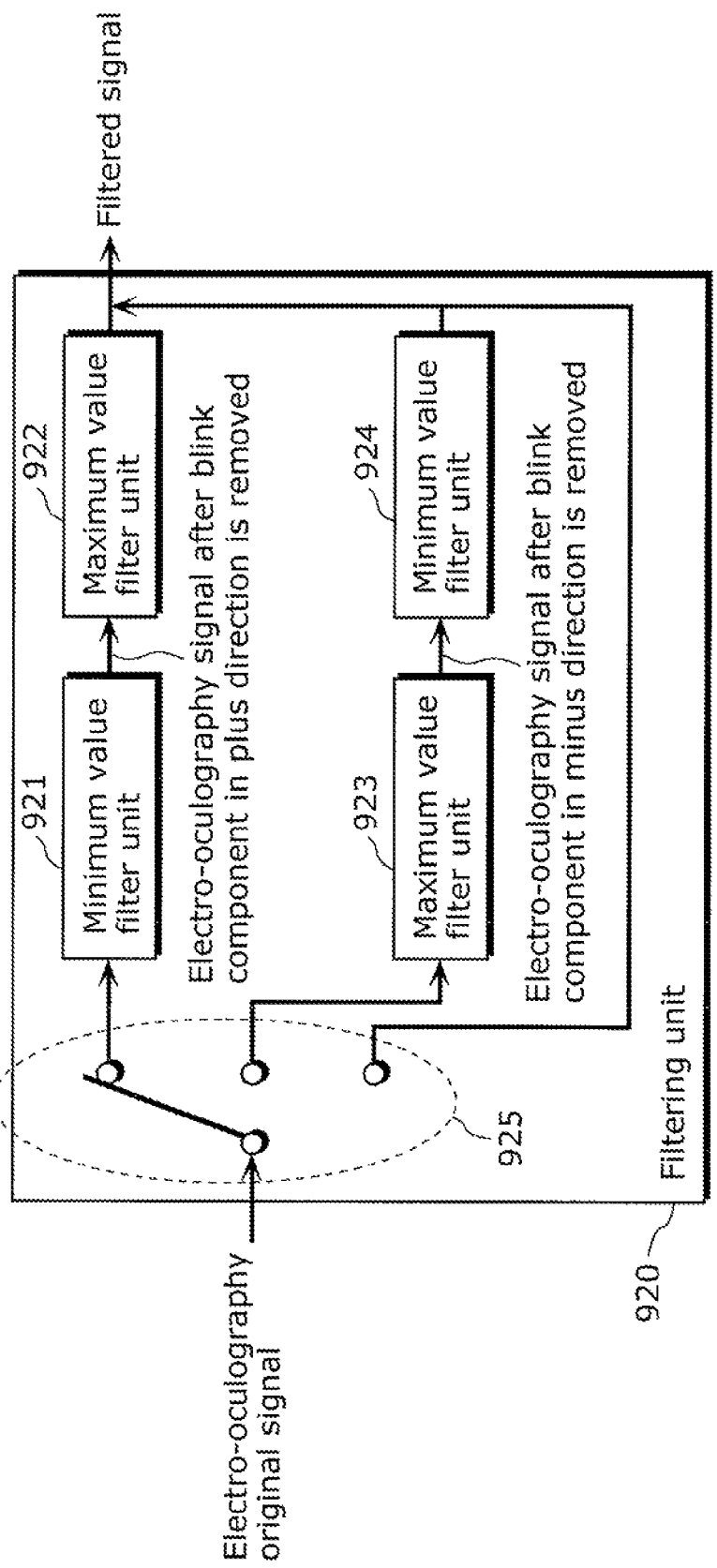
FIG. 43 is a block diagram of a filtering unit in FIG. 41.

FIG. 43 is a diagram showing a configuration of the filtering unit 920. The filtering unit 920 filters the electro-oculography original signal according to the filtering detail signal that is output from the filtering detail determining unit 910.

The filtering unit 920 includes: two minimum value filter units 921 and 924; two maximum value filter units 922 and 923; and a switch 925 that switches among first to third paths connecting an input terminal and an output terminal, so that the electro-oculography original signal is output to the switched path.

Connected to the first path in series are: the minimum value filter unit 921 (the first filtering unit) which performs the minimum value filtering on the electro-oculography original signal to output a first electro-oculography signal; and the maximum value filter unit 922 (the second filtering unit) which performs the maximum value filtering on the first electro-oculography signal to output a second electro-oculography signal (filtered signal). Connected to the second path in series are: the maximum value filter unit 923 (the first filtering unit) which performs the maximum value filtering on the electro-oculography original signal to output a first electro-oculography signal; and the minimum value filter unit 924 (the second filtering unit) which performs the minimum value filtering on the first electro-oculography signal to output a second electro-oculography signal (filtered signal). The third path is a path for outputting the electro-oculography original signal without filtering. The switch 925 switches among the output destinations to which the electro-oculography original signal is to be output, according to the filtering details determined by the filtering detail determining unit 910.

When receiving the filtering detail signal generated in Step S9002 in FIG. 42, the switch 925 switches the connection point to the top connection point shown in FIG. 43, so that the electro-oculography original signal is output to the first path. In addition, when receiving the filtering detail signal generated in Step S9004 in FIG. 42, the switch 925 switches the connection point to the middle connection point shown in FIG. 43, so that the electro-oculography original signal is output to the second path. Furthermore, when receiving the filtering detail signal generated in Step S9005 in FIG. 42, the switch 925 switches the connection point to the bottom connection point shown in FIG. 43, so that the electro-oculography original signal is output to the third path.

It is to be noted that the processing details of the minimum value filter units 921 and 924 and the maximum value filter units 922 and 923 are the same as those described in the fifth embodiment, and thus the descriptions thereof will not be repeated. In addition, although two minimum value filter units 921 and 924 and two maximum value filter units 922 and 923 are provided in the ninth embodiment, there may be a single minimum value filter unit and a single maximum value filter unit, and the connection order may be changed based on the filtering detail signal and the like, to perform the filtering.

Next, processing performed when the electro-oculography original signal is input into the first path will be described. First, FIG. 44 shows the first electro-oculography signal generated by the minimum value filter unit 921 performing the minimum value filtering on the electro-oculography original signal shown in FIG. 39.

It is to be noted that to remove the blink signal from the electro-oculography original signal, the unit processing period of the minimum value filter unit 921 is set to 0.25 seconds according to the value determined with a filtering detail signal.

Figure 44:
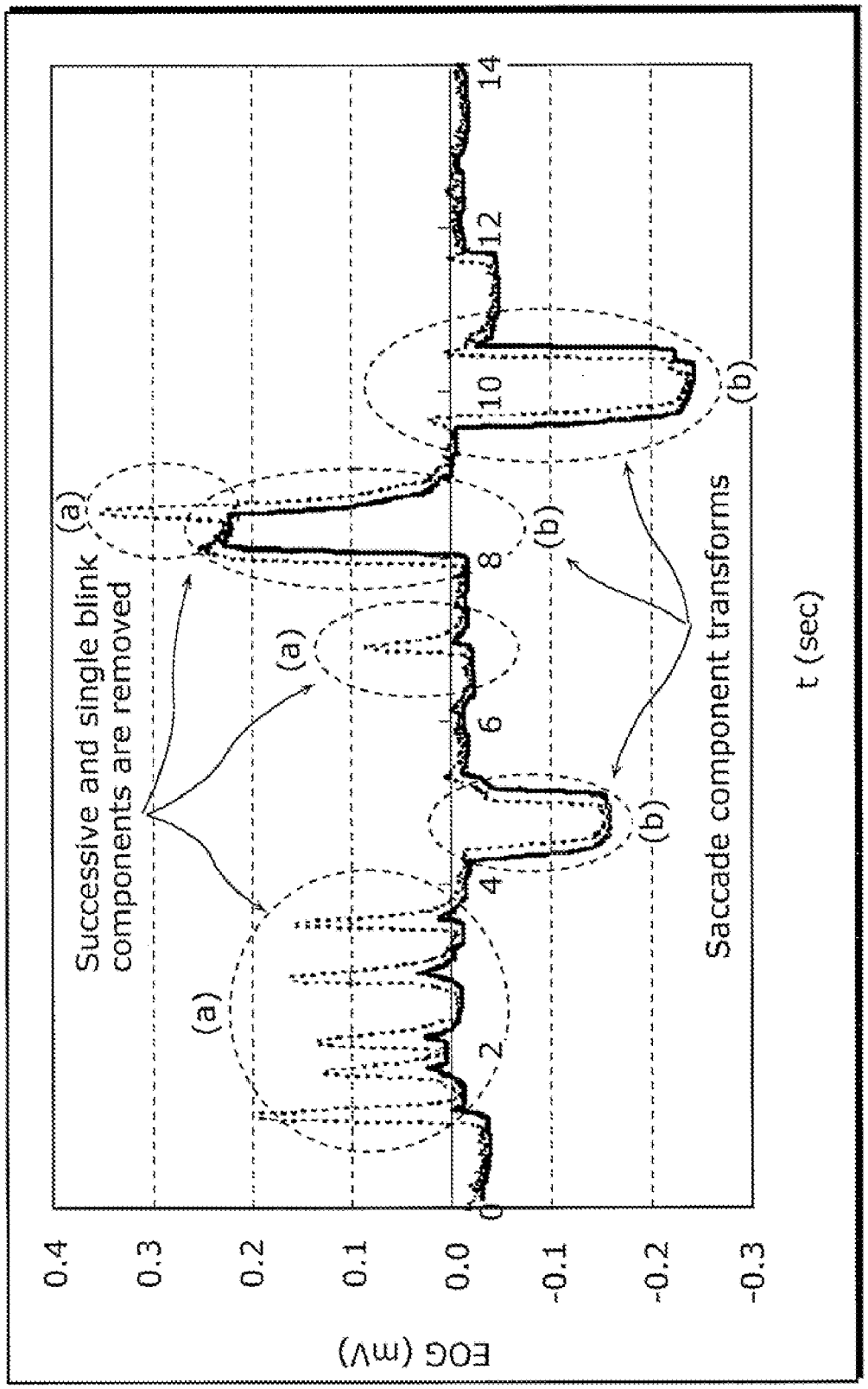
FIG. 44 is a diagram showing an electro-oculography signal obtained by applying minimum value filtering to the electro-oculography signal in FIG. 39.

Referring to regions (a) in FIG. 44, it can be seen that successive blink signals and single blink signals are removed by performing the minimum value filtering on the electro-oculography original signal. However, in the first electro-oculography signal shown in FIG. 44, the saccade waveforms are transformed (increase in the temporal width), which is an adverse effect caused by the minimum value filtering.

It is to be noted that, although the ninth embodiment has shown an example where the minimum value filtering is performed with the unit processing period of the minimum value filter unit 921 set to 0.25 seconds, the unit processing period may be any value as long as it is longer than a general time period of a single blink=(approximately 0.15 seconds to 0.2 seconds) but shorter than a single fixation time=(approximately 0.3 seconds to 0.4 seconds).

Figure 45:
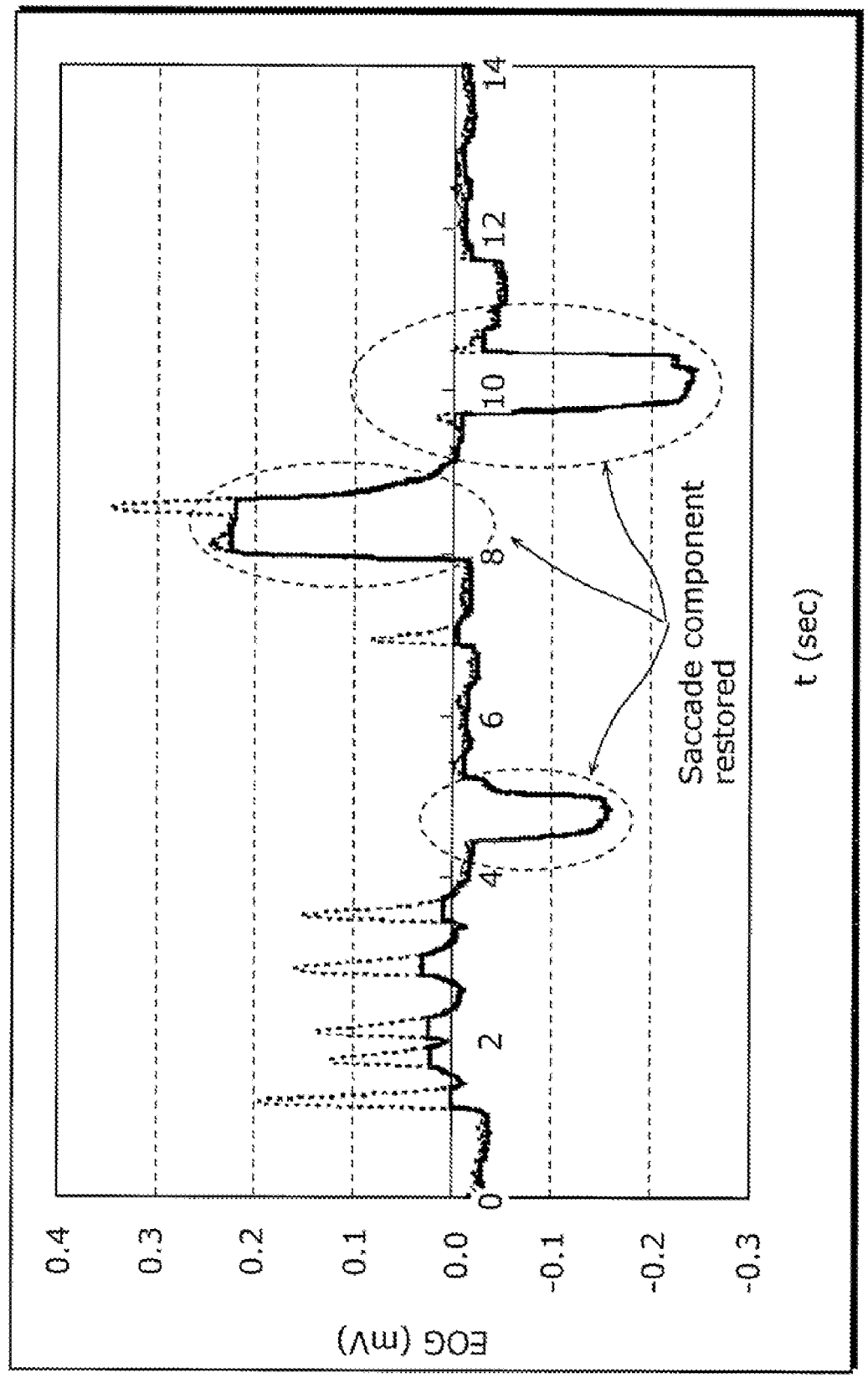
FIG. 45 is a diagram showing an electro-oculography signal obtained by applying maximum value filtering to the electro-oculography signal in FIG. 44.

Next, FIG. 45 shows a second electro-oculography signal (filtered signal) generated by the maximum value filter unit 922 performing the maximum Value filtering on the first electro-oculography signal shown in FIG. 44. It is to be noted that the unit processing period is set to 0.25 seconds as in the case of the minimum value filter unit 921.

As shown in FIG. 45, the transformed saccade waveform as shown in FIG. 44 can be restored to have the width of the original signal waveform through the maximum value filtering performed on the first electro-oculography signal.

The fundamental processes of the maximum value filter unit 923 and the minimum value filter unit 924 are the same as those of the maximum value filter unit 922 and the minimum value filter unit 921, respectively, and it is possible to remove the blink signal in the minus direction without affecting the saccade waveform by performing the maximum value filtering and the minimum value filtering in this order.

It is to be noted that, although the ninth embodiment has shown the example where the minimum value filter units 921 and 924 and the maximum value filter units 922 and 923 are used, a filter that selects a value close to the minimum value or the maximum value may be used. In this case, it is preferable to use a filter that selects a value approximately 90% of the maximum value or the minimum value.

In addition, although the same values are used for the numbers of filter taps of the minimum value filtering and the maximum value filtering in the ninth embodiment, similar but different values may be used. In other words, perfect matching is unnecessary.

In the case of consecutively performing a plurality of filtering processes, it is sufficient if the filtering for removing the influence of the blink signal is performed first, and then the filtering for restoring the temporal waveform of saccade is performed next.

In addition, although the blink signal is removed and the saccade waveform is restored by consecutively performing the minimum value filtering and the maximum value filtering in the ninth embodiment, only one of the minimum value filtering and the maximum value filtering may be performed without departing from the scope of the present invention when the purpose is to only remove the blink signal.

According to the configuration of the ninth embodiment described above, the details of filtering to be performed on an electro-oculography original signal are determined according to the method of measuring the electro-oculography original signal, and the filtering is performed according to the determined details. As a result, it is possible to properly remove a blink signal even when the electrodes are attached in the opposite orientation, for example.

In addition, when the measuring method is such that a blink signal is generated in the plus direction of an electro-oculography original signal, the filtering details are determined so that the minimum value filtering and the maximum value filtering are consecutively performed in this order. As a result, it is possible to restore a saccade waveform while easily removing the blink signal in the plus direction.

In addition, when the measuring method is such that a blink signal is generated in the minus direction of an electro-oculography original signal, the filtering details are determined so that the maximum value filtering and the minimum value filtering are consecutively performed in this order. As a result, it is possible to restore a saccade waveform while easily removing the blink signal in the minus direction.

The electro-oculography measuring device 900 having the above-described configuration can be applied to the electro-oculography measuring device 100 shown in FIG. 1. For example, the electro-oculography signal that is output from the subtractor 120 is input into the electro-oculography measuring device 900 as an electro-oculography original signal, and the filtered signal that is output from the electro-oculography measuring device 900 is input to the saccade detecting unit 130, the electro-oculography change amount calculating unit 140, and the drift change amount estimating unit 170 shown in FIG. 1 as an electro-oculography signal. This eliminates the need to take a blink signal into consideration in the saccade detecting unit 130, the electro-oculography change amount calculating unit 140, and the drift change amount estimating unit 170 even when the electro-oculography measuring device 900 measures an electro-oculography signal including a blink signal.

Tenth Embodiment

Figure 46:
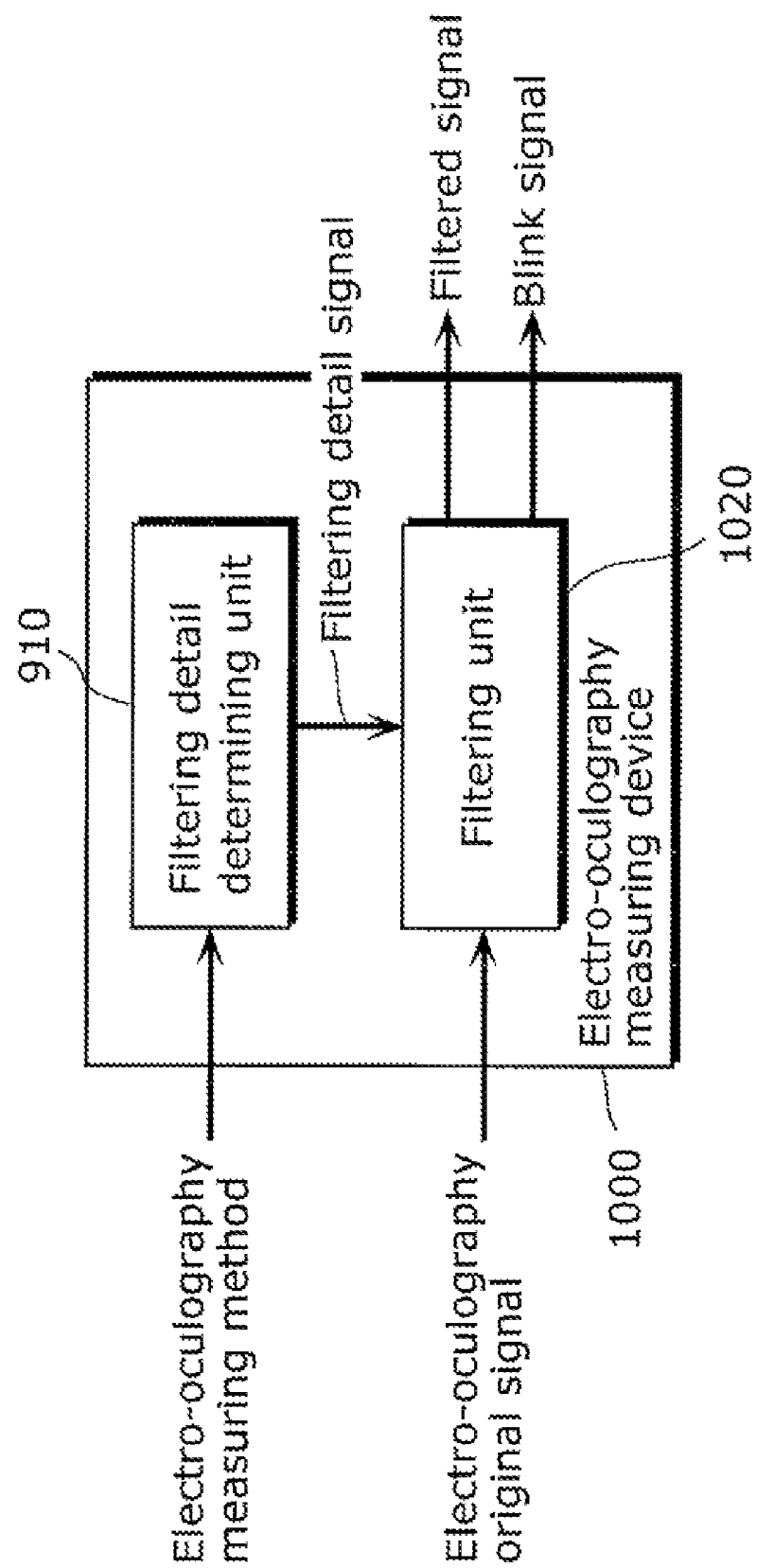
FIG. 46 is a block diagram of an electro-oculography measuring device according to a tenth embodiment.
Figure 47:
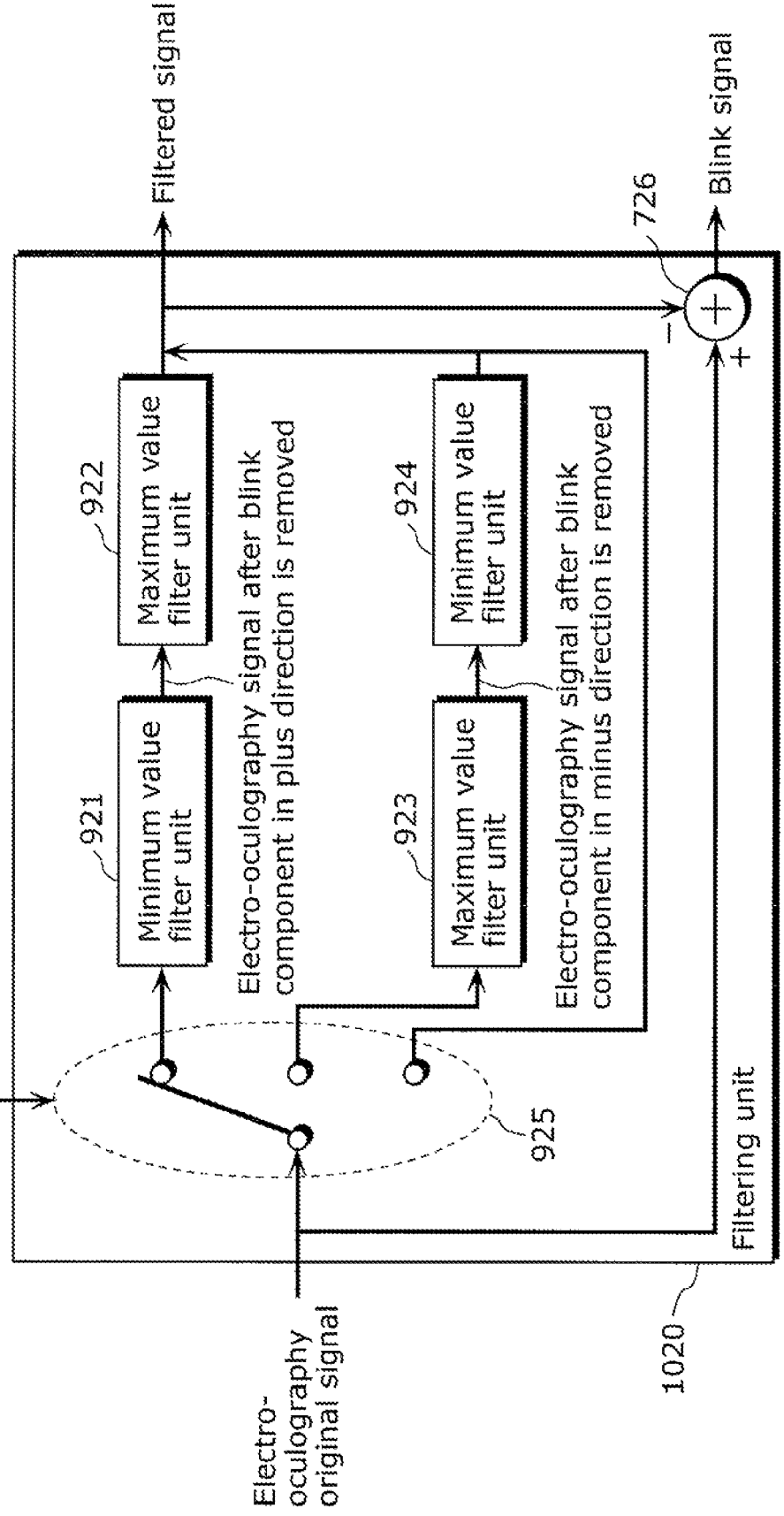
FIG. 47 is a block diagram of a filtering unit in FIG. 46.

FIG. 46 and FIG. 47 are block diagrams showing a configuration of an electro-oculography measuring device 1000 according to a tenth embodiment of the present invention.

The tenth embodiment differs from the ninth embodiment in that a filtering unit 1020 includes a subtractor 1026 that subtracts a filtered electro-oculography signal from an electro-oculography original signal. The inclusion of the subtractor 1026 makes it possible to output a blink signal in addition to the filtered signal.

FIG. 47 is a block diagram showing an example of the filtering unit 1020 in the electro-oculography measuring device 1000 according to the tenth embodiment. It is to be noted that the same constituent elements as those in FIG. 43 have already been described, and thus the same reference numerals are assigned and the descriptions thereof will not be repeated.

The subtractor 1026 outputs a difference between the electro-oculography original signal and the filtered signal. The difference is a blink signal.

Figure 48:
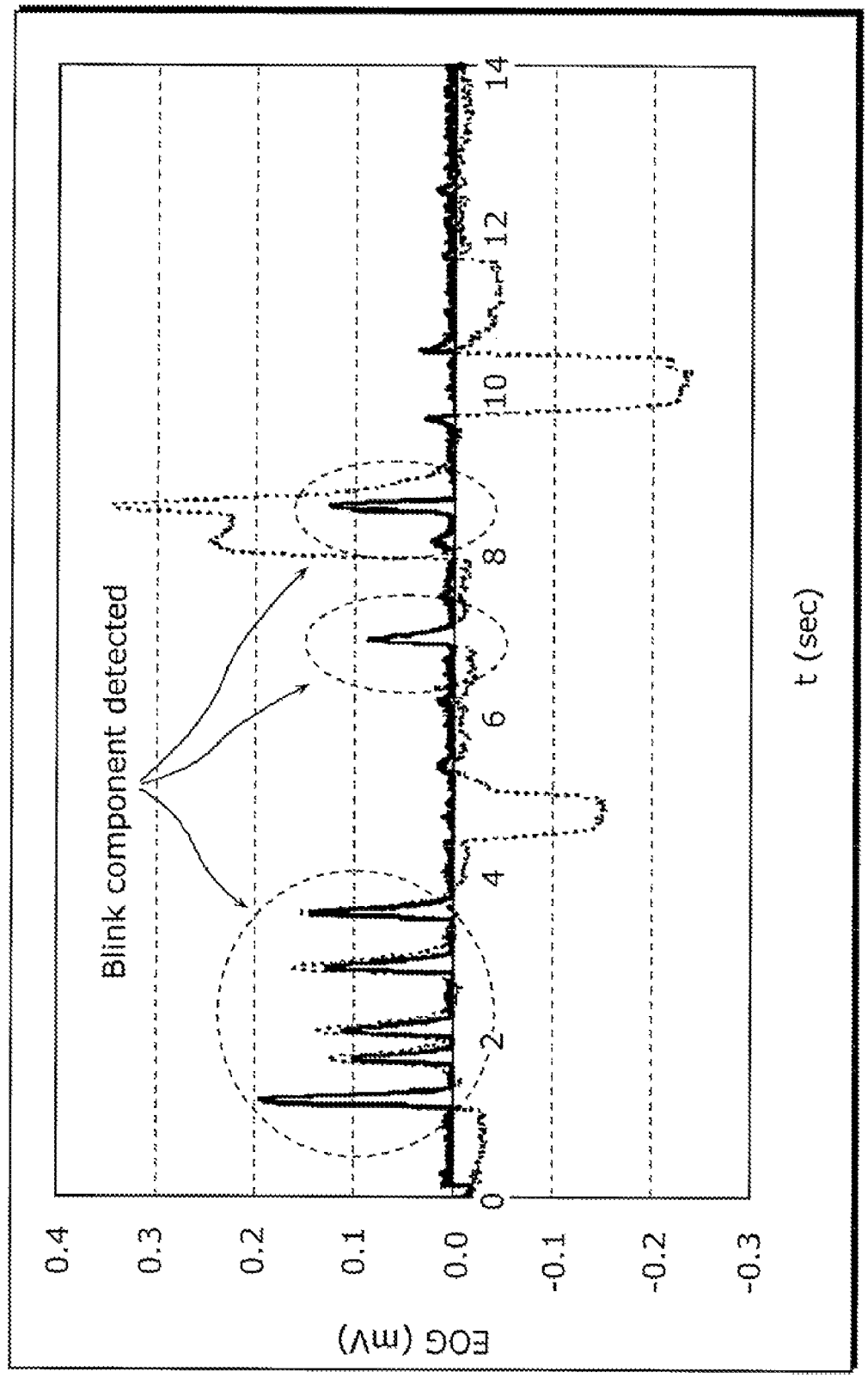
FIG. 48 is a diagram showing a blink signal obtained by inputting the electro-oculography signal in FIG. 44 into the filtering unit in FIG. 47.

FIG. 48 shows a blink signal obtained by subtracting the second electro-oculography signal in FIG. 45 from the electro-oculography original signal in FIG. 39. Referring to FIG. 48, it can be seen that only the blink signal is detected from the electro-oculography original signal.

According to the configuration of the tenth embodiment described above, the details of filtering to be performed on an electro-oculography original signal are determined according to the method of measuring the electro-oculography original signal, and suitable filtering is performed according to the determined details. As a result, it is possible to detect a blink signal regardless of the measuring method employed.

In addition, when the measuring method is such that a blink signal is generated in the plus direction of an electro-oculography original signal, the filtering details are determined so that the minimum value filtering and the maximum value filtering are consecutively performed in this order. As a result, it is possible to restore a saccade component while easily detecting a blink signal in the plus direction.

Furthermore, when the measuring method is such that a blink signal is generated in the minus direction of an electro-oculography original signal, the filtering details are determined so that the maximum value filtering and the minimum value filtering are consecutively performed in this order. As a result, it is possible to restore a saccade component while easily detecting a blink signal in the minus direction.

Eleventh Embodiment

Figure 49:
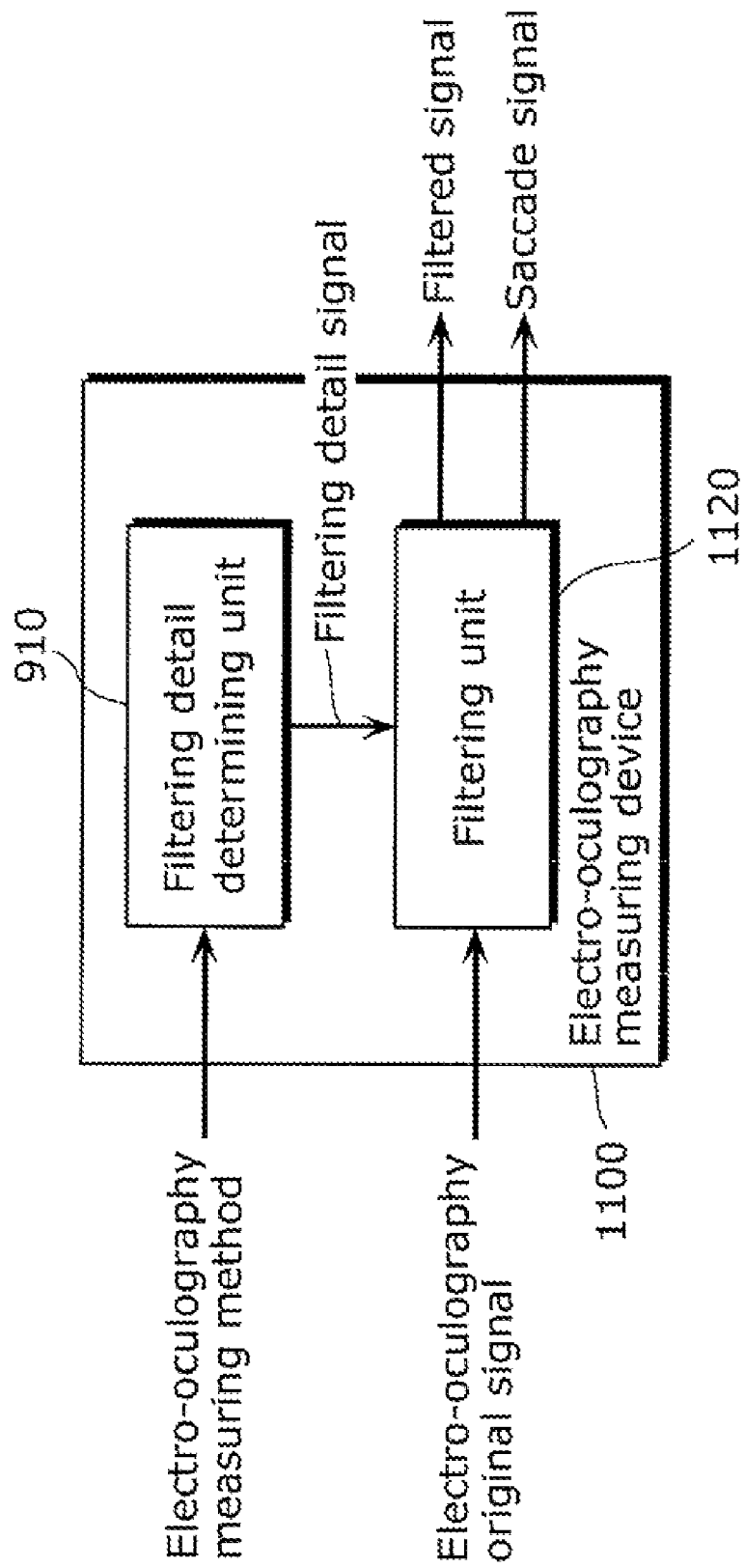
FIG. 49 is a block diagram of an electro-oculography measuring device according to an eleventh embodiment.
Figure 50:
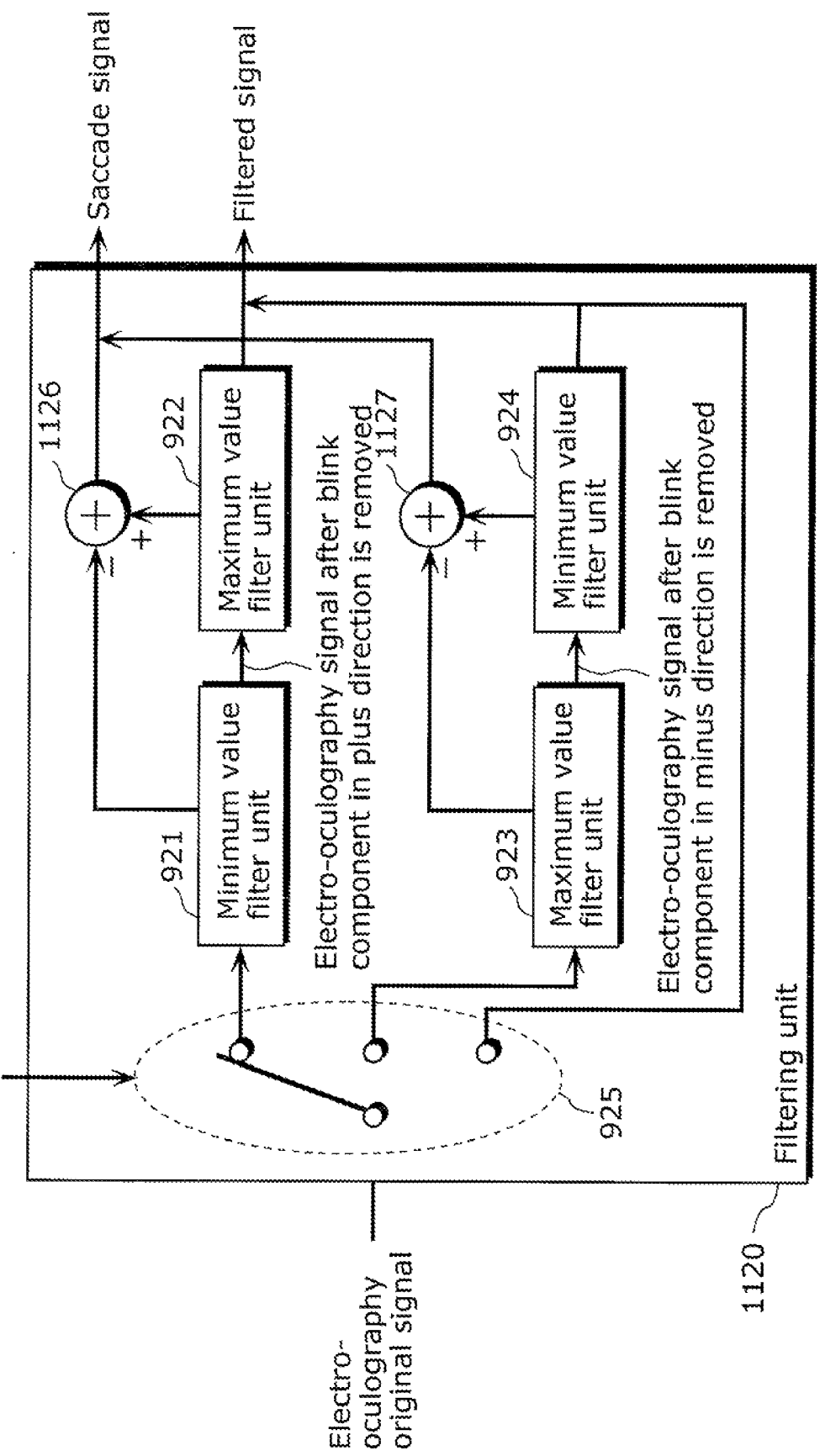
FIG. 50 is a block diagram of a filtering unit in FIG. 49.

FIG. 49 and FIG. 50 are block diagrams showing a configuration of an electro-oculography measuring device 1100 according to an eleventh embodiment of the present invention.

The eleventh embodiment differs from the ninth embodiment in that a filtering unit 1120 includes subtractors 1126 and 1127 which subtract a signal on which one of the maximum value filtering and the minimum value filtering has been performed (a first electro-oculography signal) from a signal on which both the maximum value filtering and the minimum value filtering have been performed (a second electro-oculography signal). The inclusion of the subtractors 1126 and 1127 makes it possible to output a saccade signal in addition to the filtered signal.

FIG. 50 is a block diagram showing an example of the filtering unit 1120 in the electro-oculography measuring device 1100 according to the eleventh embodiment. It is to be noted that the same constituent elements as those in FIG. 43 have already been described, and thus the same reference numerals are assigned and the descriptions thereof will not be repeated.

The subtractor 1126 subtracts an output signal of the minimum value filter unit 921 from an output signal of the maximum value filter unit 922, so as to output a saccade signal. Likewise, the subtractor 1127 subtracts an output signal of the maximum value filter unit 923 from an output signal of the minimum value filter unit 924, so as to output a saccade signal.

Figure 51:
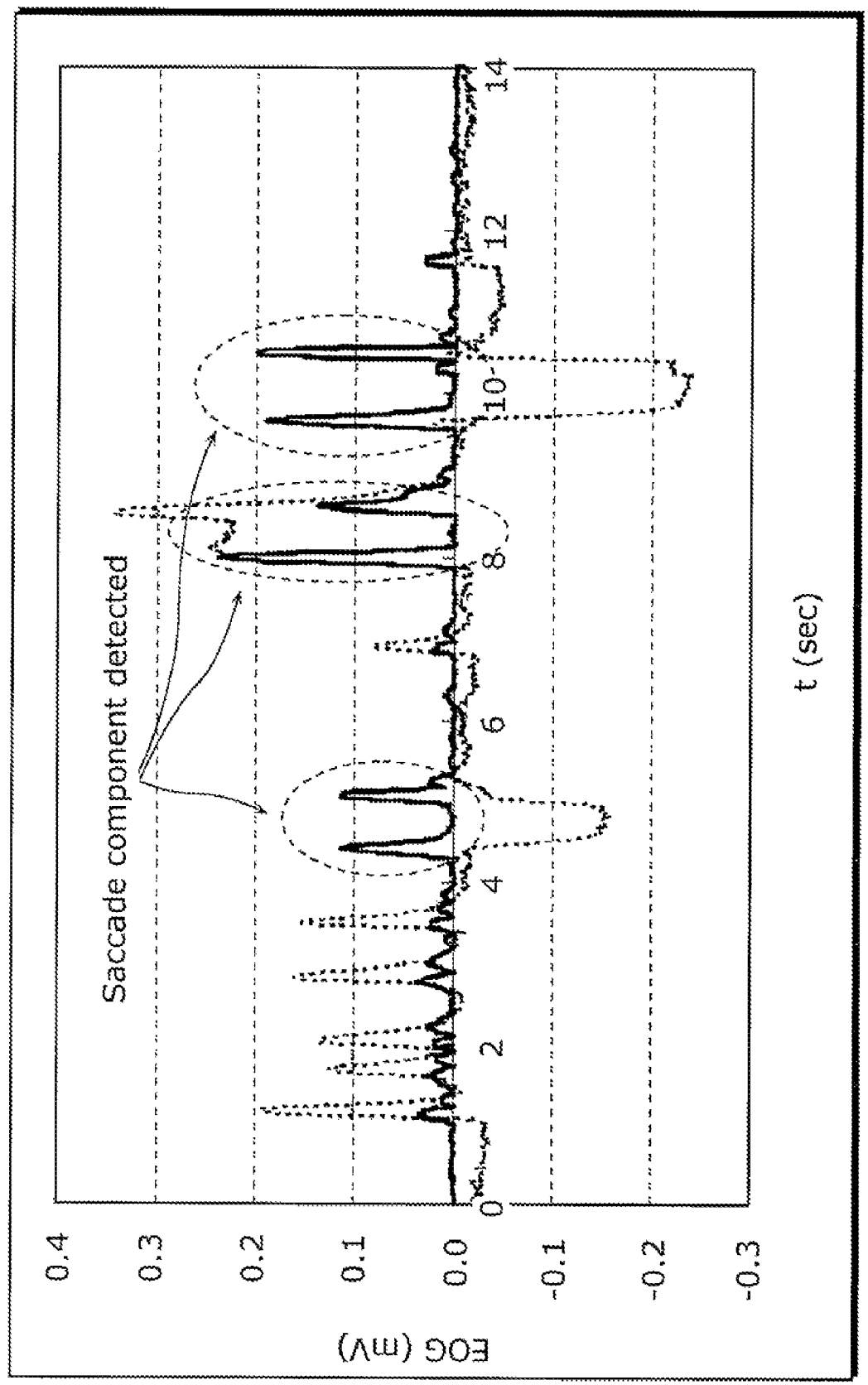
FIG. 51 is a diagram showing a saccade signal obtained by inputting the electro-oculography signal in FIG. 44 into the filtering unit in FIG. 50.

FIG. 51 shows a saccade signal obtained by subtracting the first electro-oculography signal in FIG. 44, on which the minimum value filtering has been performed, from the second electro-oculography signal in FIG. 45, on which the maximum value filtering has been performed. Referring to FIG. 51, it can be seen that only the saccade signal is detected from the electro-oculography original signal.

According to the configuration of the eleventh embodiment described above, the details of filtering to be performed on an electro-oculography original signal are determined according to the method of measuring the electro-oculography original signal, and the filtering is performed according to the determined details. As a result, it is possible to detect a saccade signal regardless of the measuring method employed. More specifically, it is possible to properly detect a saccade without being affected by a blink signal by applying the filtering unit 1120 to the saccade detecting unit 130 shown in FIG. 1.

In addition, when the measuring method is such that a blink signal is generated in the plus direction of an electro-oculography original signal, the filtering details are determined so that the minimum value filtering and the maximum value filtering are consecutively performed in this order, and that the first electro-oculography signal on which the minimum value filtering has been performed is subtracted from the second electro-oculography signal on which the maximum value filtering has been performed. As a result, it is possible to detect the saccade signal while removing the blink signal in the plus direction.

In addition, in the eleventh embodiment, it is possible to detect a saccade signal including a generation time of the saccade signal, by making the number of filter taps of the maximum value filtering greater than the number of filter taps of the minimum value filtering.

On the other hand, when the measuring method is such that a blink signal is generated in the minus direction of an electro-oculography original signal, the filtering details are determined so that the maximum value filtering and the minimum value filtering are consecutively performed in this order, and that the first electro-oculography signal on which the maximum value filtering has been performed is subtracted from the second electro-oculography signal on which the minimum value filtering has been performed. As a result, it is possible to detect the saccade signal while removing the blink signal in the minus direction.

In addition, in the eleventh embodiment, it is possible to detect a saccade signal including a generation time of the saccade signal, by making the number of filter taps of the minimum value filtering greater than the number of filter taps of the maximum value filtering.

It is to be noted that in the above-described ninth to eleventh embodiments, the number of filter taps of one of the minimum value filtering and the maximum value filtering which is to be performed first has been described with the focus on removing a blink signal, detecting a blink signal, or detecting a saccade signal. By adjusting the number of filter taps to a muscle potential, a noise, and the like, the filters may be used for removing the muscle potential, the noise, and the like.

Twelfth Embodiment

Figure 52:
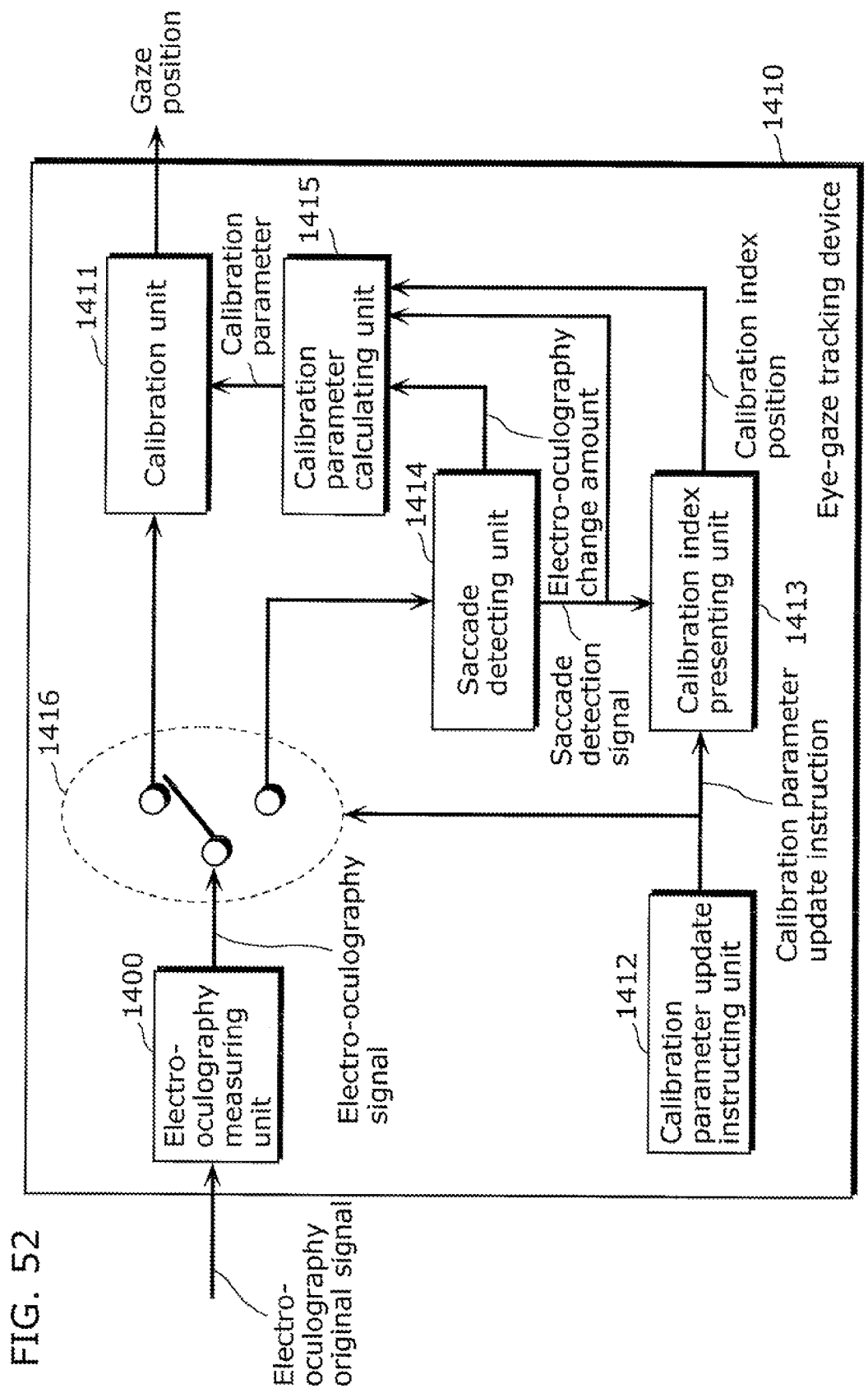
FIG. 52 is a block diagram of an eye-gaze tracking device according to a twelfth embodiment.

FIG. 52 is a block diagram showing a configuration of an eye-gaze tracking device 1410 according to a twelfth embodiment of the present invention. The eye-gaze tracking device 1410 shown in FIG. 52 includes: an electro-oculography measuring unit 1400 attached near a user's eye to measure an electro-oculogram and output an electro-oculography signal; a calibration unit 1411 that converts the electro-oculography signal into a gaze position (which can also be read, hereinafter, as "gaze direction"); a calibration parameter update instructing unit 1412 that instructs update of a calibration parameter; a calibration index presenting unit 1413 that presents a calibration index in response to the calibration parameter update instruction; a saccade detecting unit 1414 that detects a saccade signal from the electro-oculography signal; a calibration parameter calculating unit 1415 that calculates a calibration parameter based on an electro-oculography change amount which is output from the saccade detecting unit 1414 and a position of the calibration index presented by the calibration index presenting unit 1413; and a switch 1416 that switches a destination to which the electro-oculography signal is output, to either the calibration unit 1411 or the saccade detecting unit 1414.

The electro-oculography measuring devices 100 and 400 according to the first to fourth embodiments can be applied to the electro-oculography measuring unit 1400, for example. In addition, the fifth to eleventh embodiments can be applied to the saccade detecting unit 1414, for example.

The electro-oculography measuring unit 1400 typically obtains an electro-oculography original signal from an electrode attached near a user's eye, and outputs an electro-oculography signal from which a drift signal has been removed. The way of attachment is not limited to a specific way. For example, as shown in FIG. 64A and FIG. 64B, the electrode A attached to the outer corner of the eye may be used in combination with the electrode B attached to the inner corner of the eye. Alternatively, as shown in FIG. 38A to FIG. 38D, the electrode may be attached above and/or below the eye. In addition, the electrodes may be attached above and below a temple. It is to be noted that, although the electrode is attached near an eye of the user in the twelfth embodiment, the electrode may be attached near an ear of the user or in contact with the skin, for example.

The calibration unit 1411 calculates a gaze position of the user from the electro-oculography signal by using a calibration parameter held in advance. Here, the calibration parameter is a parameter for converting the electro-oculography signal into an eyeball movement angle. One example of such a parameter is a calibration coefficient α that is used in Expression 1 below.

It is generally known that a measured electro-oculogram Va-b linearly changes when the eyeball movement angle θ is within a certain range. Therefore, the measured electro-oculogram Va-b can be approximated by Expression 1 below, using the calibration coefficient α and the eyeball movement angle θ.

[Math. 1]

$$V_{a\text{-}b} = \alpha \times \theta \quad \text{(Expression 1)}$$

An example of operation for calibration using the EOG method will be described. In the case where an electro-oculogram Ve is input into the calibration unit 1411 as an electro-oculography signal, an eyeball movement angle θ is calculated using Expression 1. Then, a gaze position is calculated from the movement angle θ, using information such as a distance between the user and a gaze object. With the above-described procedure, the gaze position can be calculated from the electro-oculogram. It is to be noted that the method of measuring the distance between the user and the gaze object is not limited to a specific method. For example, a distance measuring sensor and the like may be used.

It is to be noted that the present invention is not limited to the calibration method using Expression 1, and a table that holds a plurality of combinations of an electro-oculography change amount and an eyeball movement angle associated with each other as shown in FIG. 53A may be used as a calibration parameter. It is also possible to use, as a calibration parameter, a table that holds a plurality of combinations of an electro-oculography change amount and a gaze position, such as display coordinates or camera coordinates, associated with each other as shown in FIG. 53B.

The calibration parameter update instructing unit 1412 outputs a calibration parameter update instruction signal to the calibration index presenting unit 1413 and the switch 1416 when an event, such as a start of eye-gaze tracking, occurs. Then, when terminating the update of the calibration parameter, the calibration parameter update instructing unit 1412 stops the output of the calibration parameter update instruction signal.

The switch 1416 switches a destination to which the electro-oculography signal is transmitted, to either the calibration unit 1411 or the saccade detecting unit 1414 according to the calibration parameter update instruction.

The calibration index presenting unit 1413 presents a calibration index to the user upon receiving the calibration parameter update instruction. Then, the calibration index presenting unit 1413 changes the presenting position of the calibration index according to the saccade detection signal provided from the saccade detecting unit 1414.

As an example, in the case where a display 10 as shown in FIG. 54 is used to perform calibration, a first calibration index 20 is displayed at the center of the display 10 in response to the calibration parameter update instruction. After that, when a saccade detection signal is received, a second calibration index 30 is displayed in the upper left. Then, when a saccade detection signal is received again, the next calibration index is displayed in the upper right or the like. In such a manner, it is possible to induce a saccade of a user by changing the position of the calibration index according to a saccade by the user. The position of the calibration index, which is changed according to the saccade by the user as above, is output to the calibration parameter calculating unit 1415.

It is to be noted that, although the first and second calibration indexes 20 and 30 are displayed on the display 10 in the twelfth embodiment, the method of presenting the calibration index is not limited to this. For example, the calibration index may be displayed in a real space by using a laser pointer and the like. In addition, a calibration index may be selected from a plurality of objects (human faces, for example) in the surroundings by using a camera and so on, and audio information allowing the user to recognize the calibration index may be output. That is to say, the calibration index presenting unit 1413 may be anything as long as it outputs information that allows the user to identify the calibration index.

Upon receiving the saccade detection signal from the saccade detecting unit 1414, the calibration parameter calculating unit 1415 updates a calibration parameter using an electro-oculography change amount and a calibration index position. A calculation example of the calibration coefficient α that is one of calibration parameters will be described. First, an eyeball movement angle θ of the user viewing the calibration index is calculated by using, for example, a calibration index position and distance information between the user and the object on which the calibration index is displayed (typically, a display). Then, the calibration coefficient α can be calculated by substituting, into Expression 1, an electro-oculography change amount Vc and the eyeball movement angle θ which have been input. It is to be noted that the method of obtaining the distance information between the user and the display is not limited to a specific method. For example, a distance measuring sensor or the like may be used, or the calibration parameter update instruction may be output after having a user stand at a position predetermined distance away from the display.

Figure 55:
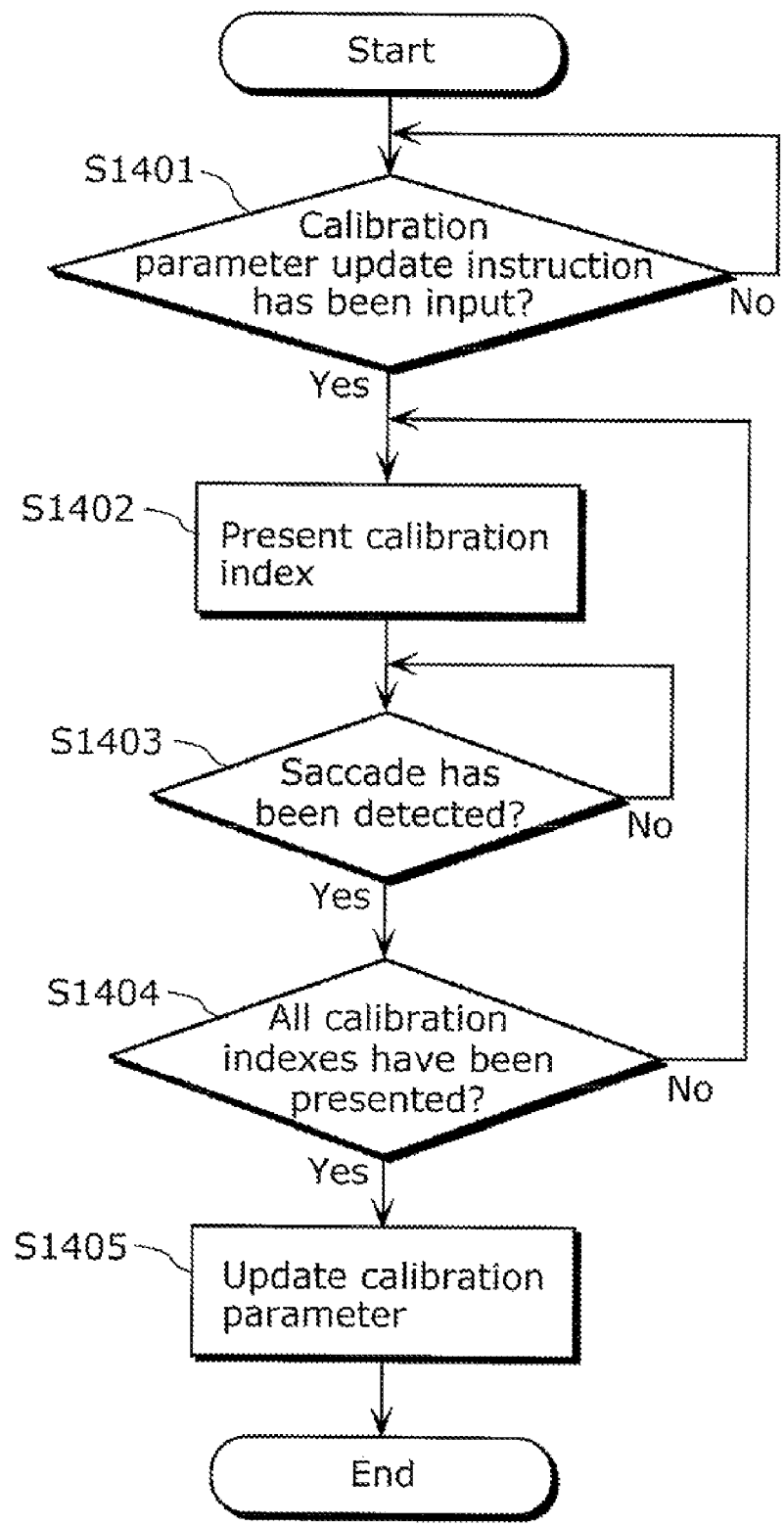
FIG. 55 is a flowchart showing an operation of the eye-gaze tracking device according to the twelfth embodiment.

Next, with reference to FIG. 55, the procedure of updating the calibration parameter, performed by the eye-gaze tracking device 1410 according to the twelfth embodiment, will be described. The eye-gaze tracking device 1410 calculates a new calibration parameter when triggered by an input of a calibration parameter update instruction from outside.

First, the eye-gaze tracking device 1410 monitors an input of the calibration parameter update instruction (S1401). The calibration parameter update instruction is transmitted from the calibration parameter update instructing unit 1412 to the calibration index presenting unit 1413 and the switch 1416. The method of inputting the calibration parameter update instruction is not limited to a specific method. For example, the calibration parameter update instructing unit 1412 may receive an instruction from the user, or may automatically issue the instruction with predetermined timing such as when the eye-gaze tracking device 1410 is powered on.

Next, the calibration index presenting unit 1413 which has received the calibration parameter update instruction (Yes in S1401) presents the first calibration index 20 to the user (S1402). In addition, the calibration index presenting unit 1413 notifies the calibration parameter calculating unit 1415 of position information of the first calibration index 20. The switch 1416 which has likewise received the calibration parameter update instruction switches the output destination of the electro-oculography signal from the calibration unit 1411 to the saccade detecting unit 1414.

Next, the saccade detecting unit 1414 monitors whether or not a saccade signal is included in the electro-oculography signal received via the switch 1416 (S1403). When the first calibration index 20 is displayed on the display 10, the gaze path of the user moves from an arbitrary position to the first calibration index 20. At this time, a saccade signal appears.

It is to be noted that the method of detecting a saccade signal is not limited to a specific method. For example, there is a method of detecting a saccade signal using a maximum value filter, a minimum value filter, a delay device, and so on. The details of the method have already been described above and thus will not be repeated. When a saccade signal is detected (Yes in S1403), the saccade detecting unit 1414 outputs a saccade detection signal to the calibration index presenting unit 1413. Likewise, the saccade detecting unit 1414 outputs the saccade detection signal and the electro-oculography change amount Va-b to the calibration parameter calculating unit 1415.

Next, the calibration index presenting unit 1413 which has received the saccade detection signal determines whether or not all calibration indexes have been presented to the user (S1404). The number of calibration indexes to be presented may be specified in advance, or an inquiry as to whether or not to continue presenting the calibration indexes may be made to the user. It is to be noted that the twelfth embodiment assumes that the number of calibration indexes to be presented is two.

At this point, only the first calibration index 20 is presented (No in S1404), and thus the calibration index presenting unit 1413 presents the next calibration index (S1402). Specifically, the first calibration index 20 is deleted from the display 10 and the second calibration index 30 is displayed on the display 10. In addition, the calibration index presenting unit 1413 notifies the calibration parameter calculating unit 1415 of the position information of the second calibration index 30.

Next, the saccade detecting unit 1414 monitors whether or not a saccade signal is included in the electro-oculography signal (S1403). When the second calibration index 30 is displayed on the display 10, the gaze path of the user moves from the first calibration index 20 to the second calibration index 30. At this time, a saccade signal appears.

The saccade detecting unit 1414 which has detected the saccade signal outputs the saccade detection signal and the electro-oculography change amount Va-b in the same manner as the previous time. In addition, after the second calibration index 30 is presented, the calibration index presenting unit 1413 determines, in Step S1404, that all of the calibration indexes have been presented (Yes in S1404).

Next, the calibration parameter calculating unit 1415 calculates a new calibration parameter based on the position information of the first and second calibration indexes 20 and 30 received from the calibration index presenting unit 1413 and the electro-oculography change amount Va-b after the output of the second calibration index 30, which has been received from the saccade detecting unit 1414. Specifically, an eyeball movement angle θ is calculated using the position information of the first and second calibration indexes 20 and 30. Then, the electro-oculography change amount Va-b and the eyeball movement angle θ are substituted into Expression 1 to calculate a calibration coefficient α.

It is to be noted that in the twelfth embodiment, the method of calculating the calibration coefficient α has been described as an example of updating a calibration parameter. However, the method of updating the calibration parameter is not limited to this. For example, it is also possible to use (i) the electro-oculography change amount and (ii) the eyeball movement angle or the calibration index position, which have been input to the calibration parameter calculating unit 1415, so as to update a table which holds a plurality of combinations of (i) an electro-oculography change amount and (ii) a corresponding eyeball movement angle or gaze position, as shown in FIG. 53A and FIG. 53B. In this case, the number of records in the tables in FIG. 53A and FIG. 53B is increased by increasing the total number of calibration indexes to be presented, and thus it is possible to obtain a more reliable calibration parameter.

According to the configuration of the twelfth embodiment described above, noise in the electro-oculography signal is reduced, the saccade signal is detected from the electro-oculography signal having an improved S/N ratio, and the calibration parameter is updated using the amount of change in the electro-oculogram resulted from saccadic movement. As a result, it is possible to correctly calculate the calibration parameter without being affected by a drift, which is the problem of the conventional methods.

In addition, the noise reduction achieved by the electro-oculography measuring device brings about an improvement in the S/N ratio of the electro-oculography signal, thereby enhancing the accuracy of the eye-gaze tracking.

Furthermore, it is possible to update the calibration parameter while inducing a saccade of a user. As a result, the user only has to follow a calibration index with his eyes, thus allowing reduction of the burden on the user at the time of calibration.

It is also possible to reduce the calibration time by holding the calibration parameter as a table as shown in FIG. 53A and FIG. 53B.

In addition, it is possible to reduce the size of a memory by holding the calibration parameter as a slope of a function (calibration coefficient α) of the electro-oculography change amount Va-b and the eyeball movement angle θ.

Thirteenth Embodiment

Figure 56:
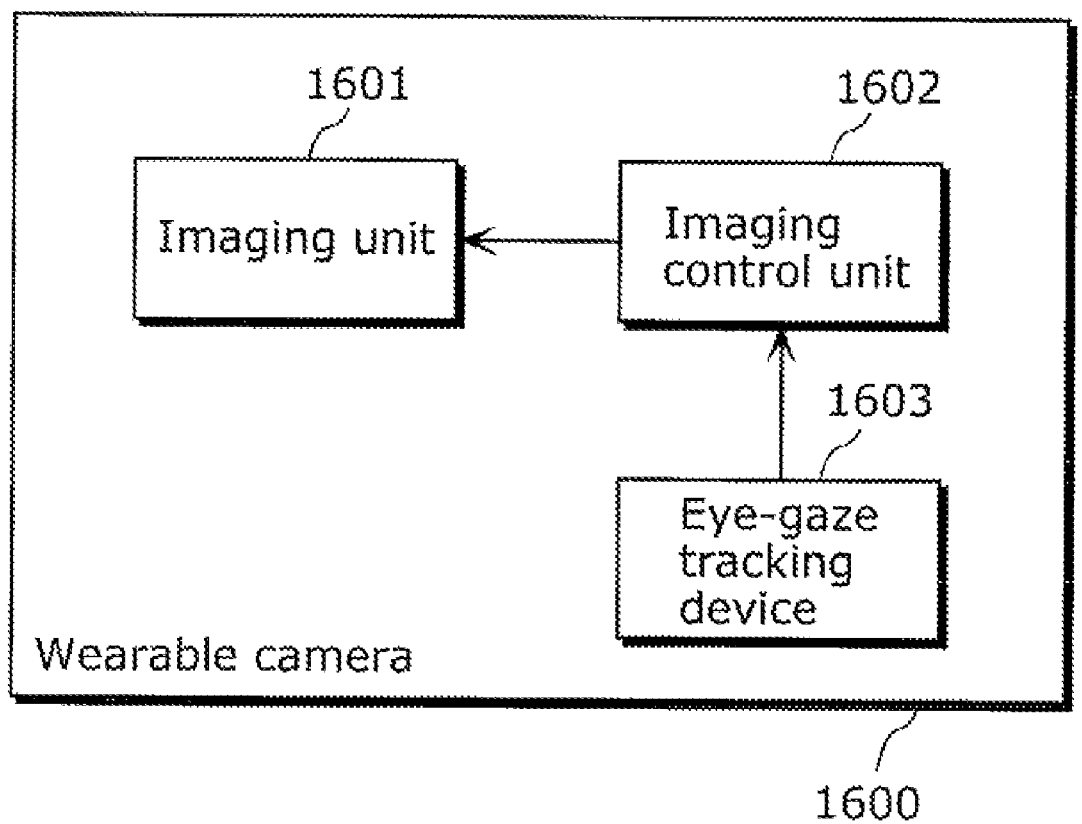
FIG. 56 is a block diagram of a wearable camera according to a thirteenth embodiment.
Figure 57:
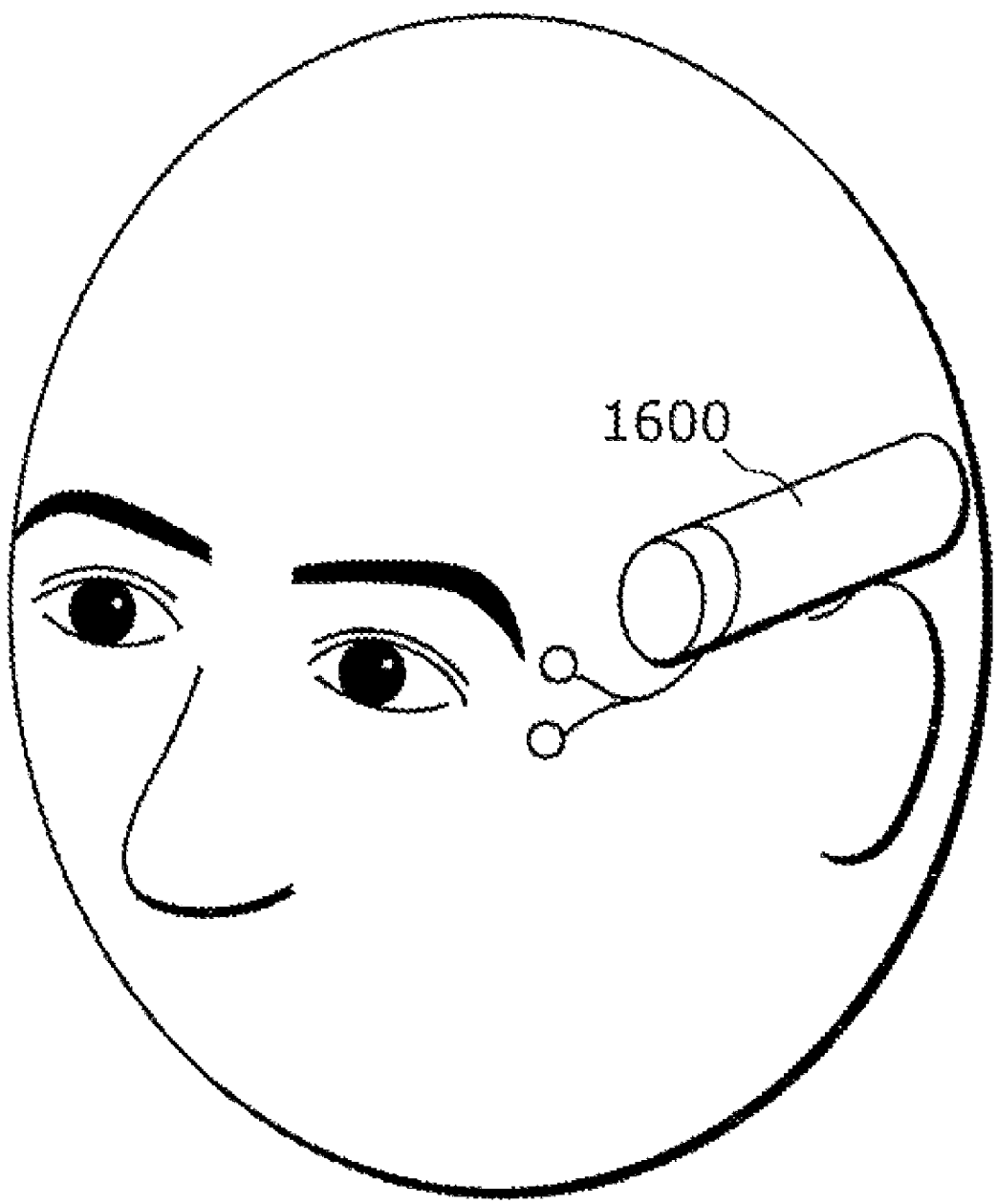
FIG. 57 is a diagram showing a state in which a user is wearing the wearable camera according to the thirteenth embodiment.

Next, with reference to FIGS. 56 and 57, a wearable camera 1600 according to a thirteenth embodiment of the present invention will be described. The wearable camera 1600 is, for example, attached to a side of the user's head and captures an image in a gaze direction of the user. Specifically, the wearable camera 1600 includes an imaging unit 1601, an imaging control unit 1602, and an eye-gaze tracking device 1603.

The wearable camera 1600 may be, for example, a camera which captures a still image or a video camera which captures video. The eye-gaze tracking device 1410 according to the twelfth embodiment can be applied to the eye-gaze tracking device 1603, for example. In addition, as shown in FIG. 57, the electrodes as the electro-oculography measuring unit in the first through fourth embodiments are attached on the upper and lower sides of the temple beside the user's left eye.

The imaging control unit 1602 monitors an output signal provided from the eye-gaze tracking device 1603, and changes the orientation of the imaging unit 1601 following the movement of the user's gaze. This allows the imaging unit 1601 to capture an image in the user's gaze direction.

However, the wearable camera 1600 according to the thirteenth embodiment is not limited to the use as described above. For other uses, it is also possible to apply the wearable camera 1600 to devices such as a device which plots the user's gaze position detected by the eye-gaze tracking device 1603 on the image captured by the imaging unit 1601, or a device which detects the gaze of a driver and alerts danger while driving, or the like.

Fourteenth Embodiment

Figure 58:
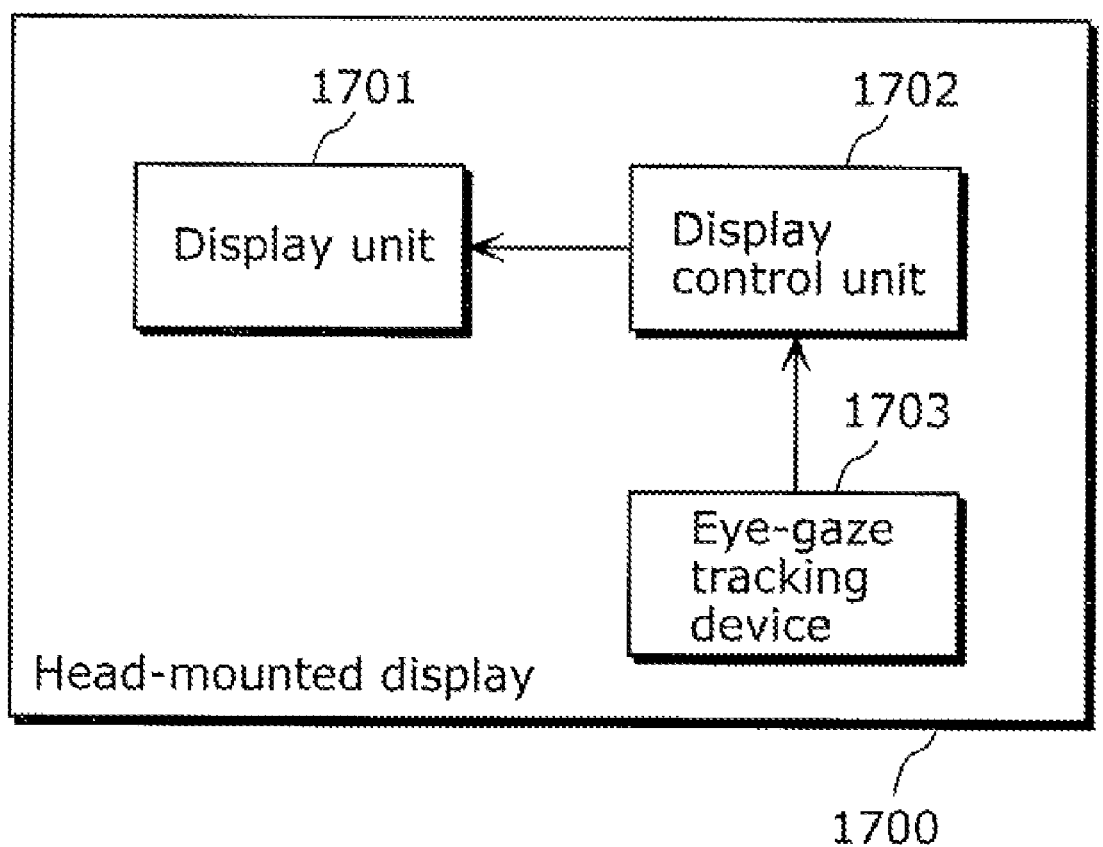
FIG. 58 is a block diagram of a head-mounted display according to a fourteenth embodiment.
Figure 59:
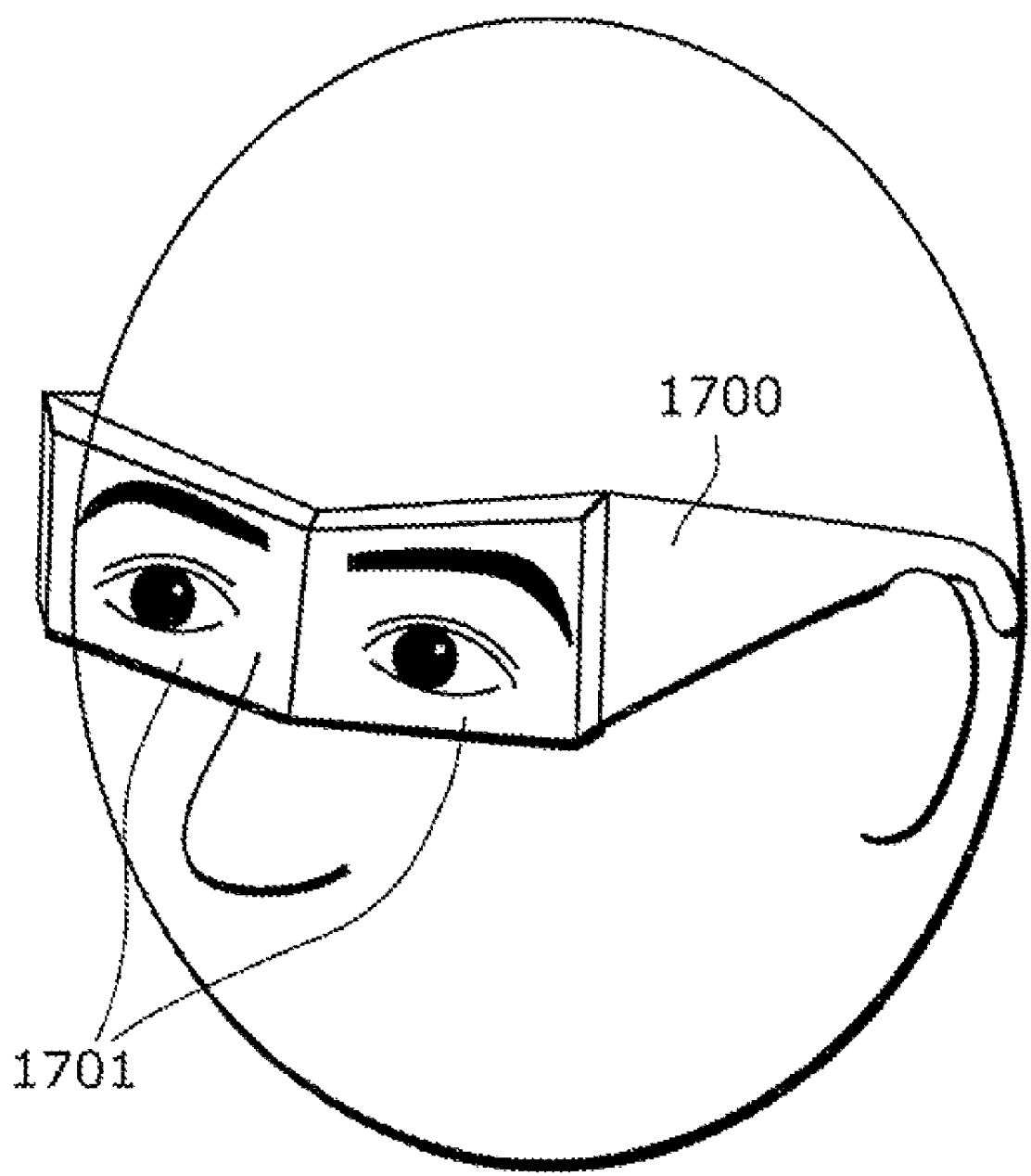
FIG. 59 is a diagram showing a state in which a user is wearing the head-mounted display according to the fourteenth embodiment.

Next, with reference to FIGS. 58 and 59, a head-mounted display 1700 according to a fourteenth embodiment of the present invention will be described. The head-mounted display 1700, for example, has an eyeglass shape, and is a device which displays an image in front of the user's eyes, and moves, in the user's gaze direction, a mouse pointer shown on the displayed image. Specifically, the head-mounted display 1700 includes a display unit 1701, a display control unit 1702, and an eye-gaze tracking device 1703.

Figure 60:
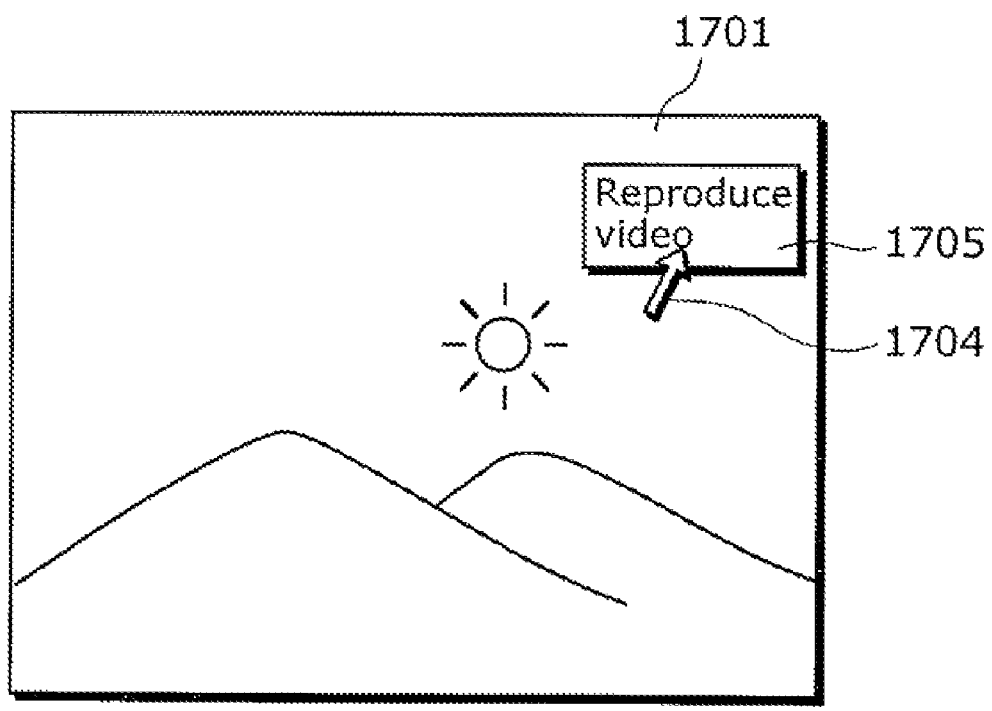
FIG. 60 is a diagram showing an example of an image displayed on a display unit of the head-mounted display according to the fourteenth embodiment.

As shown in FIG. 60, it is assumed that various images are displayed on the display unit 1701, and a mouse pointer 1704 is displayed on such images. The eye-gaze tracking device 1410 according to the twelfth embodiment can be applied to the eye-gaze tracking device 1703, for example.

The display control unit 1702 monitors an output signal provided from the eye-gaze tracking device 1703, and moves the mouse pointer 1704 displayed on the display unit 1701, following the movement of the user's gaze. This allows, for example, a processing executing unit (not shown) to execute processing associated with an icon 1705 (video reproduction processing in the example shown in FIG. 60) pointed by the mouse pointer 1704.

Fifteenth Embodiment

Figure 61:
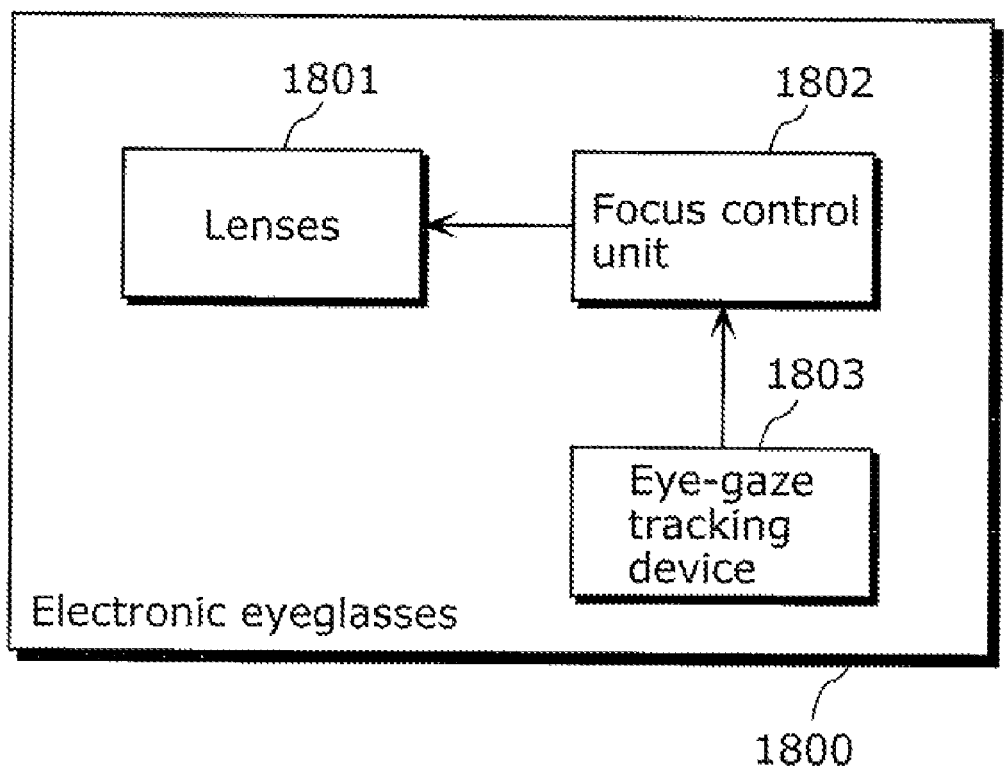
FIG. 61 is a block diagram of electronic eyeglasses according to a fifteenth embodiment.
Figure 62:
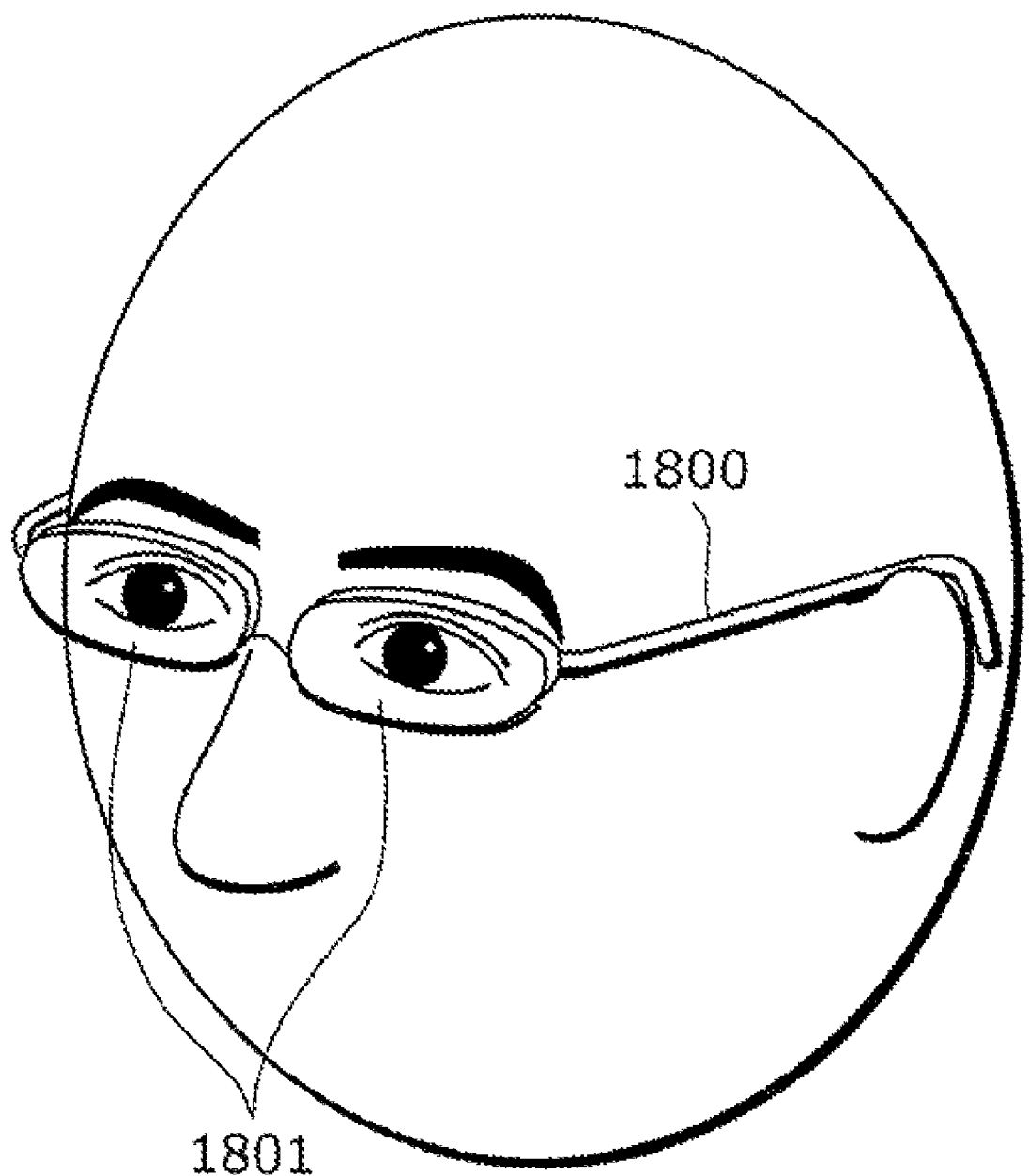
FIG. 62 is a diagram showing a state in which a user is wearing the electronic eyeglasses according to the fifteenth embodiment.

Next, with reference to FIGS. 61 and 62, electronic eyeglasses 1800 according to a fifteenth embodiment of the present invention will be described. The electronic eyeglasses 1800 are eyeglasses capable of changing a focal point of each lens according to the user's gaze position. Specifically, the electronic eyeglasses 1800 include lenses 1801, a focus control unit 1802, and an eye-gaze tracking device 1803.

Each lens 1801 is located before an eye of the user, and has an electronically-changeable focal point.

The eye-gaze tracking device 1410 according to the twelfth embodiment can be applied to the eye-gaze tracking device 1803, for example.

The focus control unit 1802 monitors an output signal provided from the eye-gaze tracking device 1803, and changes the focal point of each lens 1801 following the movement of the user's gaze. For example, when the user is taking a close look at a book to read or the like, the focus control unit 1802 controls the focal point of each lens 1801 so as to focus each lens 1801 at a closer point. In addition, when the user is looking at a landscape in the distance, the focus control unit 1802 controls the focal point of each lens 1801 so as to focus each lens 1801 at a distant point.

It is to be noted that in the fifteenth embodiment, it is assumed that the right and left eyes of the user are gazing at the same point. This allows the eye-gaze tracking device 1803 to detect the gaze position from electro-oculogram.

Sixteenth Embodiment

Figure 63:
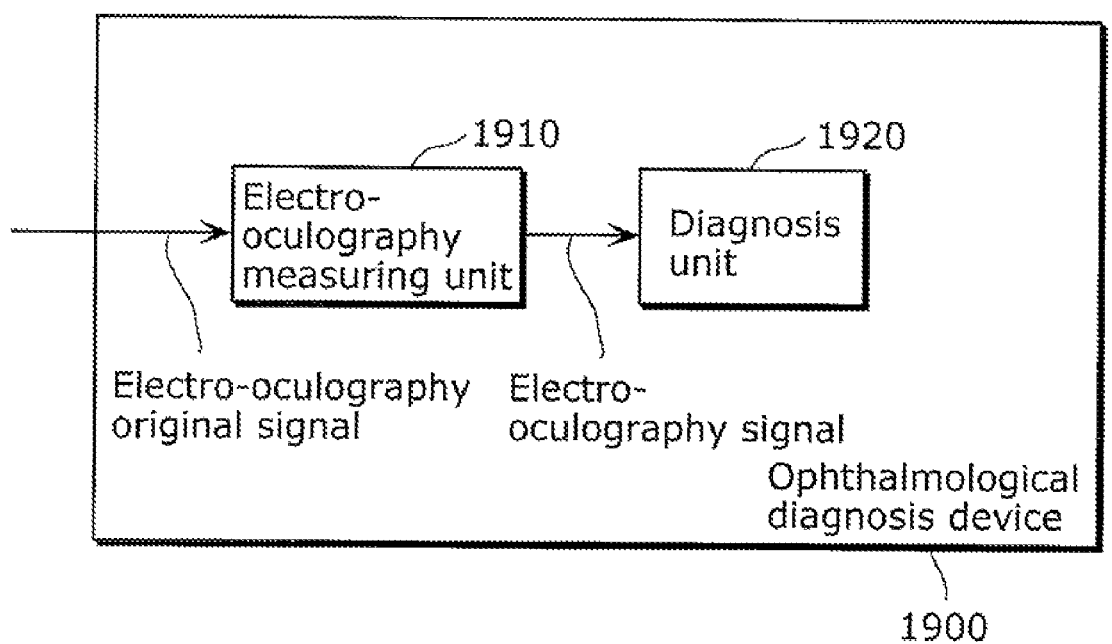
FIG. 63 is a block diagram of an ophthalmological diagnosis device according to a sixteenth embodiment.

Next, with reference to FIG. 63, an ophthalmological diagnosis device 1900 according to a sixteenth embodiment of the present invention will be described. The ophthalmological diagnosis device 1900 is a device which, for example, diagnoses abnormality of retinal resident potential by measuring an electro-oculogram through electrodes attached near the user's eye. Specifically, the ophthalmological diagnosis device 1900 includes: an electro-oculography measuring unit 1910 which is attached near the user's eye to measure an electro-oculogram and output an electro-oculography signal; and a diagnosis unit 1920.

The diagnosis unit 1920 can be used, for example, for calculating Arden ratio that is a ratio between an electro-oculography signal when the eye is adjusted to brightness and an electro-oculography signal when the eye is adjusted to darkness, so as to diagnose the retinal condition from abnormality of the Arden ratio. The electro-oculography measuring devices 100 and 400 according to the first to fourth embodiments can be applied to the electro-oculography measuring unit 1910, for example.

Other Embodiments

It is to be noted that, although the present invention has been described based on the first through sixteenth embodiments above, it is apparent that the present invention is not limited to such embodiments. The present invention also includes such cases as below.

(1) Each of the devices described above is specifically a computer system including a microprocessor, a ROM, a RAM, a hard disk unit, a display unit, a keyboard, a mouse, and so on. A computer program is stored in the RAM or the hard disk unit. The respective devices achieve their functions through the microprocessor's operation according to the computer program. Here, the computer program is a combination of a plurality of instruction codes indicating instructions for the computer, so that a predetermined function is achieved.

(2) Part or all of the constituent elements of the respective devices may be configured from a single system large-scale integrated (LSI) circuit. The system LSI is a super-multifunction LSI manufactured by integrating a plurality of constituent elements on a single chip, and is specifically a computer system including a microprocessor, a ROM, a RAM, and so on. A computer program is stored in the RAM. The system LSI achieves its function through the microprocessor's operation according to the computer program.

(3) Part or all of the constituent elements constituting the respective devices may be configured as an IC card attachable to the respective devices or as a stand-alone module. The IC card or the module is a computer system including a microprocessor, a ROM, a RAM, and so on.< The IC card or the module may include the aforementioned super-multifunction LSI. The respective devices achieve their functions through the microprocessor's operation according to the computer program. The IC card or the module may be tamper-resistant.

(4) The present invention may be realized as the methods described above. In addition, the present invention may be realized as a computer program for executing such methods using a computer, and may also be realized as a digital signal including the computer program.

Moreover, the present invention may also be realized by storing the computer, program or the digital signal in a computer-readable recording medium such as a flexible disc, a hard disk, a CD-ROM, an MO disk, a DVD, a DVD-ROM, a DVD-RAM, a Blu-ray disc (BD), and a semiconductor memory. Furthermore, the present invention may also be realized as the digital signal recorded on these recording media.

In addition, the present invention may also be realized by transmission of the computer program or the digital signal via a telecommunication line, a wireless or wired communication line, a network represented by the Internet, a data broadcast, and so on.

Moreover, the present invention may also be a computer system including a microprocessor and a memory, in which the memory stores the computer program and the microprocessor operates according to the computer program.

Furthermore, by transferring the program or the digital signal recorded on the recording media, or by transferring the program or the digital signal via the network and the like, implementation using another independent computer system is also possible.

(5) It is also possible to combine the above embodiments and variations.

Although only some exemplary embodiments of this invention have been described in detail above with reference to the drawings, those skilled in the art will readily appreciate that many modifications are possible in the exemplary embodiments without materially departing from the novel teachings and advantages of this invention. Accordingly, all such modifications are intended to be included within the scope of this invention.

INDUSTRIAL APPLICABILITY

The present invention is useful as a device or the like which records and reproduces video and/or audio in such fields as broadcasting, communication, and storage. In addition, the present invention is also applicable as a still-picture recording and reproducing device and so on. The present invention is further applicable as a medical device.

What is claimed is:

1. An electro-oculography measuring device which outputs an electro-oculography signal indicating a gaze direction of a user, said electro-oculography measuring device comprising:
   an electro-oculography measuring unit configured to measure an electro-oculography original signal indicating an electro-oculogram resulting from eyeball movement of the user;
   a capturing unit configured to capture a picture in the gaze direction of the user;
   a drift estimation processing unit configured to estimate a drift signal indicating a temporal baseline drift of the electro-oculography original signal; and
   a subtraction unit configured to subtract the drift signal estimated by said drift estimation processing unit from the electro-oculography original signal measured by said electro-oculography measuring unit, so as to output an electro-oculography signal,
   wherein said drift estimation processing unit includes:
   an electro-oculography change amount calculating unit configured to calculate, based on a past electro-oculography signal output from said subtraction unit, an electro-oculography change amount indicating an amount of change in electro-oculogram over a predetermined time period in past;
   a motion vector estimating unit configured to estimate a motion vector of a moving object included in the picture captured by said capturing unit, the motion vector indicating a motion of the moving object in the predetermined time period in the past;
   a drift change amount estimating unit configured to estimate a drift change amount assuming that a change in the gaze direction indicated by the electro-oculography change amount follows the motion of the moving object indicated by the motion vector, the drift change amount being an amount of change in drift signal over the predetermined time period in the past; and
   a drift estimating unit configured to estimate the drift signal by adding the drift change amount estimated by said drift change amount estimating unit to a past drift signal.

2. The electro-oculography measuring device according to claim 1,
   wherein said drift estimation processing unit further includes
   a saccade detecting unit configured to determine, based on the past electro-oculography signal output from said subtraction unit, whether or not saccadic movement occurred in the predetermined time period in the past, and to output a saccade detection signal to said drift estimating unit when determining that the saccadic movement occurred, the saccadic movement being rapid eyeball movement, and
   said drift estimating unit is configured to add the drift change amount output from said drift change amount estimating unit to the past drift signal when not obtaining the saccade detection signal from said saccade detecting unit.

3. The electro-oculography measuring device according to claim 2,
   wherein said electro-oculography change amount calculating unit is further configured to output a fixation detection signal to said drift estimating unit when the calculated electro-oculography change amount is below a predetermined threshold, the fixation detection signal indicating that an eyeball of the user was fixed in the predetermined time period in the past, and
   said drift estimating unit is configured to add the drift change amount output from said drift change amount estimating unit to the past drift signal when not obtaining the fixation detection signal from said electro-oculography change amount calculating unit.

4. The electro-oculography measuring device according to claim 1,
   wherein the predetermined time period in the past is a time period between a first time point in the past and a second time point preceding the first time point,
   said motion vector estimating unit is configured to calculate a plurality of first motion vectors each indicating a position, in a second picture captured at the second time point, of a corresponding one of a plurality of blocks constituting a first picture captured at the first time point, and
   said drift change amount estimating unit is further configured to:
   hold, in advance, a generated-electro-oculogram table in which a gaze direction of the user and a generated electro-oculogram are associated with each other, the generated electro-oculogram being an electro-oculogram generated in the gaze direction;
   calculate, using the generated-electro-oculogram table, a motion-vector-equivalent electro-oculography change amount for each of the first motion vectors estimated by said motion vector estimating unit, the motion-vector-equivalent electro-oculography change amount indicating an amount of change in electro-oculogram assuming that the gaze direction of the user has moved along the motion vector;

extract, from the first motion vectors, one or more first motion vectors having a difference equal to or below a predetermined threshold between a corresponding motion-vector-equivalent electro-oculography change amount and the electro-oculography change amount calculated by said electro-oculography change amount calculating unit; and estimate, as the drift change amount, a difference between a first electro-oculography signal output from said subtraction unit at the first time point and a generated electro-oculogram which, among generated electro-oculograms held in the generated-electro-oculogram table, corresponds to a start position of one of the extracted one or more first motion vectors.

5. The electro-oculography measuring device according to claim 4,
wherein said drift change amount estimating unit is configured to estimate the drift change amount by subtracting, from the first electro-oculography signal, a smallest value of differences between the first electro-oculography signal and generated electro-oculograms each corresponding to a start position of a corresponding one of the extracted first motion vectors.

6. The electro-oculography measuring device according to claim 4,
wherein said drift change amount estimating unit is configured to estimate the drift change amount by subtracting, from the first electro-oculography signal, a median value of differences between the first electro-oculography signal and generated electro-oculograms each corresponding to a start position of a corresponding one of the extracted first motion vectors.

7. The electro-oculography measuring device according to claim 4,
wherein the predetermined time period in the past is a time period between the first time point and a third time point preceding the second time point,
said motion vector estimating unit is further configured to calculate a plurality of second motion vectors each indicating a position, in a third picture captured at the third time point, of a corresponding one of a plurality of blocks constituting the second picture captured at the second time point, and
said drift change amount estimating unit is further configured to:
calculate, using the generated-electro-oculogram table, a motion-vector-equivalent electro-oculography change amount for each of the second motion vectors estimated by said motion vector estimating unit, the motion-vector-equivalent electro-oculography change amount indicating an amount of change in electro-oculogram assuming that the gaze direction of the user has moved along the motion vector;
extract, from combinations of one of the first motion vectors and one of the second motion vectors, one or more first motion vectors having a correlation coefficient equal to or above a predetermined threshold, the correlation coefficient being a correlation coefficient between a transition of a corresponding motion-vector-equivalent electro-oculography change amount and a transition of the electro-oculography change amount from the third time point to the first time point which is calculated by said electro-oculography change amount calculating unit, each of the first motion vector and the second motion vector in each combination representing a motion with respect to a same block; and
estimate, as the drift change amount, a difference between the first electro-oculography signal output from said subtraction unit at the first time point and a generated electro-oculogram which, among the generated electro-oculograms held in the generated-electro-oculogram table, corresponds to a start position of one of the extracted one or more first motion vectors.

8. The electro-oculography measuring device according to claim 7,
wherein said drift change amount estimating unit is further configured to estimate the drift change amount by multiplying, by a corresponding correlation coefficient, a difference between the first electro-oculography signal output from said subtraction unit at the first time point and a generated electro-oculogram corresponding to a start position of one of the extracted one or more first motion vectors.

9. The electro-oculography measuring device according to claim 1,
wherein the predetermined time period in the past is a time period between a first time point in the past and a second time point preceding the first time point,
said motion vector estimating unit is configured to calculate a plurality of motion vectors each indicating a position, in a second picture captured at the second time point, of a corresponding one of a plurality of blocks constituting a first picture captured at the first time point, and
said drift change amount estimating unit is further configured to:
hold, in advance, a generated-electro-oculogram table in which a gaze direction of the user and a generated electro-oculogram are associated with each other, the generated electro-oculogram being an electro-oculogram generated in the gaze direction;
calculate, using the generated-electro-oculogram table, a motion-vector-equivalent electro-oculography change amount for each of the motion vectors estimated by said motion vector estimating unit, the motion-vector-equivalent electro-oculography change amount indicating an amount of change in electro-oculogram assuming that the gaze direction of the user has moved along the motion vector; and
estimate, as the drift change amount, a difference between the electro-oculography change amount calculated by said electro-oculography change amount calculating unit and a largest one of motion-vector-equivalent electro-oculography change amounts which respectively correspond to the motion vectors.

10. The electro-oculography measuring device according to claim 2, wherein said saccade detecting unit includes:
a delayed signal generating unit configured to delay the electro-oculography signal for a predetermined delay time to output a delayed signal; and
a subtraction unit configured to subtract the delayed signal from the electro-oculography signal to generate an output signal, and
said saccade detecting unit is configured to output the saccade detection signal to said drift estimating unit when the output signal is above a predetermined threshold.

11. The electro-oculography measuring device according to claim 10, wherein the predetermined delay time is shorter than a time period for which the user gazes at an object.

12. The electro-oculography measuring device according to claim 2,
wherein said saccade detecting unit includes:
a first filtering unit configured to perform one of maximum value filtering and minimum value filtering on the electro-oculography signal to output a first electro-oculography signal; and
a subtraction unit configured to subtract one of the first electro-oculography signal and a second electro-oculography signal from the other one of the first electro-oculography signal and the second electro-oculography signal to generate an output signal, the second electro-oculography signal being obtained from the electro-oculography signal, and
said saccade detecting unit is configured to output the saccade detection signal to said drift estimating unit when the output signal is above a predetermined threshold.

13. The electro-oculography measuring device according to claim 12,
wherein said saccade detecting unit further includes
a second filtering unit configured to perform the other one of the maximum value filtering and the minimum value filtering on the electro-oculography signal to output the second electro-oculography signal.

14. The electro-oculography measuring device according to claim 12,
wherein said saccade detecting unit further includes
a second filtering unit configured to perform the other one of the maximum value filtering and the minimum value filtering on the first electro-oculography signal to output the second electro-oculography signal.

15. An ophthalmological diagnosis device comprising:
the electro-oculography measuring device according to claim 1; and
a diagnosis unit configured to diagnose a condition of an eye of the user based on the electro-oculography signal output from said electro-oculography measuring device.

16. An eye-gaze tracking device which detects a gaze direction of a user from an electro-oculogram, said eye-gaze tracking device comprising:
the electro-oculography measuring device according to claim 1;
a calibration index presenting unit configured to present a calibration index to the user;
a saccade detecting unit configured to detect saccadic movement from the electro-oculography signal output from said electro-oculography measuring device, and to output an electro-oculography change amount that is an amount of change in electro-oculogram before and after the saccadic movement, the saccadic movement being rapid eyeball movement which occurs when a gaze position of the user moves to the calibration index presented by said calibration index presenting unit;
a calibration parameter calculating unit configured to calculate a calibration parameter based on a position of the calibration index presented by said calibration index presenting unit and the electro-oculography change amount output from said saccade detecting unit; and
a calibration unit configured to detect the gaze direction of the user from the electro-oculography signal based on the calibration parameter.

17. A wearable camera which captures an image in a gaze direction of a user, said wearable camera comprising:
an imaging unit;
the eye-gaze tracking device according to claim 16; and
an imaging control unit configured to cause said imaging unit to capture an image in a gaze direction detected by said eye-gaze tracking device.

18. A head-mounted display which moves a mouse pointer in a gaze direction of a user, said head-mounted display comprising:
a display unit configured to display an image and the mouse pointer;
the eye-gaze tracking device according to claim 16; and
a display control unit configured to move the mouse pointer displayed on said display unit, in a gaze direction detected by said eye-gaze tracking device.

19. Electronic eyeglasses which change a focal point of each of lenses according to a gaze position of a user, said electronic eyeglasses comprising:
lenses each having a changeable focal point;
the eye-gaze tracking device according to claim 16; and
a focus control unit configured to change the focal point of each of said lenses according to a gaze position detected by said eye-gaze tracking device.

20. An electro-oculography measuring method for outputting an electro-oculography signal indicating a gaze direction of a user, said electro-oculography measuring method comprising:
measuring an electro-oculography original signal indicating an electro-oculogram resulting from eyeball movement of the user;
capturing a picture in the gaze direction of the user;
estimating a drift signal indicating a temporal baseline drift of the electro-oculography original signal; and
subtracting the drift signal estimated in said estimating of a drift signal from the electro-oculography original signal measured in said measuring, so as to output an electro-oculography signal,
wherein said estimating of a drift signal includes:
calculating, based on a past electro-oculography signal output in said subtracting, an electro-oculography change amount indicating an amount of change in electro-oculogram over a predetermined time period in past;
estimating a motion vector of a moving object included in the picture captured in said capturing, the motion vector indicating a motion of the moving object in the predetermined time period in the past;
estimating a drift change amount assuming that a change in the gaze direction indicated by the electro-oculography change amount follows the motion of the moving object indicated by the motion vector, the drift change amount being an amount of change in drift signal over the predetermined time period in the past; and
estimating the drift signal by adding the drift change amount estimated in said estimating of a drift change amount, to a past drift signal.

21. A non-transitory computer-readable recording medium for use in a computer, said recording medium having a program recorded thereon for causing the computer to output an electro-oculography signal indicating a gaze direction of a user, the program causing the computer to execute:
measuring an electro-oculography original signal indicating an electro-oculogram resulting from eyeball movement of the user;
capturing a picture in the gaze direction of the user;
estimating a drift signal indicating a temporal baseline drift of the electro-oculography original signal; and subtracting the drift signal estimated in said estimating of a drift signal from the electro-oculography original signal measured in said measuring, so as to output an electro-oculography signal, wherein said estimating of a drift signal includes:

calculating, based on a past electro-oculography signal output in said subtracting, an electro-oculography change amount indicating an amount of change in electro-oculogram over a predetermined time period in past;

estimating a motion vector of a moving object included in the picture captured in said capturing, the motion vector indicating a motion of the moving object in the predetermined time period in the past;

estimating a drift change amount assuming that a change in the gaze direction indicated by the electro-oculography change amount follows the motion of the moving object indicated by the motion vector, the drift change amount being an amount of change in drift signal over the predetermined time period in the past; and estimating the drift signal by adding the drift change amount estimated in said estimating of a drift change amount, to a past drift signal.

* * * * *